(12) United States Patent
Alkan et al.

(10) Patent No.: US 11,149,063 B2
(45) Date of Patent: Oct. 19, 2021

(54) PEPTIDE INHIBITORS OF TIGHT JUNCTION PERMEABILITY

(71) Applicant: ALBA THERAPEUTICS CORPORATION, Baltimore, MD (US)

(72) Inventors: Sefik Alkan, Baltimore, MD (US); Amir Tamiz, Silver Spring, MD (US); Kelly Marie Kitchens, Laurel, MD (US); Malarvizhi Durai, Ellicott City, MD (US); Neil Poloso, Rockville, MD (US); Rosa A. Carrasco, Baltimore, MD (US)

(73) Assignee: ALBA THERAPEUTICS CORPORATION, Baltimore, MD (US)

( * ) Notice: Subject to any disclaimer, the term of this patent is extended or adjusted under 35 U.S.C. 154(b) by 0 days.

(21) Appl. No.: 16/692,640

(22) Filed: Nov. 22, 2019

(65) Prior Publication Data

US 2020/0231626 A1    Jul. 23, 2020

Related U.S. Application Data

(60) Division of application No. 15/860,118, filed on Jan. 2, 2018, now Pat. No. 10,526,372, which is a continuation of application No. 15/160,259, filed on May 20, 2016, now abandoned, which is a continuation of application No. 14/592,623, filed on Jan. 8, 2015, now abandoned, which is a continuation of application No. 12/991,658, filed as application No. PCT/US2009/042973 on May 6, 2009, now Pat. No. 8,957,032.

(60) Provisional application No. 61/050,915, filed on May 6, 2008.

(51) Int. Cl.
| | |
|---|---|
| *C07K 7/06* | (2006.01) |
| *A61K 45/06* | (2006.01) |
| *C07K 5/083* | (2006.01) |
| *C07K 5/087* | (2006.01) |
| *C07K 5/09* | (2006.01) |
| *C07K 5/093* | (2006.01) |
| *C07K 5/097* | (2006.01) |
| *C07K 5/103* | (2006.01) |
| *A61K 38/06* | (2006.01) |
| *A61K 38/07* | (2006.01) |
| *A61K 38/08* | (2019.01) |
| *A61K 38/00* | (2006.01) |

(52) U.S. Cl.
CPC .............. *C07K 7/06* (2013.01); *A61K 38/06* (2013.01); *A61K 38/07* (2013.01); *A61K 38/08* (2013.01); *A61K 45/06* (2013.01); *C07K 5/081* (2013.01); *C07K 5/0804* (2013.01); *C07K 5/0806* (2013.01); *C07K 5/0808* (2013.01); *C07K 5/0812* (2013.01); *C07K 5/0815* (2013.01); *C07K 5/0817* (2013.01); *C07K 5/0819* (2013.01); *C07K 5/0821* (2013.01); *C07K 5/101* (2013.01); *C07K 5/1008* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,458,925 B1 * | 10/2002 | Fasano | ...................... A61P 1/04 530/328 |
| 6,670,448 B2 | 12/2003 | Fasano | |
| 6,936,689 B2 | 8/2005 | Fasano | |
| 7,026,294 B2 | 4/2006 | Fasano et al. | |
| 7,189,696 B2 | 3/2007 | Fasano | |
| 7,531,504 B2 | 5/2009 | Fasano | |
| 7,531,512 B2 | 5/2009 | Fasano et al. | |
| 7,582,603 B2 | 9/2009 | Fasano | |
| 8,034,776 B2 | 10/2011 | Fasano et al. | |
| 8,168,594 B2 | 5/2012 | Paterson et al. | |
| 8,183,211 B2 | 5/2012 | Fasano | |
| 8,299,017 B2 | 10/2012 | Paterson et al. | |
| 8,785,374 B2 | 7/2014 | Tamiz | |

(Continued)

FOREIGN PATENT DOCUMENTS

| | | |
|---|---|---|
| WO | 20007609 | 2/2000 |
| WO | 2008150981 | 12/2008 |
| WO | WO2008150981 | * 12/2008 |

OTHER PUBLICATIONS

Arrieta, et al., "Alterations in Intestinal Permeability", Gut, Oct. 2006, vol. 55, No. 10, pp. 1512-1520.

(Continued)

*Primary Examiner* — Maury A Audet
(74) *Attorney, Agent, or Firm* — Morgan, Lewis & Bockius LLP

(57) ABSTRACT

Novel compounds and methods for the inhibition of biological barrier permeability and for the inhibition of peptide translocation across biological barriers are identified. Assays for determining modulators of biological barrier permeability and for peptide translocation across biological barriers are provided. Methods for treating diseases relating to aberrant biological barrier permeability and peptide translocation across biological barriers are provided. Such diseases include celiac disease, necrotizing enterocolitis, diabetes, cancer, inflammatory bowel diseases, asthma, COPD, excessive or undesirable immune response, gluten sensitivity, gluten allergy, food allergy, rheumatoid arthritis, multiple sclerosis, immune-mediated or type 1 diabetes mellitus, systemic lupus erythematosus, psoriasis, scleroderma and autoimmune thyroid diseases.

9 Claims, 12 Drawing Sheets

Specification includes a Sequence Listing.

(56) References Cited

U.S. PATENT DOCUMENTS

| | | |
|---|---|---|
| 8,796,203 B2 | 8/2014 | Paterson et al. |
| 8,957,032 B2 | 2/2015 | Alkan et al. |
| 9,051,349 B2 * | 6/2015 | Callens .................. C07K 7/06 |
| 9,241,969 B2 | 1/2016 | Paterson et al. |
| 9,265,811 B2 | 2/2016 | Paterson et al. |
| 9,279,807 B2 | 3/2016 | Fasano et al. |
| 10,723,763 B2 | 7/2020 | Paterson et al. |
| 2006/0287233 A1 | 12/2006 | Fasano et al. |
| 2007/0196501 A1 | 8/2007 | Paterson et al. |
| 2008/0103100 A1 | 5/2008 | Fasano et al. |
| 2010/0280221 A1 | 11/2010 | Callens et al. |
| 2012/0076861 A1 | 3/2012 | Fasano et al. |

OTHER PUBLICATIONS

International Search Report issued in Appl. No. PCT/US2009/042973 dated Dec. 15, 2009, 5 pages.
McGregor, "Discovering and improving novel peptide therapeutics", Current Opinion in Pharmacology 2008, 8:616-619.
Holmes, et al., "Intestinal brush border revisited", Gut, 1989, 30, 1667-1678.

* cited by examiner

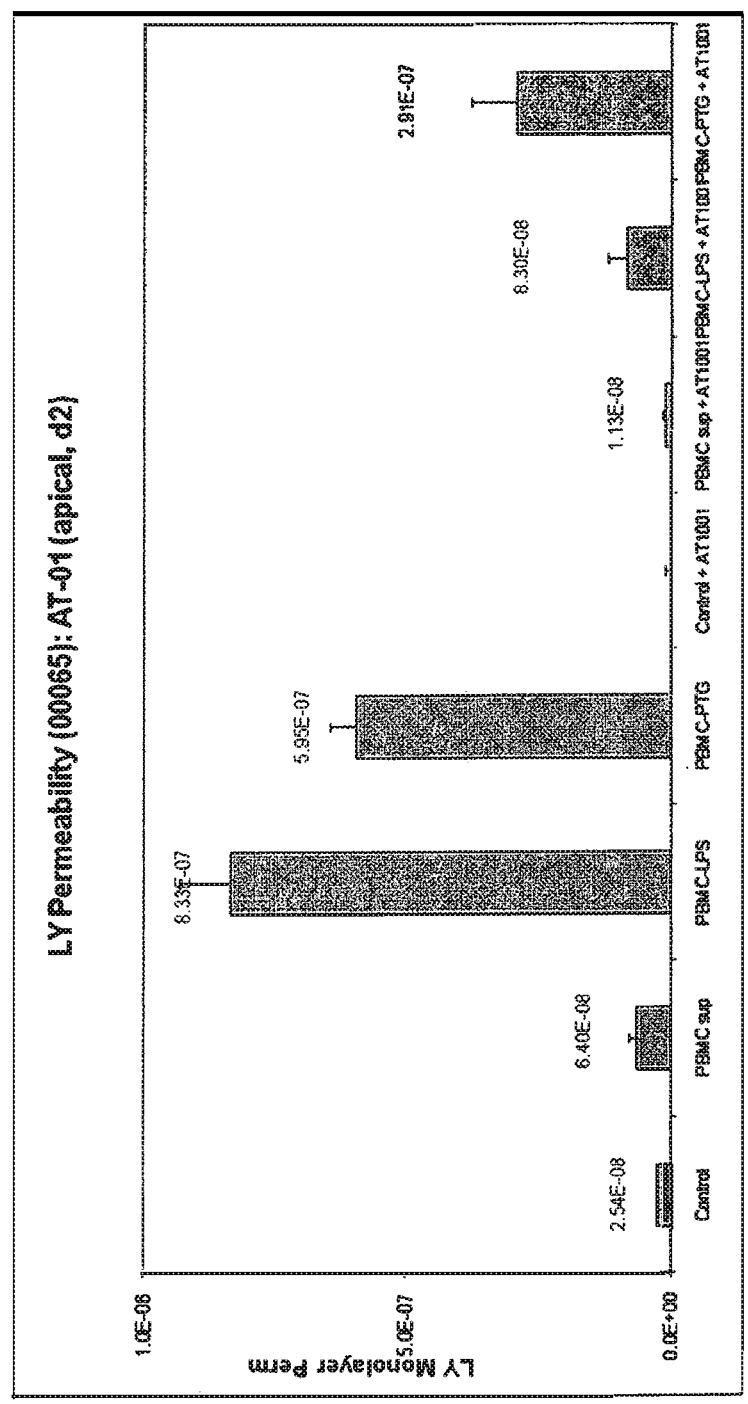

PEPTIDE INHIBITORS OF TIGHT JUNCTION PERMEABILITY

PRIORITY

This application claims priority to U.S. Provisional Application No. 61/050,915 filed May 6, 2008, which is hereby incorporated by reference in its entirety.

TECHNICAL FIELD OF THE INVENTION

This invention is related to the area of gastrointestinal inflammation. In particular, it relates to compounds and methods for the treatment of gastrointestinal inflammation.

DESCRIPTION OF THE TEXT FILE SUBMITTED ELECTRONICALLY

The contents of the text file submitted electronically herewith are incorporated herein by reference in their entirety: A computer readable format copy of the Sequence Listing (Filename: "ALB-047DV_ST25.txt"; Date recorded: Apr. 10, 2020; File size: 83,716 bytes).

BACKGROUND OF THE INVENTION

Environmental stimuli, such as microorganisms and gluten, can lead to increased permeability of biological barriers and initiate significant pathological events in the intestine, brain, heart, and other organs. The pathological consequences of such stimuli include the development of inflammatory diseases. Such external stimuli are presumed to exert physiological effects on biological barriers, possibly through interaction with specific cell surface receptors. However, the mechanisms used remain unclear, and specific cell surface receptors have yet to be confirmed.

Many inflammatory diseases, including those that are understood to involve increased permeability of biological barriers, are thought to be autoimmune. Such diseases include celiac disease, rheumatoid arthritis, multiple sclerosis, immune-mediated or type 1 diabetes mellitus, inflammatory bowel diseases, systemic lupus erythematosus, psoriasis, scleroderma, necrotizing enterocolitis and autoimmune thyroid diseases. Prolonged inflammation is often associated with these diseases, although the inflammation is thought to be a sequela rather than a primary pathological insult.

Biological Barrier Dysfunction

Biological barrier function relies upon the structural and functional integrity of tight junctions (TJ), which are one of the hallmarks of absorptive and secretory epithelia. They act as a boundary that physically separates apical and basolateral compartments of epithelial cells, and they selectively regulate the passage of materials through the epithelia by controlling access to the space between the epithelial cells (the paracellular pathway). To meet the many diverse physiological and pathological challenges to which epithelia are subjected, the tight junctions must be capable of rapid, physiologic, reversible, transient, energy dependent, and coordinated responses that require the presence of a complex regulatory system. Examples of epithelia containing tight junctions include, but are not limited to, the intestines (particularly the small intestine), and the blood brain barrier.

In the absence of stimuli, tight junctions are closed restricting access to the paracellular pathway. In the presence of stimuli, the tight junctions are reversibly opened. Certain bacteria have been shown to have toxins that stimulate the opening of tight junctions. *Vibrio cholerae* infected with the filamentous bacteriophage CTXΦ, produces a toxin (zonula occludens toxin, ZOT) that has been shown to cause opening of tight junctions. It has been shown that 6 His-ΔG, an N-terminal deletion of ZOT in which the first 264 amino acids have been deleted and replaced with a six histidine purification tag, retains the ability to open tight junctions.

Physiological changes in paracellular permeability, which are due to TJ regulation, can be measured as variations in transepithelial conductance. Such variations can usually be attributed to changes in paracellular permeability since the resistances of epithelial plasma membranes are relatively high. TJ represent the major barrier in the paracellular pathway, and the electrical resistance of epithelial tissues seems to depend on their integrity.

Environmental stimuli, including for example, microorganisms and gluten, can increase permeability of biological barriers as measured by a decrease in trans-epithelial electrical resistance (TEER) (ex vivo) or the Lactulose/mannitol test (in vivo). Such increases in barrier permeability are due primarily to TJ rearrangements, and they are believed to underlie many diseases including a large number of inflammatory conditions.

TJ dysfunction occurs in a variety of clinical conditions, including food allergies, infections of the gastrointestinal tract, autoimmune diseases, celiac disease and inflammatory bowel diseases. Healthy, mature gut mucosa With its intact tight junction serves as the main barrier to the passage of macromolecules. During the healthy state, small quantities of immunologically active antigens cross the gut host barrier. These antigens are absorbed across the mucosa through at least two pathways. Up to 90% of the absorbed proteins cross the intestinal barrier via the transcellular pathway, followed by lysosomal degradation that converts proteins into smaller, non-immunogenic peptides. These residual peptides are transported as intact proteins through the paracellular pathway, which mediates a subtle, but sophisticated, regulation of intercellular tight junction that leads to antigen tolerance.

In normal bowels, the immune reaction is regulated to maintain homeostasis of the gut. When TJ integrity is compromised, in premature infants or on exposure to environmental stimuli, radiation, chemotherapy, or toxins, a deleterious immune response to environmental antigens may develop. This response can result in autoimmune diseases and food allergies that lead to inflammation.

Inflammatory bowel disease (IBD) is a phrase used to describe an inappropriate immune response that occurs in the bowels of affected individuals. Two major types of IBD have been described: Crohn's disease and ulcerative colitis (UC). Both forms of IBD show abnormal profiles of T cell mediated immunity. In the gut of Crohn's disease a strong Th1 reaction is induced; the Th2 response is upregulated in the colon of UC.

The barrier function of the intestines is impaired in IBD. For example, Crohn's disease is associated with increased permeability of the intestinal barrier even in quiescent patients. A TNF-α-induced increase in intestinal epithelial tight junction (TJ) permeability has been proposed to be an important proinflammatory mechanism contributing to intestinal inflammation in Crohn's disease and other inflammatory conditions. Increased intestinal permeability during episodes of active disease correlates with destruction or rearrangement of TJ protein complexes.

Examples of inflammatory diseases and disorders that may be treated using the instant invention include, for example, celiac disease, necrotizing enterocolitis, rheumatoid arthritis, multiple sclerosis, immune-mediated or type 1 diabetes mellitus, inflammatory bowel diseases (Crohn's disease and ulcerative colitis), systemic lupus erythematosus, psoriasis, scleroderma, and autoimmune thyroid diseases. Prolonged inflammation is often associated with these diseases, although the inflammation is thought to be a sequela rather than a primary pathological insult.

Other diseases and disorders associated with biological barrier dysfunction and which may be treated using the instant inventions include, for example, celiac disease, asthma, acute lung injury, acute respiratory distress syndrome, chronic obstructive pulmonary disease, inflammation (e.g., psoriasis and other inflammatory dermatoses), asthma, allergy, cell proliferative disorders (e.g., hyperproliferative skin disorders including skin cancer), metastasis of cancer cells, ion transport disorders such as magnesium transport defects in the kidney, and exposure to Clostridium perfringens enterotoxin (CPE), autoimmune encephalomyelitis, optic neuritis, progressive multifocal leukoencephalopathy (PML), primary biliary cirrhosis, IgA nephropathy, Wegener's granulomatosis, multiple sclerosis, scleroderma, systemic sclerosis, Hashimoto's thyroiditis (underactive thyroid), Graves' disease (overactive thyroid), autoimmune hepatitis, autoimmune inner ear disease, bullous pemphigoid, Devic's syndrome, Goodpasture's syndrome, Lambert-Eaton myasthenic syndrome (LEMS), autoimmune lymphproliferative syndrome (ALPS), paraneoplastic syndromes, polyglandular autoimmune syndromes (PGA), alopecia areata, gastrointestinal inflammation that gives rise to increased intestinal permeability, intestinal conditions that cause protein losing enteropathy, C. difficile infection, enterocolitis, shigellosis, viral gastroenteritis, parasite infestation, bacterial overgrowth, Whipple's disease, diseases with mucosal erosion or ulcerations, gastritis, gastric cancer, collagenous colitis, and mucosal diseases without ulceration, Menetrier's disease, eosinophilic gastroenteritis, diseases marked by lymphatic obstruction, congenital intestinal lymphangiectasia, sarcoidosis lymphoma, mesenteric tuberculosis, after surgical correction of congenital heart disease, and food allergies, primarily to milk.

Inflammation

Inflammation plays a central role in the pathology of disease conditions that adversely affect a considerable proportion of the population in developed countries. This process is mediated by cytokines, a system of polypeptides that enable one cell to signal to initiate events in another cell that initiate inflammatory sequelae. Normally, the system acts as part of a defensive reaction against infectious agents, harmful environmental agents, or malignantly transformed cells. But when inflammation exceeds the requirements of its defensive role, it can initiate adverse clinical effects, such as arthritis, septic shock, inflammatory bowel disease, and a range of other human disease conditions.

Immune cells such as monocytes and macrophages secrete cytokines including tumor necrosis factor-α (TNFα) and tumor necrosis factor-β (TNFβ) in response to endotoxin or other stimuli. Cells other than monocytes or macrophages also make cytokines including TNFα. For example, human non-monocytic tumor cell lines produce TNF. CD4$^+$ and CD8$^+$ peripheral blood T lymphocytes and some cultured T and B cell lines also produce TNFα. A large body of evidence associates cytokines such as TNFα with infections, immune disorders, neoplastic pathologies, autoimmune pathologies and graft-versus host pathologies.

Small-molecule antirheumatic drugs such as methotrexate and sulfasalazine are insufficient to control inflammation in about two-thirds of arthritis patients. New biological agents developed in the last decade have proved to be effective for a majority of patients unresponsive to traditional drugs. The target for such agents is often one of the cytokine pathways—either capturing the ligand conveying the signal from one cell to another, or blocking the receptor at the surface of the effector cell, preventing transduction of the cytokine signal, thereby forestalling the inflammatory events.

A leading biological agent for treating inflammatory conditions is Enbrel™ (Etanercept), marketed by Amgen Corp. It is a chimeric molecule comprising the extracellular portion of the human TNF receptor linked as a dimer to the IgG Fc region. The compound interferes with the binding of TNF to cell-surface TNF receptors—showing the importance of modulating the TNF pathway for clinical therapy of inflammatory conditions.

Other TNFα modulating agents currently licensed in the U.S. for treating inflammatory conditions include Cimzia™ (certolizumab pegol), a pegylated antibody fragment that binds to TNFα; Remicade™ (Infliximab), a chimeric antibody that binds TNFα; and Humira™ (adalimumab), a humanized anti-TNFα antibody.

Celiac Disease

Celiac disease (CD) is a chronic autoimmune disease that is HLA-DQ2/DQ8 haplotype restricted. Glutens, the major protein fraction of wheat, and related proteins in rye and barley are the triggering agents of the disease. Ingested gluten or its derivative fractions (gliadin and subunits) elicit a harmful T cell-mediated immune response after crossing the small bowel epithelial barrier, undergoing deamidation by tissue transglutaminase (tTG) and engaging class II MHC molecules.

While the earliest events leading to CD involve innate immune responses, evidence in the literature seems to suggest that a dysfunctional cross talk between innate and adaptive immunity is also an important pathogenic element in the autoimmune process of the disease. Under physiological circumstances, the intestinal epithelium, with its intact intercellular tight junctions (tj), serves as a key barrier to the passage of macromolecules such as gluten. When the integrity of the tj system is compromised, as in CD, a paracellular leak ("leaky gut") and an inappropriate immune response to environmental antigens (i.e., gluten) may develop.

In celiac intestinal tissues and in in vitro, ex vivo, and in vivo animal experiments, gluten/gliadin causes a rapid increase in permeability in normal and diseased states. Animal models likewise have demonstrated the association of gluten, increased paracellular permeability and other autoimmune diseases, including type 1 diabetes (T1D).

AT-1001 is an orally administered octapeptide (Gly Gly Val Leu Val Gln Pro Gly (SEQ ID NO:1), that appears to inhibit gliadin-induced TJ disassembly and prevent the associated increase in paracellular permeability. Experiments with ex vivo human tissue and in mice demonstrate that AT-1001 blocks the peak of F-actin increment induced by gliadin and inhibits gliadin induced reduction in intestinal Rt (resistance).

There is a continuing need in the art for methods to treat inflammatory and autoimmune diseases as well as diseases associated with biological barrier dysfunction more effectively and to discover or identify drugs which are suitable for treating inflammatory and autoimmune diseases as well as diseases associated with biological barrier dysfunction.

SUMMARY OF THE INVENTION

One object of the present invention is to inhibit increased permeability of biological barriers in response to secreted signals.

Another object of the present invention is to provide compounds that inhibit secretion of signals that cause increased permeability of biological barriers.

In particular embodiments the present invention provides compounds that inhibit the secretion of signals that cause increased permeability of biological barriers, wherein the signals are secreted in response to exposure of lymphocytes to lipopolysaccharide (LPS). In other particular embodiments the present invention provides compounds that inhibit the secretion of signals that cause increased permeability of biological bathers, wherein the signals are secreted in response to exposure of lymphocytes to pepsin/trypsin treated gliadin (PTG).

Another object of the present invention is to provide pharmaceutical compositions that inhibit secretion of signals that cause increased permeability of biological barriers.

In particular embodiments the present invention provides pharmaceutical compositions that inhibit the secretion of signals that cause increased permeability of biological barriers, wherein the signals are secreted in response to exposure of lymphocytes to lipopolysaccharide (LPS). In other particular embodiments the present invention provides pharmaceutical compositions that inhibit the secretion of signals that cause increased permeability of biological barriers, wherein the signals are secreted in response to exposure of lymphocytes to pepsin/trypsin treated gliadin (PTG).

Another object of the present invention is to provide methods of treating a patient showing an increased secretion of signals that cause increased permeability of biological bathers.

In particular embodiments the present invention provides methods of treating a patient showing an increased secretion of signals that cause increased permeability of biological bathers, wherein the signals are secreted in response to exposure of lymphocytes to lipopolysaccharide (LPS). In other particular embodiments the present invention provides methods of treating a patient showing an increased secretion of signals that cause increased permeability of biological barriers, wherein the signals are secreted in response to exposure of lymphocytes to pepsin/trypsin treated gliadin (PTG).

In certain embodiments, the invention provides a method of treating a patient with an autoimmune or inflammation-associated disease. The disease is selected from the group consisting of inflammatory bowel disease, including Crohn's disease and ulcerative colitis, necrotizing enterocolitis, type 1 diabetes, celiac disease, autoimmune hepatitis, multiple sclerosis, autism, dermatitis herpetiformis, IgA nephropathy, primary biliary chirrosis, rheumatoid arthritis, systemic lupus erythematosus, Grave's disease, Hashimoto's disease, and depression. A compound that inhibits the production, release and/or the biological effects of TNFα is administered to the patient.

Another object of the present invention is to provide methods to inhibit paracellular passage of gluten derived peptides across an epithelial barrier. Such methods comprise contacting the epithelial barrier with one or more peptide permeability inhibitors. Peptide permeability inhibitors for use in methods of the invention may comprise a peptide of any length. Such peptide permeability inhibitors may comprise a peptide from three to ten amino acids in length. In some embodiments, a peptide permeability inhibitor of the invention may comprise, consist essentially of, or consist of a peptide that comprises, consists essentially of or consists of an amino acid sequence selected from the group consisting of SEQ ID NOs: 1-162. In some embodiments, a peptide permeability inhibitor of the invention may comprise, consist essentially of, or consist of a peptide that comprises, consists essentially of or consists of an amino acid sequence selected from the group consisting of SEQ ID NOs: 1-5, 10-17, 19-23, 27, 32, 34, 36, 48, 49, 55, 58, 67-77, 79-85, 87, 88, 91, 92, 94, 98-104, 106, 110, 111, 113-125, 127, 128, 147, 150, and 160-162. In some embodiments, the invention does not include SEQ ID NOs: 15, 24, and 25.

The present invention also provides novel methods to inhibit increased paracellular permeability associated with exposure of a biological barrier to gluten derived peptides. Such methods comprise contacting the epithelial barrier with one or more peptide permeability inhibitors. Peptide permeability inhibitors for use in methods of the invention may comprise a peptide of any length. Such peptide permeability inhibitors may comprise a peptide from three to ten amino acids in length. In some embodiments, a peptide permeability inhibitor of the invention may comprise, consist essentially of, or consist of a peptide that comprises, consists essentially of or consists of an amino acid sequence selected from the group consisting of SEQ ID NOs: 1-162. In some embodiments, a peptide permeability inhibitor of the invention may comprise, consist essentially of, or consist of a peptide that comprises, consists essentially of or consists of an amino acid sequence selected from the group consisting of of SEQ ID NOs: 1-5, 10-17, 19-23, 27, 32, 34, 36, 48, 49, 55, 58, 67-77, 79-85, 87, 88, 91, 92, 94, 98-104, 106, 110, 111, 113-125, 127, 128, 147, 150, and 160-162. In some embodiments, the invention does not include SEQ ID NOs: 15, 24, and 25.

The present invention also provides compositions, e.g., pharmaceutical compositions, comprising one or more peptide permeability inhibitors of the invention, useful to inhibit paracellular passage of gluten derived peptides across an epithelial barrier. Peptide permeability inhibitors for use in compositions of the invention may comprise a peptide of any length. In some embodiments, such peptide permeability inhibitors may comprise a peptide of between three to ten amino acids in length. Suitable peptide permeability inhibitors for use in the compositions of the invention include, but are not limited to, peptide permeability inhibitors that comprise, consist essentially of, or consist of an amino acid sequence selected from the group consisting of SEQ ID NOs: 1-162, In some embodiments, peptide permeability inhibitors for use in the compositions of the invention include, but are not limited to, peptide permeability inhibitors comprising peptides that comprise, consist essentially of, or consist of an amino acid sequence selected from the group consisting of of SEQ ID NOs: 1-5, 10-17, 19-23, 27, 32, 34, 36, 48, 49, 55, 58, 67-77, 79-85, 87, 88, 91, 92, 94, 98-104, 106, 110, 111, 113-125, 127, 128, 147, 150, and 160-162. In some embodiments, the invention does not include SEQ ID NOs: 15, 24, and 25.

Compositions of the invention, for example, pharmaceutical compositions, may be formulated for any type of delivery. For example, compositions of the invention may be formulated for intestinal delivery, e.g., may be delayed release compositions. Compositions of the invention may also be formulated for pulmonary delivery, oral delivery and/or transcutaneous delivery.

In one embodiment, the present invention provides a method of treating a disease in a subject in need thereof. Methods of the invention may comprise administering to the subject a pharmaceutical composition comprising one or more peptide permeability inhibitors of the invention. Methods of the invention may comprise administering to the subject a pharmaceutical composition comprising one or more peptide permeability inhibitors and one or more additional therapeutic agents. In one embodiment, the present invention provides a method of treating celiac disease in a subject in need thereof. In another embodiment, the present invention provides a method of treating necrotizing enterocolitis in a subject in need thereof. In another embodiment, the present invention provides a method of treating an excessive or undesirable immune response in a subject in need thereof. In another embodiment, the present invention provides a method of treating inflammation in a subject in need thereof. In specific embodiments, the present invention provides methods of treating inflammatory bowel disease in a subject in need thereof. Inflammatory bowel disease that can be treated using methods of the present invention may be Crohn's disease or ulcerative colitis.

In further embodiments the invention provides methods of treating an autoimmune or inflammation-associated disease in a patient in need of such treatment. The disease is selected from the group consisting of type 1 diabetes, celiac disease, autoimmune hepatitis, multiple sclerosis, autism, dermatitis herpetiformis, IgA nephropathy, primary biliary chirrosis, rheumatoid arthritis, systemic lupus erythematosus, Grave's disease, Hashimoto's disease, and depression.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE DRAWINGS

FIG. 8B shows the effects on CaCO2 cell permeability of 72 hours exposure to culture supernatants prepared from donor PBMCs (00065) followed by addition of peptide permeability inhibitor (SEQ ID NO:1) after 48 hours treatment. After formation of tight junctions CaCO2 cells were exposed basolaterally to PBMC supernatants as described above. Peptide permeability inhibitor (SEQ ID NO:1) was added apically to the cultures after 48 hours (day 2), and lucifer yellow permeability was measured after 72 hours (day 3). Apical addition of peptide permeability inhibitor (SEQ AD NO:1) on day 2 abolished baseline permeability to Lucifer yellow (control+AT-1001; and PBMC sup+ AT1001), and it significantly reduced permeability changes induced by LPS (PBMC-LPS+AT1001) or PTG treated PBMC supernatant (PBMC-PTG+AT1001).

DETAILED DESCRIPTION OF THE INVENTION

Figure 1:
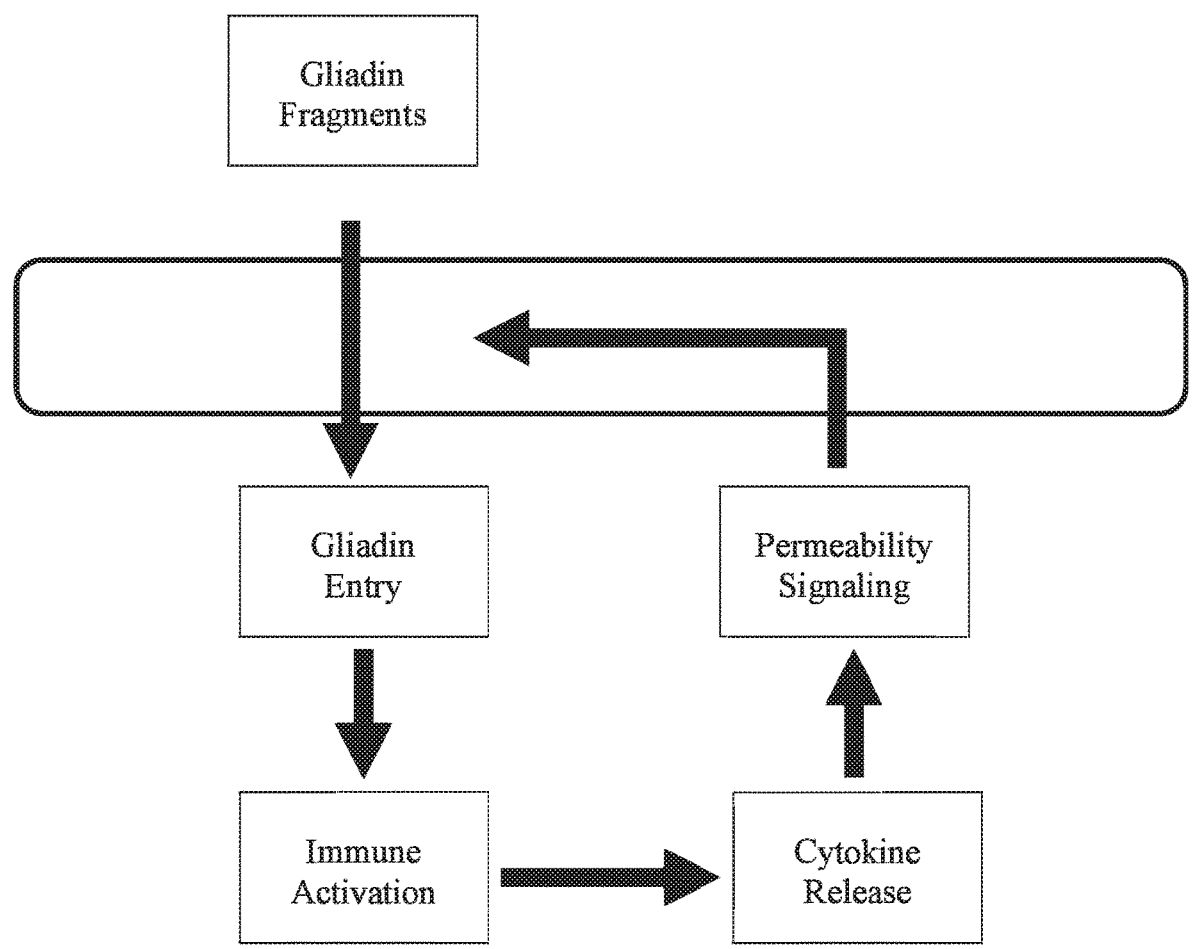
FIG. 1 is a schematic representation of the events leading to Celiac disease pathology. Gliadin fragments cross the intestinal epithelium and activate immune cells to produce soluble factors including cytokines that lead to increased permeability of the intestinal epithelium.
Figure 2:
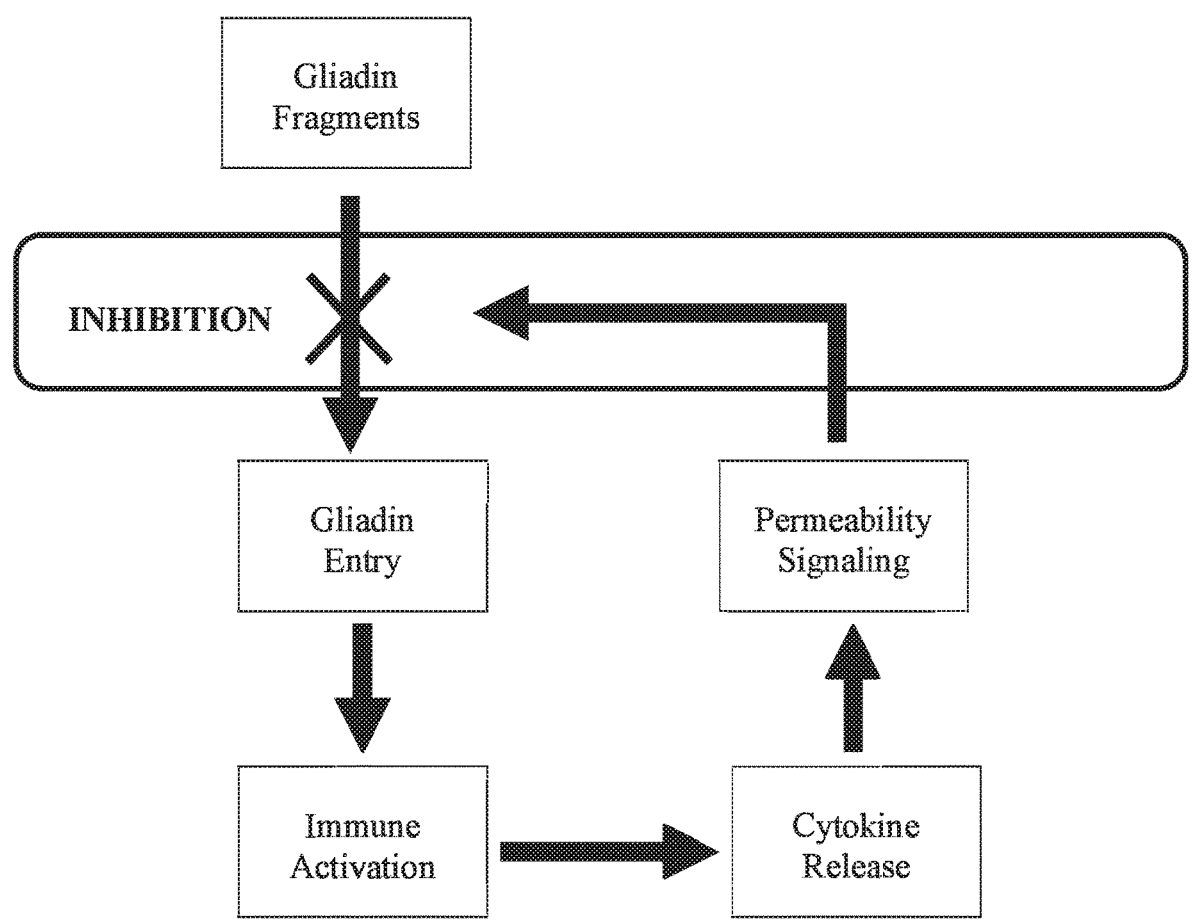
FIG. 2 is a schematic representation of the blockade of the gliadin fragment entry, the initial step leading to Celiac disease pathology. Gliadin fragments cross the intestinal epithelium and activate immune cells to produce soluble factors including cytokines that lead to increased permeability of the intestinal epithelium.
Figure 3:
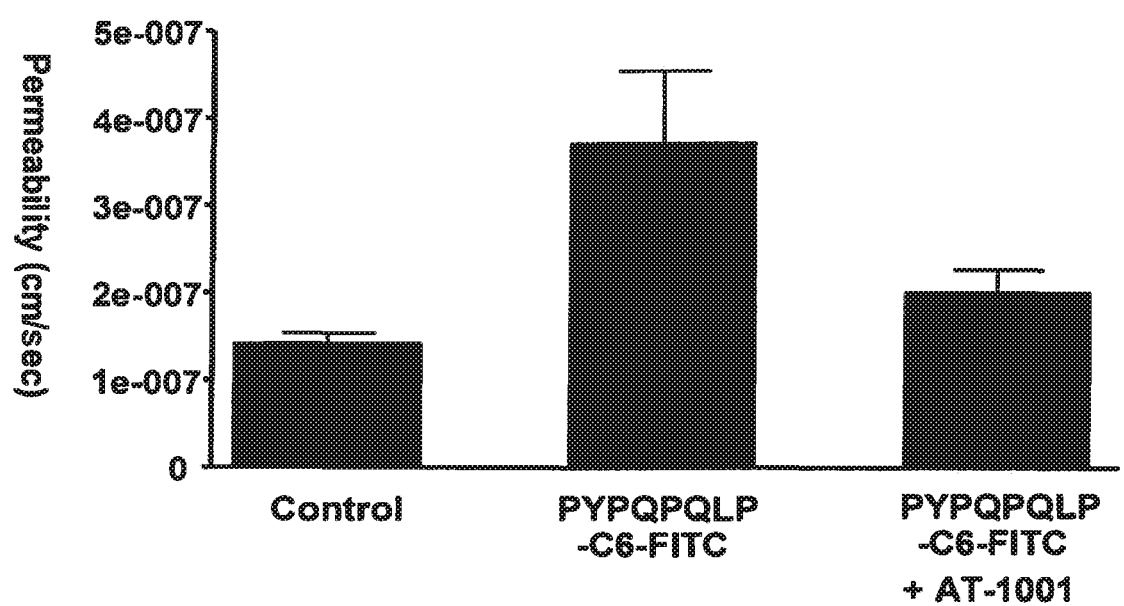
FIG. 3 shows the effect of a peptide permeability inhibitor (SEQ ID NO:1) on permeability of a CaCO2 cell monolayer to a gliadin fragment. Apical exposure of the monolayer to the gliadin peptide PYPQPQLPY (SEQ ID NO:163) lead to an increase in permeability to that peptide, which could be blocked by apical treatment with a peptide permeability inhibitor (SEQ ID NO:1).
Figure 4:
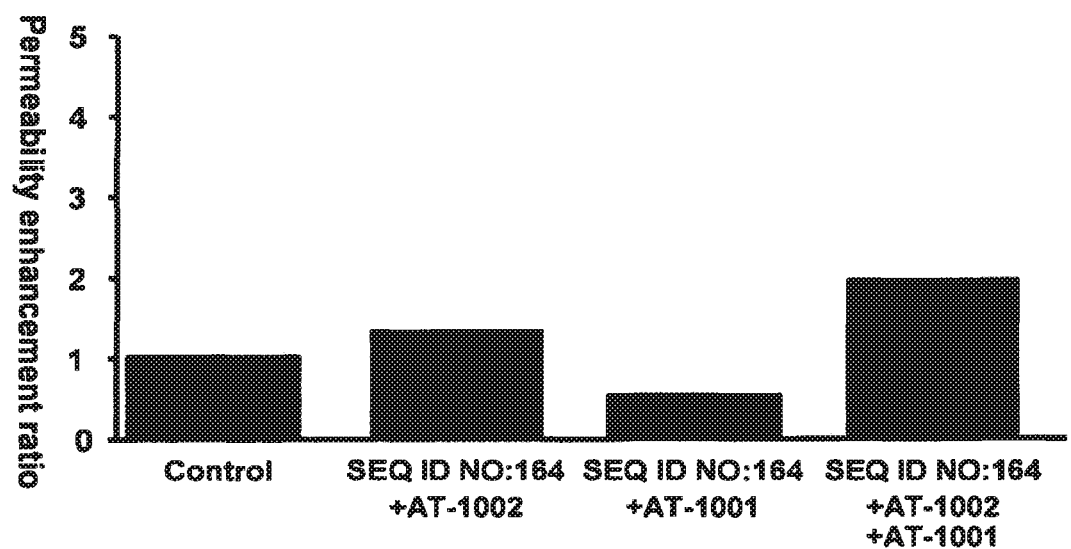
FIG. 4 shows the effect of a 13-mer gliadin peptide (LGQQQPFPPQQPY; SEQ ID NO:164) on permeability of a CaCO2 cell monolayer induced by a. Apical exposure of the monolayer to the gliadin peptide FITC-C6-PYPQPQLPY lead to an increase in permeability that could be blocked by treatment with a peptide permeability inhibitor (SEQ ID NO:1).
Figure 5A:
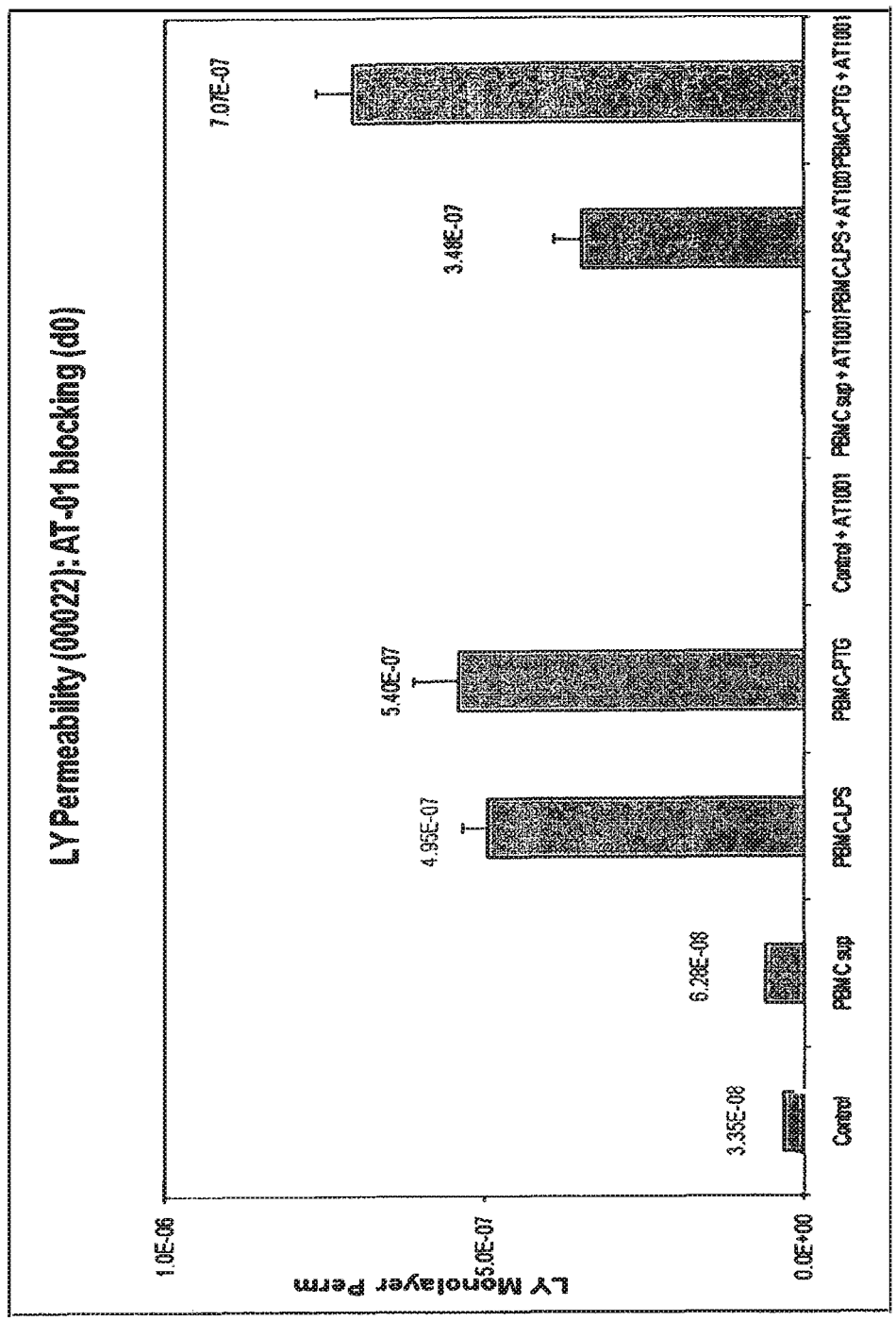
FIG. 5A shows the effects on CaCO2 cell permeability of 72 hours treatment with peptide permeability inhibitor (SEQ ID NO:1) in combination with culture supernatants prepared from donor PBMCs (00022). After formation of tight junctions CaCO2 cells were exposed basolaterally to control supernatant (control), untreated PBMC supernatant (PBMC sup), LPS treated PBMC supernatant (PBMC-LPS) and PTG treated PBMC supernatant (PBMC-PTG). Lucifer yellow permeability was measured after 72 hours (day 3). Simultaneous apical addition of peptide permeability inhibitor (SEQ ID NO:1) on day 0 abolished baseline permeability to Lucifer yellow (control+AT-1001; and PBMC sup+AT1001) but had no significant effect on permeability changes induced by LPS (PBMC-LPS+AT1001) or PTG treated PBMC supernatant (PBMC-PTG+AT1001).
Figure 5B:
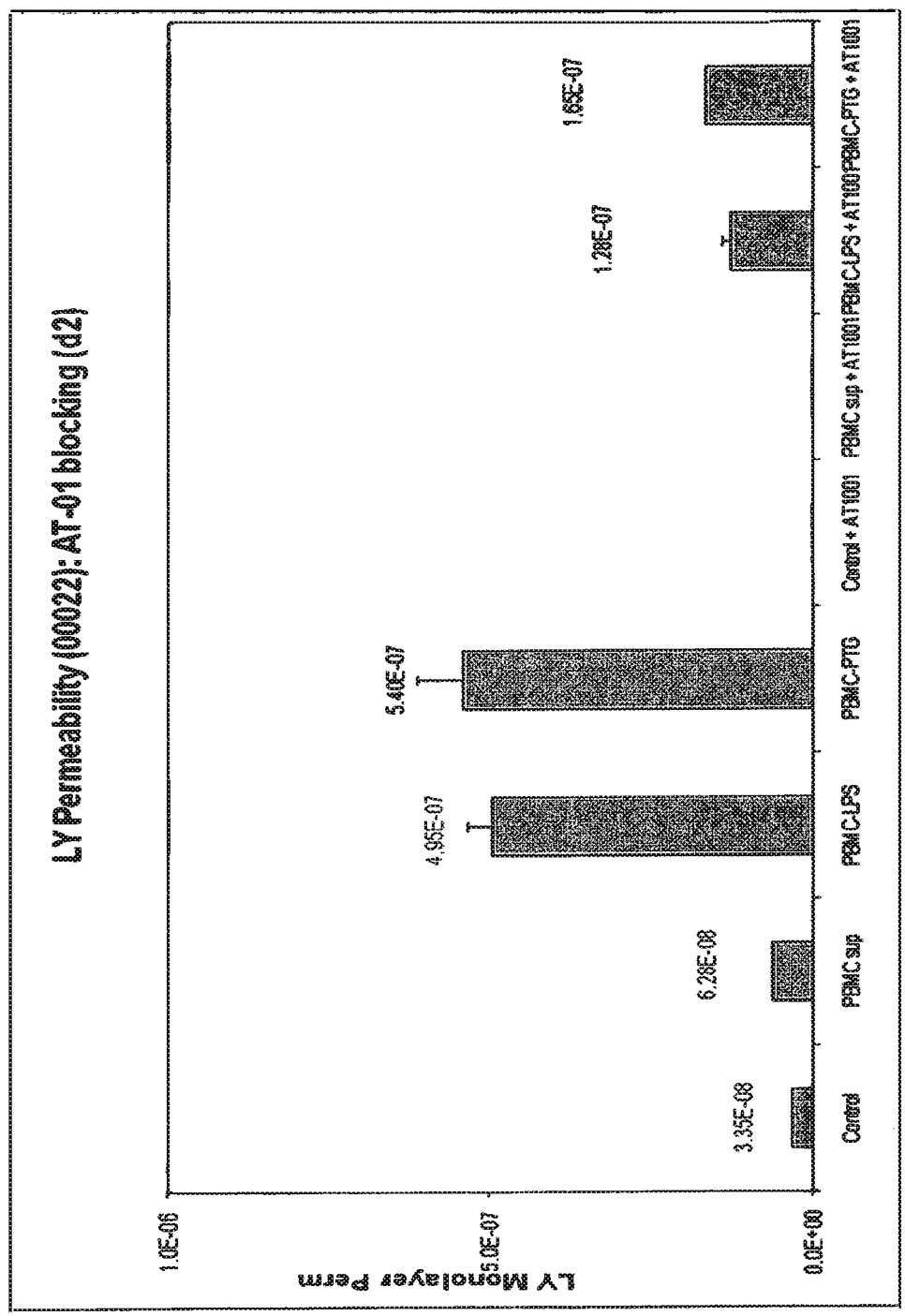
FIG. 5B shows the effects on CaCO2 cell permeability of 72 hours exposure to culture supernatants prepared from donor PBMCs (00022) followed by addition of peptide permeability inhibitor (SEQ ID NO:1) after 48 hours treatment. After formation of tight junctions CaCO2 cells were exposed basolaterally to PBMC supernatants as described above. Peptide permeability inhibitor (SEQ ID NO:1) was added apically to the cultures after 48 hours (day 2), and lucifer yellow permeability was measured after 72 hours (day 3). Apical addition of peptide permeability inhibitor (SEQ ID NO:1) on day 2 abolished baseline permeability to Lucifer yellow (control+AT-1001; and PBMC sup+AT1001), and it significantly reduced permeability changes induced by LPS (PBMC-LPS+AT1001) or PTG treated PBMC supernatant (PBMC-PTG+AT1001).
Figure 6A:
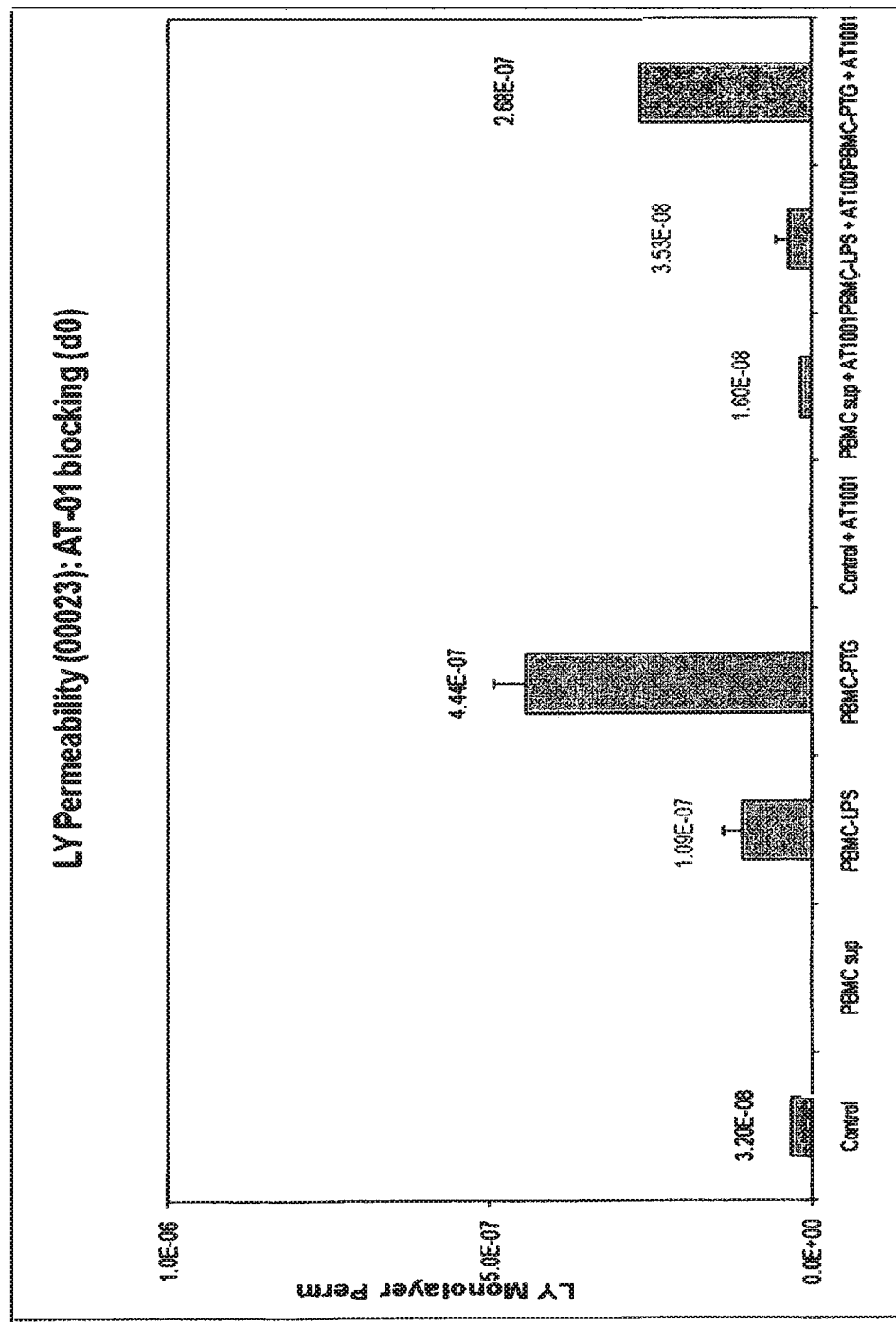
FIG. 6A shows the effects on CaCO2 cell permeability of 72 hours treatment with peptide permeability inhibitor (SEQ ID NO:1) in combination with culture supernatants prepared from donor PBMCs (00023). After formation of tight junctions CaCO2 cells were exposed basolaterally to control supernatant (control), untreated PBMC supernatant (PBMC sup), LPS treated PBMC supernatant (PBMC-LPS) and PTG treated PBMC supernatant (PBMC-PTG). Lucifer yellow permeability was measured after 72 hours (day 3). Simultaneous apical addition of peptide permeability inhibitor (SEQ ID NO:1) on day 0 abolished baseline permeability to Lucifer yellow (control+AT-1001; and PBMC sup+AT1001) but had no significant effect on permeability changes induced by LPS (PBMC-LPS+AT1001) or PTG treated PBMC supernatant (PBMC-PTG+AT1001).
Figure 6B:
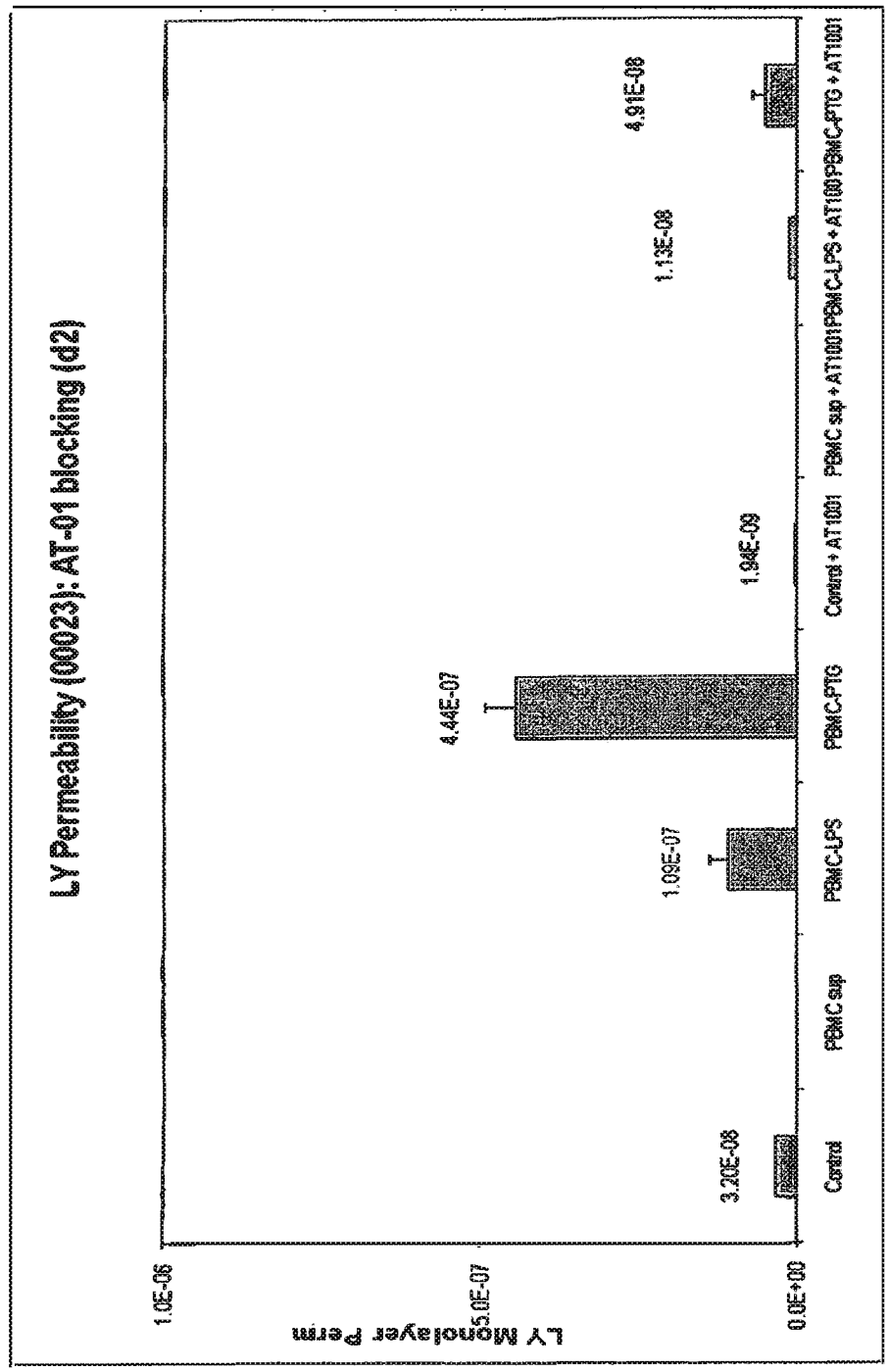
FIG. 6B shows the effects on CaCO2 cell permeability of 72 hours exposure to culture supernatants prepared from donor PBMCs (00023) followed by addition of peptide permeability inhibitor (SEQ ID NO:1) after 48 hours treatment. After formation of tight junctions CaCO2 cells were exposed basolaterally to PBMC supernatants as described above. Peptide permeability inhibitor (SEQ ID NO:1) was added apically to the cultures after 48 hours (day 2), and lucifer yellow permeability was measured after 72 hours (day 3). Apical addition of peptide permeability inhibitor (SEQ ID NO: 1) on day 2 abolished baseline permeability to Lucifer yellow (control+AT-1001; and PBMC sup+ AT1001), and it significantly reduced permeability changes induced by LPS (PBMC-LPS+AT1001) or PTG treated PBMC supernatant (PBMC-PTG+AT1001).
Figure 7A:
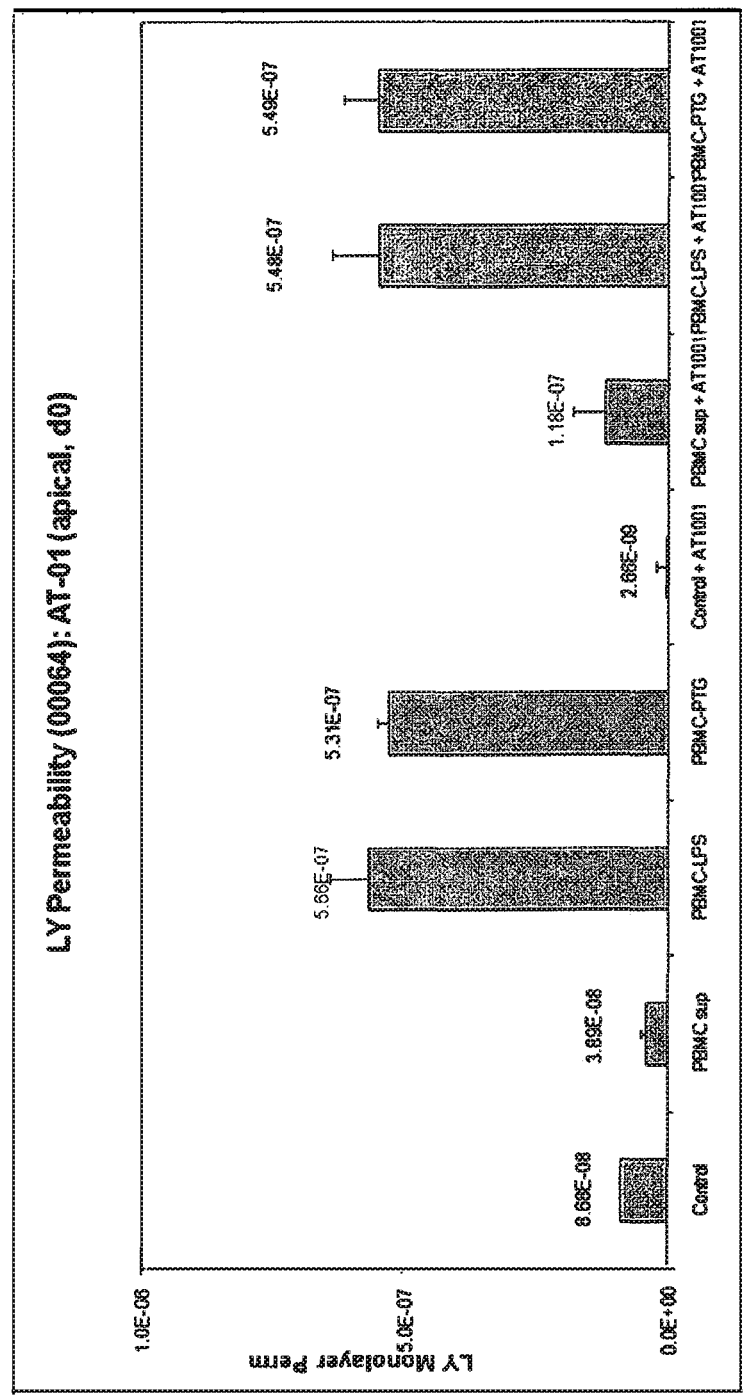
FIG. 7A shows the effects on CaCO2 cell permeability of 72 hours treatment with peptide permeability inhibitor (SEQ ID NO:1) in combination with culture supernatants prepared from donor PBMCs (00064). After formation of tight junctions CaCO2 cells were exposed basolaterally to control supernatant (control), untreated PBMC supernatant (PBMC sup), LPS treated PBMC supernatant (PBMC-LPS) and PTG treated PBMC supernatant (PBMC-PTG). Lucifer yellow permeability was measured after 72 hours (day 3). Simultaneous apical addition of peptide permeability inhibitor (SEQ ID NO:1) on day 0 abolished baseline permeability to Lucifer yellow (control+AT-1001; and PBMC sup+ AT1001) but had no significant effect on permeability changes induced by LPS (PBMC-LPS+AT1001) or PTG treated PBMC supernatant (PBMC-PTG+AT1001).
Figure 7B:
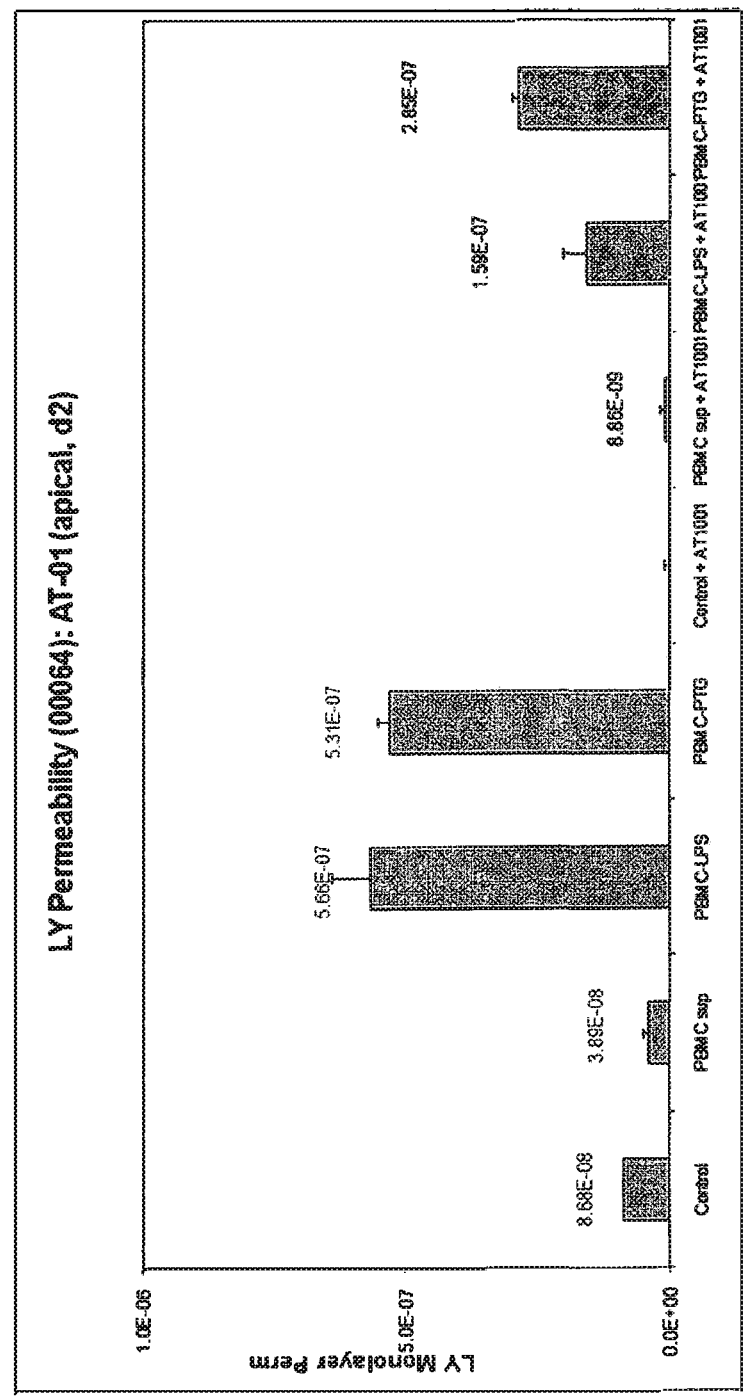
FIG. 7B shows the effects on CaCO2 cell permeability of 72 hours exposure to culture supernatants prepared from donor PBMCs (00064) followed by addition of peptide permeability inhibitor (SEQ ID NO:1) after 48 hours treatment. After formation of tight junctions CaCO2 cells were exposed basolaterally to PBMC supernatants as described above. Peptide permeability inhibitor (SEQ ID NO:1) was added apically to the cultures after 48 hours (day 2), and lucifer yellow permeability was measured after 72 hours (day 3). Apical addition of peptide permeability inhibitor (SEQ ID NO:1) on day 2 abolished baseline permeability to Lucifer yellow (control+AT-1001; and PBMC sup+ AT1001), and it significantly reduced permeability changes induced by LPS (PBMC-LPS+AT1001) or PTG treated PBMC supernatant (PBMC-PTG+AT1001).
Figure 8A:
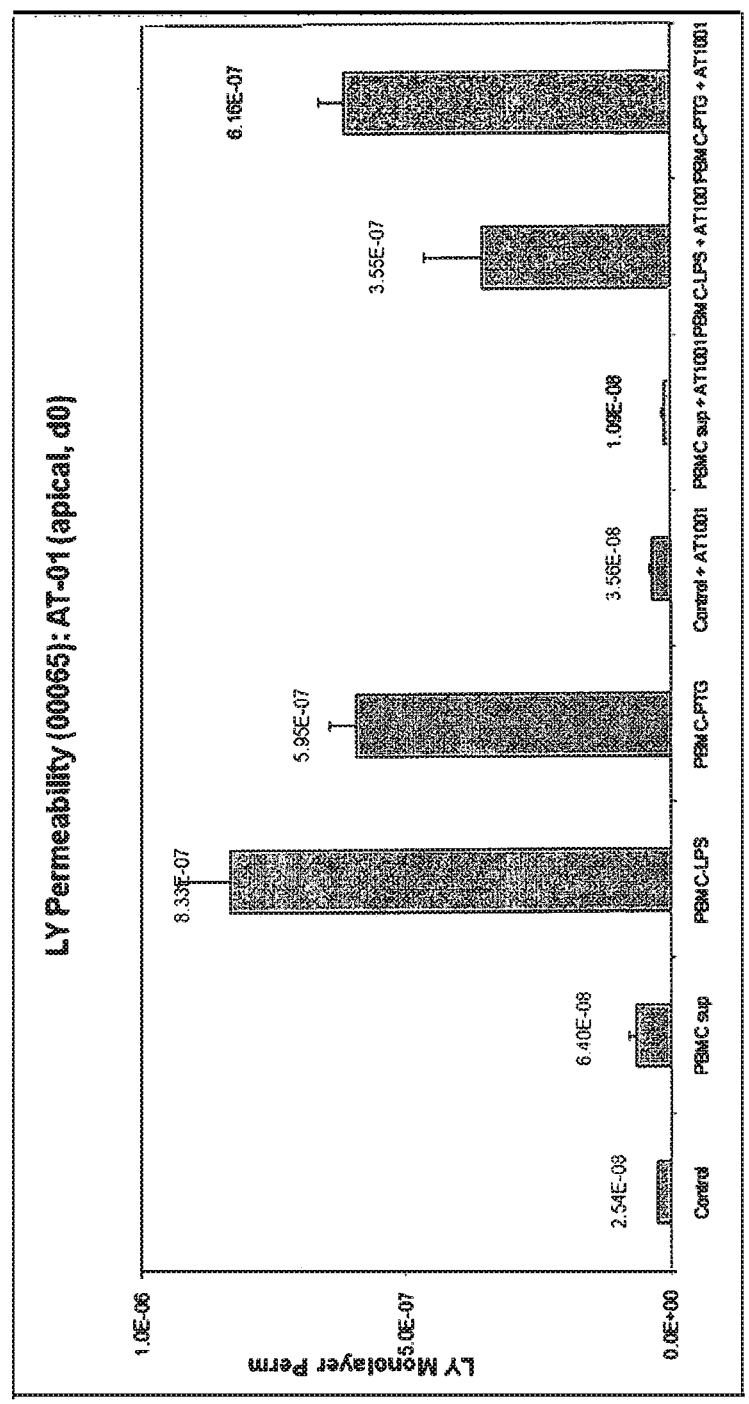
FIG. 8A shows the effects on CaCO2 cell permeability of 72 hours treatment with peptide permeability inhibitor (SEQ ID NO:1) in combination with culture supernatants prepared from donor PBMCs (00065). After formation of tight junctions CaCO2 cells were exposed basolaterally to control supernatant (control), untreated PBMC supernatant (PBMC sup), LPS treated PBMC supernatant (PBMC-LPS) and PTG treated PBMC supernatant (PBMC-PTG). Lucifer yellow permeability was measured after 72 hours (day 3). Simultaneous apical addition of peptide permeability inhibitor (SEQ ID NO:1) on day 0 abolished baseline permeability to Lucifer yellow (control+AT-1001; and PBMC sup+ AT1001) but had no significant effect on permeability changes induced by LPS (PBMC-LPS+AT1001) or PTG treated PBMC supernatant (PBMC-PTG+AT1001).

The inventors have discovered that peripheral blood mononuclear cells (PBMCs) secrete signals that increase epithelial monolayer permeability on response to stimulation with lipopolysaccharide (PLPS) and pepsin/trypsin treated gliadin (PTG). These secreted signals are present in PBMC culture supernatant, and they increase permeability of CaCO2 cell monolayers to Lucifer yellow when presented to the basolateral aspect of these cells. These permeability changes axe inhibited by treatment of the cells with peptide permeability inhibitors of the invention (FIGS. 5A, 5B, 6A, 6B, 7A, 7B, 8A and 8B). The inventors have also discovered that specific peptides within the PTG mixture are capable of crossing epithelial cell monolayers in vitro, and that this peptide specific mechanism can be inhibited by peptide permeability inhibitors of the invention (FIGS. 3 and 4).

Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, "biological effect" refers to a biochemical and physiological effect. Biological effect includes, for example, increases or decreases in the activity of the immune system and any of its components (including, for example, complement activation), increases or decreases in receptor binding and increases or decreases in subsequent downstream effector cellular constituents (including, for example, growth factor receptor and downstream effector cellular constituents), increases or decreases in cell signaling, increases or decreases in gene expression, increases or decreased in post-translation modification of proteins (including, for example, phosphorylation), and increases or decreases in protein activity.

As used herein, "modulate" and all its forms and tenses refer to either increasing or decreasing a particular biochemical or physiological effect.

As used herein, A "component of the immune system" or an "immune cell" refers to a component or cell of the immune system that is involved in enhancing, eliciting, or maintaining an immune response. The immune system responds to various foreign particles (including, for example, viruses, bacteria, and allergens) and non-foreign particles (including, for example, native endogenous proteins). An immune response includes, for example, antibody production, chemotaxis, phagocytosis, inflammation, complement activation, production of cytotoxic molecules (including, for example, reactive oxygen species and reactive nitrogen species), cell adhesion, cell infiltration, and production and recruitment of mediators of any of the foregoing or other immune responses. A component or cell of the immune system involved in enhancing, eliciting, or maintaining an immune response includes, for example, neutrophils, complement proteins (including, for example, C1q, C1r and C1s), eosinophils, basophils, lymphocytes (including for example, T cells (including, for example, cytotoxic T cells, memory T cells, helper T cells, regulatory T cells, natural killer T cells, and γδ T cells) and B cells (including, for example, plasma B cells, memory B cells, B-1 cells, and B-2 cells)), monocytes, macrophages, dendritic cells (DC), cell adhesion molecules (including, for example, ICAM and VCAM), myeloperoxidase, nitric oxide synthase, cyclooxygenase, and prostaglandin synthase.

As used herein, "treat" and all its forms and tenses refer to both therapeutic treatment and prophylactic or preventative treatment. Those in need of treatment include those already with the condition or disease as well as those in which the condition or disease is to be prevented.

Present Invention

The inventors have identified novel methods and compounds that inhibit increased permeability of biological barriers in response to stimuli that are known to induce secretion of pro-inflammatory cytokines. In specific embodiments the inventors have identified methods and compounds that inhibit increased permeability of biological barriers after stimulation by factors secreted by immune cells on exposure to LPS. In further specific embodiments the inventors have identified methods and compounds that inhibit increased permeability of biological barriers after stimulation by factors secreted by immune cells on exposure to PTG. Exemplary compounds of the invention that inhibit increased permeability of biological barriers are presented in Table 20.

The inventors have also identified novel methods and compounds that inhibit, reduce and/or prevent translocation of PTG-derived peptides across biological barriers. In specific embodiments the inventors have identified methods and compounds that inhibit, reduce and/or prevent translocation of the peptide comprising the amino acid sequence PYPQPQLPY (SEQ ID NO:163). Exemplary compounds of the invention that inhibit, reduce and/or prevent translocation of PTG-derived peptides across biological barriers are presented in Table 20.

Inhibitors of biological barrier permeability may be used in the practice of the present invention. Such permeability inhibitors may also be antagonists of mammalian tight junction opening. Antagonists of mammalian tight junction opening may also be used in the practice of the present invention. As used herein, permeability inhibitors prevent, inhibit or reduce the permeability of biological barriers to macromolecules including, for example, proteins, peptides and nucleic acids. For example, permeability inhibitors of the invention may comprise peptide permeability inhibitors. Examples of peptide permeability inhibitors that may be used in the practice of the present invention include, but are not limited to, peptides that comprise an amino acid sequence selected from the group consisting of consist of an amino acid sequence selected from the group consisting of SEQ ID NOs: 1-5, 10-17, 19-23, 27, 32, 34, 36, 48, 49, 55, 58, 67-77, 79-85, 87, 88, 91, 92, 94, 98-104, 106, 110, 111, 113-125, 127, 128, 147, 150, and 160-162.

Examples of peptide permeability inhibitors include, but are not limited to, peptides that consist of an amino acid sequence selected from the group consisting of SEQ ID NOs:1-162.

When the permeability inhibitor is a peptide, any length of peptide may be used. Generally, the size of the peptide antagonist will range from about 6 to about 100, from about 6 to about 90, from about 6 to about 80, from about 6 to about 70, from about 6 to about 60, from about 6 to about 50, from about 6 to about 40, from about 6 to about 30, from about 6 to about 25, from about 6 to about 20, from about 6 to about 15, from about 6 to about 14, from about 6 to about 13, from about 6 to about 12, from about 6 to about 11, from about 6 to about 10, from about 6 to about 9, or from about 6 to about 8 amino acids in length. Peptide antagonists of the invention may be from about 8 to about 100, from about 8 to about 90, from about 8 to about 80, from about 8 to about 70, from about 8 to about 60, from about 8 to about 50, from about 8 to about 40, from about 8 to about 30, from about 8 to about 25, from about 8 to about 20, from about 8 to about 15, from about 8 to about 14, from about 8 to about 13, from about 8 to about 12, from about 8 to about 11, or from about 8 to about 10 amino acids in length. Peptide antagonists of the invention may be from about 10 to about 100, from about 10 to about 90, from about 10 to about 80, from about 10 to about 70, from about 10 to about 60, from about 10 to about 50, from about 10 to about 40, from about 10 to about 30, from about 10 to about 25, from about 10 to about 20, from about 10 to about 15, from about 10 to about 14, from about 10 to about 13, or from about 10 to about 12 amino acids in length. Peptide antagonists of the invention may be from about 12 to about 100, from about 12 to about 90, from about 12 to about 80, from about 12 to about 70, from about 12 to about 60, from about 12 to about 50, from about 12 to about 40, from about 12 to about 30, from about 12 to about 25, from about 12 to about 20, from about 12 to about 15, or from about 12 to about 14 amino acids in length. Peptide antagonists of the invention may be from about 15 to about 100, from about 15 to about 90, from about 15 to about 80, from about 15 to about 70, from about 15 to about 60, from about 15 to about 50, from about 15 to about 40, from about 15 to about 30, from about 15 to about 25, from about 15 to about 20, from about 19 to about 15, from about 15 to about 18, or from about 17 to about 15 amino acids in length.

The peptide permeability inhibitors can be chemically synthesized and purified using well-known techniques, such as described in *High Performance Liquid Chromatography of Peptides and Proteins: Separation Analysis and Conformation,* Eds. Mant et al., C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

Compositions

Typically, compositions, such as pharmaceutical compositions, comprise one or more compounds of the invention, and optionally one or more additional active agents. Compounds of the invention may be present in an amount sufficient to inhibit the increased biological barrier permeability in a subject in need thereof. Compounds of the invention may be present in an amount sufficient to inhibit, reduce and/or prevent translocation of a gliadin-derived peptide across a biological barrier in a subject in need thereof. The amount of a compound of the invention employed in any given composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation.

Generally, a pharmaceutical composition of the invention will comprise an amount of a compound of the invention in the range of about 1 µg to about 1 g, preferably about 1 mg to about 1000 mg, from about 10 mg to about 100 mg, from about 10 mg to about 50 mg, or from about 10 mg to about 25 mg of the compound. As used herein, "about" used to modify a numerical value means within 10% of the value.

Compositions of the invention may comprise one or more compounds of the invention at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt %, from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition. As used herein, "about" used to modify a numerical value means within 10% of the value. Compositions of the invention may comprise one or more compounds of the invention at a level of about 0.1 wt %, about 0.2 wt %, about 0.3 wt %, about 0.4 wt %, about 0.5 wt %, about 0.6 wt %, about 0.7 wt %, about 0.8 wt %, or about 0.9 wt % based on the total weight of the composition.

Compositions of the invention may comprise one or more compounds of the invention at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. As used herein, "about" used to modify a numerical value means within 10% of the value. Compositions of the invention may comprise one or more compounds of the invention at a level of about 1 wt %, about 2 wt %, about 3 wt %, about 4 wt %, about 5 wt %, about 6 wt %, about 7 wt %, about 8 wt %, or about 9 wt % based on the total weight of the composition.

Compositions of the invention, for example, pharmaceutical compositions comprising one or more compounds of the invention and one or more additional active agents, may be formulated for pulmonary delivery (e.g., may be pulmonary dosage forms). Typically such compositions may be provided as pharmaceutical aerosols, e.g., solution aerosols or powder aerosols. Those of skill in the art are aware of many different methods and devices for the formation of pharmaceutical aerosols, for example, those disclosed by Sciarra and Sciarra, *Aerosols, in Remington: The Science and Practice of Pharmacy*, 20th Ed., Chapter 50, Gennaro et al. Eds., Lippincott, Williams and Wilkins Publishing Co., (2000).

In one embodiment, the dosage forms are in the form of a powder aerosol (i.e, comprise particles). These are particularly suitable for use in inhalation delivery systems. Powders may comprise particles of any size suitable for administration to the lung.

Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. In one embodiment, a powder formulation may comprise lactose as a carrier.

Powder formulations may be contained in any container known to those in the art. Containers may be capsules of, for example, gelatin or plastic, or in blisters (e.g. of aluminum or plastic), for use in a dry powder inhalation device. In some embodiments, the total weight of the formulation in the container may be from about 5 mg to about 50 mg. In other embodiments, powder formulations may be contained in a reservoir in a multi-dose dry powder inhalation device adapted to deliver a suitable amount per actuation.

Powder formulations typically comprise small particles. Suitable particles can be prepared using any means known in the art, for example, by grinding in an airjet mill, ball mill or vibrator mill, sieving, microprecipitation, spray-drying, lyophilisation or controlled crystallisation. Typically, particles will be about 10 microns or less in diameter. Particles for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. As used herein, "about" used to modify a numerical value means within 10% of the value. In some embodiments, particles for use in the invention may be about 1 micron, about 2 microns, about 3 microns, about 4 microns, about 5 microns, about 6 microns, about 7 microns, about 8 microns, about 9 microns, or about 10 microns in diameter.

In one embodiment, the dosage forms are in the form of a solution aerosol (i.e., comprise droplets). Typically, droplets will be about 10 microns or less in diameter. Droplets for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. As used herein, "about" used to modify a numerical value means within 10% of the value. In some embodiments, particles and/or droplets for use in the invention may be about 1 micron, about 2 microns, about 3 microns, about 4 microns, about 5 microns, about 6 microns, about 7 microns, about 8 microns, about 9 microns, or about 10 microns in diameter.

The compositions of the invention may be formulated for enteric delivery, for example, may comprise one or more coatings including, for example, a delayed release coating containing one or more enteric agents. A delayed release coating is typically substantially stable in gastric fluid and substantially unstable (e.g., dissolves rapidly or is physically unstable) in intestinal fluid, thus providing for substantial release of the compounds of the invention and/or additional active agent from the composition in the duodenum or the jejunum.

The term "stable in gastric fluid" refers to a composition that releases 30% or less by weight of the total compound of the invention and/or additional active agent in the composition in gastric fluid with a pH of 5 or less, or simulated gastric fluid with a pH of 5 or less, in approximately sixty minutes. Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Compositions of the of the invention may release from about 0% to about 30%, from about 0% to about 25%, from about 0% to about 20%, from about 0% to about 15%, from about 0% to about 10%, from about 5% to about 30%, from about 5% to about 25%, from about 5% to about 20%, from about 5% to about 15%, from about 5% to about 10% by weight of the total compound of the invention and/or additional active agent in the composition in gastric fluid with a pH of 5 or less, or simulated gastric fluid with a pH of 5 or less, in approximately sixty minutes. As used herein, "about" used to modify a numerical value means within 10% of the value. Compositions of the invention may release about 1%, about 2%, about 3%, about 4%, about 5%, about 6%, about 7%, about 8%, about 9%, or about 10% by weight of the total compound of the invention in the composition in gastric fluid with a pH of 5 or less, or simulated gastric fluid with a pH of 5 or less, in approximately sixty minutes.

The term "unstable in intestinal fluid" refers to a composition that releases 70% or more by weight of the total amount of the compound of the invention and/or additional active agent in the composition in intestinal fluid or simulated intestinal fluid in approximately sixty minutes. The tem "unstable in near neutral to alkaline environments" refers to a composition that releases 70% or more by weight of the total amount of the compound of the invention and/or additional active agent in the composition in intestinal fluid with a pH of 5 or greater, or simulated intestinal fluid with a pH of 5 or greater, in approximately ninety minutes. For example, a composition that is unstable in near neutral or alkaline environments may release 70% or more by weight of a compound of the invention and/or additional active agent in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, from about 10 minutes to about 90 minutes, from about 15 minutes to about 90 minutes, from about 20 minutes to about 90 minutes, from about 25 minutes to about 90 minutes, from about 30 minutes to about 90 minutes, from about 5 minutes to about 60 minutes, from about 10 minutes to about 60 minutes, from about 15 minutes to about 60 minutes, from about 20 minutes to about 60 minutes, from about 25 minutes to about 60 minutes, or from about 30 minutes to about 60 minutes. As used herein, "about" used to modify a numerical value means within 10% of the value.

Compositions of the invention may be formulated for transcutaneous delivery (e.g., may be transcutaneous dosage forms). Typically such compositions may be provided as topical solutions and/or gels. Those of skill in the art are aware of many different methods and devices for the formation of topical medications, for example, those disclosed by Block, *Medicated Topicals,* in *Remington: The Science and Practice of Pharmacy,* 20th Ed., Chapter 44, Gennaro et al. Eds., Lippincott, Williams and Wilkins Publishing Co. (2000).

Various delivery systems are known and can be used to administer a compound of the invention, e.g., encapsulation in liposomes, microparticles, microcapsules, recombinant cells capable of expressing the compound, receptor-mediated endocytosis etc. Methods of introduction include but are not limited to intradermal, intramuscular, intraperitoneal, intravenous, subcutaneous, intranasal, epidural, and oral mutes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable mute, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not adsorb.

In another embodiment, the compound or composition can be delivered in a vesicle, in particular a liposome.

In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose. Other controlled release systems are well known in the art.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil; sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline, Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention that will be effective in the treatment, inhibition and/or prevention of a disease or disorder associated with increased biological barrier permeability can be determined by standard clinical techniques. The amount of the compound of the invention that will be effective in the treatment, inhibition and/or prevention of a disease or disorder associated with translocation of one or more gliadin-derived peptides across a biological barrier can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Additional Active Agents

In addition to one or more compounds of the invention, compositions of the invention may further comprise one or more additional active agents, e.g., therapeutic agents, immunogenic agents and/or imaging agents.

Additional therapeutic agents that can be used in the compositions of the invention include agents that act on any organ of the body, such as heart, brain, intestine, or kidneys. Suitable additional therapeutic agents include, but are not limited to, glucose metabolism agents (e.g., insulin), antibiotics, antineoplastics, antihypertensives, antiepileptics, central nervous system agents, anti-inflammatory agents and immune system suppressants.

Additional therapeutic agents that can be used in the compositions of the invention include immunosuppressive agents. Such immunosuppressants used in the method and composition of the invention can be any agent which tends to attenuate the activity of the humoral or cellular immune systems. In particular, in one aspect the invention comprises compositions wherein the immunosuppressant is selected from the group consisting of cyclosporin A, FK506, prednisone, methylprednisolone, cyclophosphamide, thalidomide, azathioprine, and daclizumab, physalin B, physalin F, physalin G, seco-steroids purified from Physalis angulata L., 15-deoxyspergualin (DSG, 15-dos), MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliooxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane (SKF 105685), paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea, and combinations thereof. In one more particular aspect, the immunosuppressant is cyclosporin A.

Furthermore, the additional therapeutic agent can be selected from the group consisting of a chemotherapeutic, a gene therapy vector, a growth factor, a contrast agent, an angiogenesis factor, a radionuclide, an anti-infection agent, an anti-tumor compound, a receptor-bound agent, a hormone, a steroid, a protein, a complexing agent, a polymer, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antihypertensive agent, an antimicrobial agent, an antibiotic, a glycoprotein IIb/IIIa inhibitor, an inhibitor of surface glycoprotein receptors, an antiplatelet agent, an antimitotic, a microtubule inhibitor, a retinoid, an antisecretory agent, an actin inhibitor, a remodeling inhibitor, an antisense nucleotide, an agent for molecular genetic intervention, an antimetabolite, an antiproliferative agent, an anti-cancer agent, a dexamethasone derivative, an anti-inflammatory steroid, a non-steroidal anti-inflammatory agent, an immunosuppressive agent, a PDGF antagonist, a growth hormone antagonist, a growth factor antibody, an anti-growth factor antibody, a growth factor antagonist, a dopamine agonist, a radiotherapeutic agent, an iodine-containing compound, a barium-containing compound, a heavy metal functioning as a radiopaque agent, a peptide, a protein, an enzyme, an extracellular matrix component, a cellular component, an angiotensin converting enzyme inhibitor, a 21-aminosteroid, a free radical scavenger, an iron chelator, an antioxidant, a sex hormone, an antipolymerase, an antiviral agent, an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin or other antibody targeted therapy agents, gene therapy agents, a prodrug, a photodynamic therapy agent, and an agent for treating benign prostatic hyperplasia (BHP), a $^{14}$C-, $^{3}$H-, $^{131}$I-, $^{32}$P- or $^{30}$S-radiolabelled form or other radiolabelled form of any of the foregoing, and combinations thereof.

More particularly, the additional therapeutic agent can be selected from the group consisting of parathyroid hormone, heparin, human growth hormone, covalent heparin, hirudin, hirulog, argatroban, D-phenylalanyl-L-poly-L-arginyl chloromethyl ketone, urokinase, streptokinase, nitric oxide, triclopidine, aspirin, colchicine, dimethyl sulfoxide, cytochalasin, deoxyribonucleic acid, methotrexate, tamoxifen citrate, dexamethasone, dexamethasone sodium phosphate, dexamethasone acetate, cyclosporin, trapidal, angiopeptin, angiogenin, dopamine, $^{60}$Co, $^{192}$Ir, $^{32}$P, $^{111}$In, $^{90}$Y, $^{99m}$Tc, pergolide mesylate, bromocriptine mesylate, gold, tantalum, platinum, tungsten, captopril, enalapril, ascorbic acid, α-tocopherol, superoxide dismutase, deferoxamine, estrogen, azidothymidine (AZT), acyclovir, famciclovir, rimantadine hydrochloride, ganciclovir sodium, 5-aminolevulinic acid, meta-tetrahydroxyphenylchlorin, hexadacafluoro zinc phthalocyanine, tetramethyl hematoporphyrin, and rhodamine 123, and combinations thereof.

Compositions of the invention may comprise one or more immunogenic agents, for example, antigens. Examples of antigens that can be used in the compositions of the invention (e.g., immunogenic and/or vaccine compositions) include peptides, proteins, microorganisms (e.g., attenuated and/or recombinant microorganisms), cells (e.g., cancer cells and/or recombinant cells) and viruses (e.g., attenuated and/or recombinant viruses). Examples of peptide antigens include the B subunit of the heat-labile enterotoxin of enterotoxigenic *E. coli*, the B subunit of cholera toxin, capsular antigens of enteric pathogens, fimbriac or pili of enteric pathogens, HIV surface antigens, cancer antigens (e.g., cancer cells comprising antigens, isolated antigens, etc.), dust allergens, and acari allergens. Other immunogenic compounds as are known in the art can also be used.

Examples of attenuated microorganisms and viruses that can be used in the compositions of the invention (e.g., vaccine compositions) include those of enterotoxigenic *Escherichia coli*, enteropathogenic *Escherichia coli*, *Vibrio cholerae*, *Shigella flexneri*, *Salmonella typhi* and rotavirus (Fasano et al, In: Le Vaccinazioni in Pediatria, Eds. Vierucci et al, CSH, Milan, pages 109-121 (1991); Guandalini et al, In: Management of Digestive and Liver Disorders in Infants and Children, Elsevior, Eds. Butz et al, Amsterdam, Chapter 25 (1993); Levine et al, Sem. Fed. Infect. Dis., 5.243-250 (1994); and Kaper et al, Clin. Micrbiol. Rev., 8:48-86 (1995), each of which is incorporated by reference herein in its entirety).

Any antigen capable of inducing a protective immune response may be used in the vaccine compositions of the invention. Examples of suitable antigens include, but are not limited to, measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

Compositions of the invention may further comprise one or more protease inhibitors. Any protease inhibitor can be used, including, but not limited to, a proteinase, peptidase, endopeptidase, or exopeptidase inhibitor. A cocktail of inhibitors can also be used. Alternatively, the protease inhibitors can be selected from the group consisting of bestatin, L-trans-3-carboxyoxiran-2-carbonyl-L-leucylagmatine, ethylenediaminetetra-acetic acid (EDTA), phenylmethylsulfonylfluoride (PMSF), aprotinin, amyloid protein precursor (APP), amyloid beta precursor protein, α1-proteinase inhibitor, collagen VI, bovine pancreatic trypsin inhibitor (BPTI), 4-(2-aminoethyl)-benzenesulfonyl fluoride (AEBSF), antipain, benzamidine, chymostatin, ε-aminocaproate, N-ethylmaleimide, leupeptin, pepstatin A, phosphoramidon, and combinations thereof. Novel protease inhibitors can also be used. indeed, protease inhibitors can be specifically designed or selected to decrease the proteolysis of the tight junction agonist and/or the therapeutic agent.

Compositions of the invention may also comprise one or more pharmaceutically acceptable excipients. Suitable excipients include, but are not limited to, buffers, buffer salts, bulking agents, salts, surface active agents, acids, bases, sugars, binders, and the like.

Methods of Treatment

Compounds and pharmaceutical compositions of the invention can be used for treating, ameliorating, and/or preventing a disease. Any disease may be treated using the compositions of the invention by selection of an appropriate active agent, e.g., therapeutic and/or immunogenic agent. In one embodiment, the present invention provides a method of treating diabetes response in a subject (e.g., a mammal such as a human) by administering a composition comprising one or more compounds of the invention together with one or more insulins and/or derivatives thereof. In another embodiment, the invention provides a method of suppressing an excessive or undesirable immune response in a subject (e.g., a mammal such as a human) by administering a composition comprising one or more compounds of the invention together with one or more immune-suppressive drugs that may include, for example, cyclosporin A.

Examples of diseases that can be treated using the compositions of the invention include, but are not limited to, cancer, autoimmune diseases, vascular disease, bacterial infections, gastritis, gastric cancer, collagenous colitis, inflammatory bowel disease, necrotizing enterocolitis, osteoporosis, systemic lupus erythematosus, food allergy, asthma, celiac disease and irritable bowel syndrome. For example, to treat inflammatory bowel disease, a composition comprising one or more compounds of the invention may be administered to the subject (e.g., a mammal such as a human) in need thereof.

In another example, to treat cancer of the colon or rectal area, a composition comprising a therapeutically effective amount of Erbitux® (Cetuximab) together with a GM-CSF and/or IL-16 inhibiting amount of one or more compounds of the invention may be administered to the subject (e.g., a mammal such as a human) in need thereof. In another example, to treat breast cancer, a composition comprising a therapeutically effective amount of Herceptin® (Trastuzumab) together with a GM-CSF and/or IL-16 inhibiting amount of one or more compounds of the invention may be administered to the subject (e.g., a mammal such as a human) in need thereof. In another example, to treat various types of cancer, a composition comprising a therapeutically effective amount of Avastin® (Bevacizumab) together with a GM-CSF and/or IL-16 inhibiting amount of one or more compounds of the invention may be administered to the subject (e.g., a mammal such as a human) in need thereof. Another example involves treatment of osteoporosis by administration of a composition comprising one or more compounds of the invention together with a therapeutically effective amount of Fosamax® (Alendronate) to the subject in need thereof. Another example involves treatment of transplant rejection by administration of a composition comprising one or compounds of the invention together with a therapeutically effective amount of Cyclosporin A to the subject in need thereof. Another example involves treatment of anemia by administration of a composition comprising one or more compounds of the invention together with a therapeutically effective amount of erythropoietin to the subject in need thereof. Another example involves treatment of hemophilia by administration of a composition comprising one or more compounds of the invention together with a therapeutically effective amount of Factor VIII to the subject in need thereof.

In some embodiments, compositions of the invention (e.g., pharmaceutical compositions) may be given repeatedly over a protracted period, i.e., may be chronically administered. Typically, compositions may be administered one or more times each day in an amount suitable to prevent, reduce the likelihood of an attack of, or reduce the severity of an attack of the underlying disease condition (e.g., diabetes, cancer, transplant rejection, etc). Such compositions may be administered chronically, for example, one or more times daily over a plurality of days.

In some embodiments, compositions of the invention (e.g., pharmaceutical compositions) may be used to treat acute attacks of the underlying disease (e.g., diabetes, cancer, transplant rejection, etc). Typically, embodiments of this type will require administration of the compositions of the invention to a subject undergoing an attack in an amount suitable to reduce the severity of the attack. One or more administrations may be used.

In some embodiments, compounds of the invention may be used in the manufacture of compositions and pharmaceutical compositions for use in the methods described above.

While the invention has been described with reference to certain particular embodiments thereof, those skilled in the art will appreciate that various modifications may be made without departing from the spirit and scope of the invention. The scope of the appended claims is not to be limited to the specific embodiments described.

Methods of Screening

Screening for inhibitors of gliadin-derived peptide translocation across biological barriers can be accomplished by a variety of techniques. Likewise, screening for inhibitors of PTG-induced factors that increase biological barrier permeability can be accomplished by a variety of techniques. Gliadin-derived peptide binding to test compounds (inhibitor candidates) can be directly measured, or inhibition of binding of gliadin-derived peptides to a cell preparation can be measured. Gliadin-derived peptides can be labeled to facilitate measurement of binding. Assays may be in cell-free systems or in cell-based systems. Any binding assay format can be used, including formats where the receptor is attached to a solid support, either directly or indirectly.

Test compounds which can be tested are any compounds. The compounds may be tested as single compounds or in combinations of compounds. The compounds may be structurally identified or of unknown structure. The compounds may be novel or previously known. The compounds may be natural products or synthetic.

According to one embodiment of the invention the test compounds are fragments of gliadin. Gliadin is a family of proteins which are produced by wheat and other grains. Examples of gliadins are gliadin alpha, gamma, and omega. Gliadins are the aqueous alcohol-soluble storage proteins in the seed. There is great heterogeneity even within a single class of gliadins. At least six, seven, eight, nine, ten, eleven, fifteen, twenty, thirty, thirty-five, fifty, or seventy-five amino acid residues may be used in fragments of gliadin as test compounds. Fragments include any molecule which is less than full length. Fragments may be, e.g., synthesized or the result of proteolytic degradation. The following tables provide the sequences of a representative number of gliadins.

TABLE 1

Amino acid sequence of alpha-gliadin from *Triticum aestivum* (NCBI accession no. CAB76964, (SEQ ID NO: 165))

```
  1  mvrvpvpqlq pqnpsqqqpq eqvplvqqqq fpgqqqpfpp qqpypqpqpf
 51  psqqpylqlq pfpqpqlpyp qpqlpypqpq lpypqpqpfr pqqpypqsqp
101  qysqpqqpis qqqqqqqqq qqkqqqqqqq qilqqilqqq lipcrdvvlq
151  qhsiaygssq vlqqstyqlv qqlccqqlwq ipeqsrcqai hnvvhaiilh
201  qqqqqqqqq qqpisqvsfq qpqqqypsgq gsfqpsqqnp qaqgsvqpqq
251  lpqfeeirnl aletlpamcn vyippyctia pvgifgtnyr
```

15

TABLE 2

Amino acid sequence of alpha-gliadin precursor from *Triticum turgidum* subsp. durum (NCBI accession no. CAI35909, (SEQ ID NO: 166))

```
  1  mktflilall aivattatta vrvpvpqlqr qnpsqqqpqe qvplvqqqqf
 51  lgqqqpfppq qpypqpqpfp sqqpylqlqp fpqpqlpysq pqpfrpqqpy
101  pqpqprysqp qqpisqqqqq qhqqhqqhhq eqqilqqilq qqlipcmdvv
151  lqqhniahrr sqvlqqstyq llgelccqhl wqipeqsqcq aihnvvhaii
201  phqqkqqqq pssqfsfqqp lqqyplgqgs frpsqqnpqa qgsvqpqqlp
251  qfeeirnlal qtlpamcnvy ippyctiapf gifgtn
```

TABLE 3

Amino acid sequence of alpha/beta-gliadin precursor from *Triticum aestivum* (NCBI accession no. AAA34280, (SEQ ID NO: 167))

```
  1  mktflilvll aivattatta vrfpvpqlqp qnpsqqqpqe qvplvqqqqf
 51  lgqqqpfppq qpypqpqpfp sqlpylqlqp fpqpqlpysq pqpfrpqqpy
101  pqpqpqysqp qqpisqqqqq qqqqqqqqq qqqilqqilq qqlipcmdvv
151  lqqhniahgr sqvlqqstyq llgelccqhl wqipeqsqcq aihnvvhaii
201  lhqqkqqqq pssqvsfqqp lqqyplgqgs frpsqqnpqa qgsvqpqqlp
251  qfeeirnlal qtlpamcnvy ippyctiapf gifgtn
```

TABLE 4

Amino acid sequence of Gamma-gliadin precursor from *Triticum aestivum* (NCBI accession no. P21292, (SEQ ID NO: 168))

```
  1  mktlliltil amattiatan mqvdpsgqvq wpqqqpfpqp qqpfcqqpqr
 51  tipqphqtfh hqpqqtfpqp qqtyphqpqq qfpqtqqpqq pfpqpqqtfp
101  qqpqlpfpqq pqqpfpqpqq pqqpfpqsqq pqqpfpqpqq qfpqpqqpqq
151  sfpqqqpai qsflqqqmnp cknfllqqcn hvslvsslvs iilprsdcqv
201  mqqqccqqla qipqqlqcaa ihsvahsiim qqeqqqgvpi lrplfglaqg
```

TABLE 4-continued

Amino acid sequence of Gamma-gliadin precursor from
Triticum aestivum (NCBI accession no. P21292,
(SEQ ID NO: 168))

251 lgiiqpqqpa qlegirslvl ktlptmcnvy vppdcstinv pyanidagig 301 gq

TABLE 5

Amino acid sequence of Gamma-gliadin B precursor from
Triticum aestivum (NCBI accession no. P06659,
(SEQ ID NO: 169))

1 mktlliltil amaitiatan mqadpsgqvq wpqqqpflqp hqpfsqqpqq 51 ifpqpqqtfp hqpqqqfpqp qqpqqqflqp rqpfpqqpqq pypqqpqqpf 101 pqtqqpqqpf pqskqpqqpf pqpqqpqqsf pqqqpsliqq slqqqlnpck 151 nfllqqckpv slvsslwsii lppsdcqvmr qqccqqlaqi pqqlqcaaih 201 svvhsiimqq eqqeqlqgvq ilvplsqqqq vgqgilvqgq giiqpqqpaq 251 levirslvlq tlptmcnvyv ppycstirap fasivasigg q

TABLE 6

Amino acid sequence of Gamma-gliadin (Gliadin B-III) from
Triticum aestivum (NCBI accession no. P04730, (SEQ ID NO: 170))

1 pqqpfplqpq qsflwqsqqp flqqpqqpsp qpqqvvqiis patpttipsa 51 gkptsapfpq qqqhqqlaq qqipvvqpsi lqqlnpckvf lqqqcspvam 101 pqrlarsqml qqsschvmqq qccqqlpqip qqsryqaira iiysiilqeq 151 qqvqgsiqsq qqqpqqlgqc vsqpqqqsqq qlgqqpqqqq laqgtflqph 201 qiaqlevmts ialrilptmc svnvplyrtt tsvpfgvgtg vgay

TABLE 7

Amino acid sequence of Gamma-gliadin precursor from
Triticum aestivum (NCBI accession no. P08453, (SEQ ID NO: 171))

1 mktlliltil amaitigtan iqvdpsgqvq wlqqqlvpql qqpisqqpqq 51 tfpqpqqtfp hqpqqqvpqp qqpqqpflqp qqpfpqqpqq pfpqtqqpqq 101 pfpqqpqqpf pqtqqpqqpf pqqpqqpfpq tqqpqqpfpq lqqpqqpfpq 151 pqqqlpqpqq pqqsfpqqqr pfiqpslqqq lnpckniilq qskpaslvss 201 lwsiiwpqsd cqvmrqqccq qlaqipqqlq caaihsvvhs iimqqqqqqq 251 qqqgidiflp lsqheqvgqg slvqgqgiiq pqqpaqleai rslvlqtlps 301 mcnvyvppec simrapfasi vagiggq

TABLE 8

Amino acid sequence of Gamma-gliadin B-I precursor from
Triticum aestivum (NCBI accession no. P04729, (SEQ ID NO: 172))

```
  1 mktflvfali avvatsaiaq metscisgle rpwqqqplpp qqsfsqqppf
 51 sqqqqplpq qpsfsqqqpp fsqqqpilsq qppfsqqqqp vlpqqspfsq
101 qqqlvlppqq qqqqlvqqqi pivqpsvlqq lnpckvflqq qcspvampqr
151 larsqmwqqs schvmqqqcc qqlqqipeqs ryeairaiiy siilqeqqqg
201 fvqpqqqqpq qsgqgvsqsq qqsqqqlgqc sfqqpqqqlg qqpqqqqqqq
251 vlqgtflqph qiahleavts ialrtlptmc svnvplysat tsvpfgvgtg
301 vgay
```

TABLE 9

Amino acid sequence of Gamma-gliadin precursor from
Triticum aestivum (NCBI accession no. P08079, (SEQ ID NO: 173))

```
  1 mktlliltil amaitigtan mqvdpssqvq wpqqqpvpqp hqpfsqqpqq
 51 tfpqpqqtfp hqpqqqfpqp qqpqqqflqp qqpfpqqpqq pypqqpqqpf
101 pqtqqpqqlf pqsqqpqqqf sqpqqqfpqp qqpqqsfpqq qppfiqpslq
151 qqvnpcknfl lqqckpvslv sslwsmiwpq sdcqvmrqqc cqqlaqipqq
201 lqcaaihtii hsiimqqeqq eqqqgmhill plyqqqvgq gtlvqgqgii
251 q
```

TABLE 10

Amino acid sequence of Alpha/beta-gliadin MM1 precursor (Prolamin)
from Triticum aestivum (NCBI accession no. P18573, (SEQ ID NO: 174))

```
  1 mktflilall aivattaria vrvpvpqlqp qnpsqqqpqe qvplvqqqqf
 51 pgqqqpfppq qpypqpqpfp sqqpylqlqp fpqpqlpypq pqlpypqpql
101 pypqpqpfrp qqpypqsqpq ysqpqqpisq qqqqqqqqq qkqqqqqqqq
151 ilqqilqqql ipcrdvvlqq hsiaygssqv lqqstyqlvq qlccqqlwqi
201 peqsrcqaih nvvhaiilhq qqqqqqqqq gplsqvsfqq pqqqypsgqg
251 sfqpsqqnpq aqgsvqpqql pqfeeirnla letlpamcnv yippyctiap
301 vgifgtn
```

TABLE 11

Amino acid sequence of Alpha/beta-gliadin clone PTO-A10 (Prolamin)
from Triticum aestivum (NCBI accession no. P04728, (SEQ ID NO: 175))

```
  1 pqpqpqysqp qqpisqqqqq qqqqqqqqq eqqilqqilq qqlipcmdvv
 51 lqqhniahgr sqvlqqstyq llqelccqhl wqipeqsqcq aihnvvhaii
101 lhqqqkqqq qpssqfsfqq plqqyplgqq sfrpsqqnpq aqgsvqpqql
151 pqfeirnlal qtlpamcnvy ippyctiapf gifgtn
```

TABLE 12

Amino acid sequence of Alpha/beta-gliadin clone PW8142 precursor (Prolamin) from *Triticum aestivum* (NCBI accession no. P04727, (SEQ ID NO: 176))

```
  1 mktflilalv attattavrv pvpqlqpknp sqqqpqeqvp lvqqqqfpgq
 51 qqqfppqqpy pqpqpfpsqq pylqlqpfpq pqpflpqlpy pqpqsfppqq
101 pypqqrpkyl qpqqpisqqq aqqqqqqqqq qqqqqqqqil qqilqqqlip
151 crdvvlqqhn iahassqvlq qstyqllqql ccqqllqipe qsrcqaihnv
201 vhaiimhqqe qqqlqqqqq qqlqqqqqqq qqqqpssqv sfqqpqqqyp
251 ssqgsfqpsq qnpqaqgsvq pqqlpqfaei rnlalqtlpa mcnvyipphc
301 sttiapfgif gtn
```

TABLE 13

Amino acid sequence of Alpha/beta-gliadin clone PW1215 precursor (Prolamin) from *Triticum aestivum* (NCBI accession no. P04726, (SEQ ID NO: 177))

```
  1 mktflilall aivattatta vrvpvpqpqp qnpsqpqpqg qvplvqqqqf
 51 pgqqqfppq qpypqpqpfp sqqpylqlqp fpqpqpfppq lpypqpppfs
101 pqqpypqpqp qypqpqqpis qqqaqqqqqq qqqqqqqqq qqilqqilqq
151 qlipcrdvvl qqhniahars qvlqqstyqp lqqlccqqlw qipeqsrcqa
201 ihnvvhaiil hqqqrqqqps sqvslqqpqq qypsgqgffq psqqnpqaqg
251 svqpqqlpqf eeirnlalqt lprmcnvyip pycsttiapf gifgtn
```

TABLE 14

Amino acid sequence of Alpha/beta-gliadin A-IV precursor (Prolamin) from *Triticum aestivum* (NCBI accession no. P04724, (SEQ ID NO: 178))

```
  1 mktflilalr aivattatia vrvpvpqlqp qnpsqqqpqk qvplvqqqqf
 51 pgqqqpfppq qpypqqqpfp sqqpymqlqp fpqpqlpypq pqlpypqpqp
101 frpqqsypqp qpqysqpqqp isqqqqqqqq qqqqqqqilq qilqqqlipc
151 rdvvlqqhsi ahgssqvlqq styqlvqqfc cqqlwqipeq srcqaihnvv
201 haiilhqqqq qqqqqqqqq qplsqvcfqq sqqqypsgqg sfqpsqqnpq
251 aqgsvqpqql pqfeeirnla letlpamcnv yippyctiap vgifgtn
```

TABLE 15

Amino acid sequence of Alpha/beta-gliadin A-III precursor (Prolamin) from *Triticum aestivum* (NCBI accession no. P04723, (SEQ ID NO: 179))

```
  1 mktflilall aivattatsa vrvpvpqlqp qnpsqqqpqe qvplmqqqqq
 51 fpgqqeqfpp qqpyphqqpf psqqpypqpq pfppqlpypq tqpfppqqpy
101 pqpqpqypqp qqpisqqqaq qqqqqqtlq qilqqqlipc rdvvlqqhni
```

TABLE 15 -continued

Amino acid sequence of Alpha/beta-gliadin A-III
precursor (Prolamin) from *Triticum aestivum*
(NCBI accession no. P04723, (SEQ ID NO: 179))

```
151 ahassqvlqq ssyqqlqqlc cqqlfqipeq srcqaihnvv haiilhhhqq 201 qqqqpssqvs yqqpqeqyps gqvsfqssqq npqaqgsvqp qqlpqfqeir 251 nlalqtlpam cnvyippycs ttiapfgifg tn
```

TABLE 16

Amino acid sequence of Alpha/beta-gliadin A-II
precursor (Prolamin) from *Triticum aestivum*
(NCBI accession no. P04722, (SEQ ID NO: 180))

```
  1 mktfpilall aivattatta vrvpvpqlql qnpsqqqpqe qvplvqeqqf 51 qgqqqpfppq qpypqpqpfp sqqpylqlqp fpqpqlpypq pqpfrpqqpy 101 pqpqpqysqp qqpisqqqqq qqqqqqqqqq ilqqilqqql iperdvvlqq 151 hniahgssqv lqestyqlvq qlccqqlwqi peqsrcqaih nvvhaiilhq 201 qhhhqqqqq qqqqqplsqv sfqqpqqqyp sgqgffqpsq qnpqaqgsfq 251 pqqlpqfeei rnlalqtlpa mcnvyippyc tiapfgifgt n
```

TABLE 17

Amino acid sequence of Alpha/beta-gliadin A-I
precursor (Prolamin) from *Triticum aestivum*
(NCBI accession no. P04721, (SEQ ID NO: 181))

```
  1 mktflilall aivattatta vrvpvpqlqp qnpsqqqpqe qvplvqqqqf 51 lgqqqpfppq qpypqpqpfp sqqpylqlqp flqpqlpysq pqpfrpqqpy 101 pqpqpqysqp qqpisqqqqq qqqqqqqqqq qqqqiiqqil qqqlipcmdv 151 vlqqhnivhg ksqvlqqsty qllgelccqh lwqipeqsqc qaihnvvhai 201 ilhqqkqqq qpssqvsfqq plqqyplqqg sfrpsqqnpq aggsvqpqql 251 pqfeeirnla rk
```

TABLE 18

Amino acid sequence of gamma gliadin from *Triticum
aestivum* (NCBI accession no. AAQ63860, (SEQ ID NO: 182))

```
  1 mniqvdpssq vpwpqqqpfp qphqpfsqqp qqtfpqpqqt fphqpqqqfs 51 qpqqpqqqfi qpqqpfpqqp qqtypqrpqq pfpqtqqpqq pfpqsqqpqq 101 pfpqpqqqfp qpqqpqqsfp qqqpsliqqs lqqqlnpckn fllqqckpvs 151 lvsslwsmil prsdcqvmrq qccqqlaqip qqlqcaaihs ivhsiimqqe 201 qqeqrqgvqi lvplsqqqqv gqgtlvqgqg iiqpqqpaql evirslvlqt 251 latmcnvyvp pycstirapf asivagigqq yr
```

TABLE 19

Amino acid sequence of Omega-gliadin from *Triticum monococcum* (NCBI accession no. P02865, (SEQ ID NO: 183))

1 arqlnpsedqe lqspqqlypq qpypqqpy

Inhibitors of gliadin-derived peptide translocation across biological barriers are useful for treating diseases characterized by inflammation, including autoimmune diseases and particularly including celiac disease. Inhibitors of PTG-induced factors that increase biological barrier permeability are useful for treating diseases characterized by inflammation, including autoimmune diseases and particularly including celiac disease.

Activity of inhibitors of gliadin-derived peptide translocation and/or inhibitors of PTG-induced permeability can be measured by any means known in the art. Signaling events which can be determined include decrease in TEER, increase in LY permeability, increase in cytokine release, microglial recruitment, tyrosine kinase phosphorylation and chemotaxis, and increase in MMP-2 and MMP-9 gelatinolytic activity in cell-conditioned media.

The invention provides methods of identifying agents, compounds or lead compounds for agents active in inhibiting PTG-induced alterations in biological barrier permeability and/or peptide translocation. Generally, screening methods of the invention involve assaying for compounds which modulate the interaction of one or more gliadin fragments with one or more cells (e.g., epithelial cells, immune cells). A wide variety of assays for binding agents is provided including labeled in vitro protein-ligand binding assays, cell based assays, immunoassays, etc. A wide variety of formats may be used, including co-immunoprecipitation, 2-hybrid transactivation, fluorescent polarization, NMR, fluorescent resonance energy transfer (FRET), transcriptional activation, etc. For example, a wide variety of NMR-based methods are available to rapidly screen libraries of small compounds for binding to protein targets (Hajduk, P. J., et al. Quarterly Reviews of Biophysics, 1999. 32 (3): 211-40). In some embodiments, methods of the invention may be automated (e.g., high throughput screening) and may be used to screen chemical libraries for lead compounds. Identified compounds may be used to treat diseases involving increased biological barrier permeability including, for example, celiac disease, inflammatory bowel diseases and autoimmune diseases. Compounds identified by the methods of the invention may be further optimized to modulate biological barrier modulation, for example, may be derivatized. Multiple iterations of screening and derivatization may be employed to optimize the modulation of biological barrier permeability.

In vitro ligand binding assays employ a mixture of components including one or more gliadin-derived peptides or fragments and one or more gliadin binding components. Gliadin-derived peptides or fragments may be provided as fusion proteins (e.g., with purification tags such as 6-His). Assay mixtures typically further comprise a compound to be tested for inhibitory activity. Compounds to be tested may be of any kind known to those skilled in the art, for example, may be organic compounds, peptides, proteins, nucleic acids, lipids, carbohydrates and mixtures thereof. A variety of other reagents may also be included in the mixture including, but not limited to, salts, buffers, neutral proteins, e.g. albumin, detergents, protease inhibitors, nuclease inhibitors, antimicrobial agents, etc.

In general, assay mixtures may be incubated under conditions in which, but for the presence of the compound to be tested, gliadin-derived peptides or fragments specifically bind the gliadin binding components with a reference binding affinity. The mixture components can be added in any order that provides for the requisite bindings and incubations may be performed at any temperature which facilitates optimal binding. Incubation periods are likewise selected for optimal binding. In some embodiments, incubation periods may be minimized to facilitate rapid, high-throughput screening.

After incubation, the effect of the compound to be tested on the gliadin binding may be detected by any convenient way. For example, the gliadin-derived peptide or fragment or the gliadin binding component may be immobilized, and the other labeled; then in a solid-phase format, any of a variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the gliadin-derived peptide or fragment and the gliadin binding component in the absence of the compound to be tested as compared with the binding affinity in the presence of the compound to be tested indicates that the compound modulates the binding of the gliadin-derived peptide or fragment and the gliadin binding component. A difference, as used herein, is statistically significant and preferably represents at least a 50%, 60%, 70%, 80%, or 90% difference.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Measurement of Trans Epithelial Electric Resistance (TEER) and Epithelial Flux of a Fluorescent Marker Lucifer Yellow CaCo2 cells form monolayers that exhibit tight junctions between adjacent cells. Agonists of tight junctions can be identified by their ability to enhance the flux of compounds (e.g. ions, Lucifer Yellow) through a cell monolayer that comprises tight junctions; or by their ability to reduce TEER across a cell monolayer that comprises tight junctions. Treatment of CaCo2 monolayers with peptide tight junction agonist compounds leads to enhancement of Lucifer Yellow permeability through CaCo2 monolayers compared to vehicle alone. Treatment of CaCo2 monolayers with peptide tight junction agonist compounds leads to a decrease in TEER across CaCo2 monolayers compared to vehicle alone.

Tight junction agonists and agonists of the C1orf43 and CCDC78 proteins can be identified using the following method, and this method may be easily modified to identify antagonists and inhibitors of the C1orf43 and CCDC78 proteins:

Determination of TEER and Lucifer Yellow Flux

Prepare Modified Hank's Balanced Salt Solution (MHBSS) by obtaining 1 L bottle of HBSS removing 10 ml of HBSS and replacing it with 10 ml HEPES buffer pH 7.0. Adjust pH to 7.4±0.1 using concentrated NaOH (10 N).

Remove CaCo-2 cells from incubator, grown on 12-well, 3.0 μM, polycarbonate Transwell® filters (Corning) and record passage #, date cells seeded and age in days.

Aspirate cell culture medium from both the apical (AP) and basolateral (BL) compartments, replacing with 0.5 ml and 1.5 ml of MHBSS, respectively. Incubate cells at 37° C. for 30 minutes.

Using the MilliCell®-ERS instrument (Millipore), measure and record the transepithelial electrical resistance (TEER) across each filter and record.

Aspirate solution from the apical compartment of each filter (n=3 per condition) and replace with 0.5 ml of control and test solutions containing Lucifer Yellow and test compound if appropriate.

Place all plates into incubator set at 37° C. (±0.2), 50 RPM (±5) for a total of 180 minutes.

At t=30, 60, 120 and 180 minutes, measure and record the transepithelial electrical resistance (TEER) across each filter using the MilliCell-ERS instrument.

At t=60, 120 and 180 minutes remove 100 μl from each basolateral compartment and place it in a 96-well plate for Lucifer Yellow analysis, replace with 100 μl of MHBSS.

Make a Lucifer Yellow standard curve with the following dilutions (7500 μM, 3750 μM, 750 μM, 375 μM, 75 μM, 37.5 μM, 7.5 μM, 3.75 μM, 0.75 μM) and pipette 100 μL of each into a 96-well plate except for the first three standards mentioned above which require a 1:10 dilutions prior to transferring to the 96-well plate.

Harvest the remaining start solutions and what is left in each apical compartment into 1.5 ml vials. Freeze at −20° C. for future analysis.

Analyze each 96-well plate in a Tecan Spectra Fluor Plus using Magellan at 485 and 535 nm.

Materials:
Cells: CaCo-2 cells passage 40-60 grown on Transwell® plates for 21-28 days
Culture Medium: DMEM supplemented with 10% fetal bovine serum, 1% NEAA, 1% Penn/Strep
Buffers: Hank's Balanced Salt Solution (HBSS) without calcium and magnesium
Flasks: 100×20 mm Tissue culture dish Falcon.
Plates: 12 well polycarbonate Transwell® filters; 0.3 uM pore size

EXAMPLE 2

Identification of Cytokines Upregulated on Treatment of THP-1 cells by PT-Gliadin (PTG)

The monocytic cell line THP-1 was used to characterize the profile of cytokines whose expression was upregulated on exposure to protease treated gliadin (PTG). THP-1 cells were diluted to $5 \times 10^5$ cells/ml in RPMI medium supplemented with 10% heat inactivated fetal bovine serum.

$5 \times 10^5$ (1 ml) cells were plated in each well of a 12 well plate, and cells were incubated at 37° C. overnight. Test compounds (PTG 1 mg/ml; LPS 1 μg/ml) were added to the cultures, and incubation was continued a further 18 hours at 37° C.

Culture supernatants were harvested, and cytokines/chemokines were measured in each sample using a nitrocellulose membrane based proteomic profiler assay (R&D Systems). Assays were performed in triplicate. The cytokines screened in this assay included C5a, CD40 ligand, G-CSF, GM-CSF, GRO-α/CXCL1, I-309/CCL1, ICAM-1, IFNγ, IL-1α, IL-1β, IL-1ra, IL-2, IL-4, IL-5, IL-6, IL-8, IL-10, IL-12p70, IL-13, IL-16, IL-17, IL-17E, IL-23, IL-27, IL-32α, IP-10/CXCL10, I-TAC/CXCL11, MCP-1/CCL2, MIF, MIP-1α/CCL3, MIP-1β/CCCL3, RANTES/CCL5, SDF-1/CXCL12, Serpin-E1/PAI-1, TNFα, and TREM-1.

After 6 hours of PTG exposure THP-1 cells demonstrated increased expression of the cytokines IL-8, MIP-1α, MIP-1β, TNF-α and Gro-α. After 24 hours of exposure to PTG increased expression of RANTES and MIF were also observed.

EXAMPLE 3

Identification of Cytokines Upregulated on Treatment of PBMCs by PT-Gliadin (PTG)

Peripheral blood mononuclear cells were isolated from donated human blood samples using methods known in the art, and these PBMCs were used to characterize the profile of cytokines whose expression was upregulated on exposure to protease treated gliadin (PTG). PBMCs were suspended in RPMI medium supplemented with 5% heat inactivated human AB serum, and $2 \times 10^5$ cells were plated in each well of a 96 well plate. Cells were incubated at 37° C. with PTG (1 mg/ml) or LPS (1 μg/ml) in the presence or absence of test compounds being examined for the ability to suppress cytokine production. Supernatant samples were harvested following treatment, and cytokines were assayed by ELISA (R&D Systems).

Expression of IL-6, IL-8, MIP-1α, and Gro-α were induced by treatment with LPS and PTG. Expression of these cytokines was not reduced by treatment with peptide GGVLVQPG (SEQ ID NO:1).

Increased expression of GM-CSF and IL-16 was induced by exposure to LPS and PTG. This increased expression of these cytokines was inhibited by treatment with peptide GGVLVQPG (SEQ ID NO:1).

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

TABLE 20

Peptide permeability inhibitors

| SEQ ID NO: | Sequence | Prevented TEER Reduction | Reduced LY Permeability |
|---|---|---|---|
| 1 | Gly-Gly-Val-Leu-Val-Gln-Pro-Gly | − | + |
| 2 | Ala-Gly-Val-Leu-Val-Gln-Pro-Gly | − | + |
| 3 | Gly-Ala-Val-Leu-Val-Gln-Pro-Gly | − | + |
| 4 | Gly-Gly-Ala-Leu-Val-Gln-Pro-Gly | − | + |
| 5 | Gly-Gly-Val-Ala-Val-Gln-Pro-Gly | − | + |
| 6 | Gly-Gly-Val-Leu-Ala-Gln-Pro-Gly | − | − |
| 7 | Gly-Gly-Val-Leu-Val-Ala-Pro-Gly | − | − |
| 8 | Gly-Gly-Val-Leu-Val-Gln-Ala-Gly | − | − |
| 9 | Gly-Gly-Val-Leu-Val-Gln-Pro-Ala | − | − |
| 10 | Gly-Asp-Val-Leu-Val-Gln-Pro-Gly | + | + |
| 11 | Gly-Glu-Val-Leu-Val-Gln-Pro-Gly | + | + |
| 12 | Gly-Gln-Val-Leu-Val-Gln-Pro-Gly | + | + |
| 13 | Gly-Phe-Val-Leu-Val-Gln-Pro-Gly | + | + |
| 14 | Gly-His-Val-Leu-Val-Gln-Pro-Gly | + | + |
| 15 | Gly-Arg-Val-Leu-Val-Gln-Pro-Gly | + | + |
| 16 | Gly-Lys-Val-Leu-Val-Gln-Pro-Gly | + | + |
| 17 | Gly-Ile-Val-Leu-Val-Gln-Pro-Gly | + | + |
| 18 | Gly-Trp-Val-Leu-Val-Gln-Pro-Gly | − | − |
| 19 | Gly-Pro-Val-Leu-Val-Gln-Pro-Gly | + | + |
| 20 | Gly-Val-Val-Leu-Val-Gln-Pro-Gly | + | + |
| 21 | Gly-Leu-Val-Leu-Val-Gln-Pro-Gly | + | + |
| 22 | Gly-Asn-Val-Leu-Val-Gln-Pro-Gly | + | + |
| 23 | Gly-Thr-Val-Leu-Val-Gln-Pro-Gly | + | + |
| 24 | Gly-Gly-Gly-Leu-Val-Gln-Pro-Gly | − | − |
| 25 | Gly-Gly-Leu-Leu-Val-Gln-Pro-Gly | − | − |
| 26 | Gly-Gly-Ile-Leu-Val-Gln-Pro-Gly | − | − |
| 27 | Gly-Gly-Phe-Leu-Val-Gln-Pro-Gly | + | + |
| 28 | Gly-Gly-Arg-Leu-Val-Gln-Pro-Gly | − | − |
| 29 | Gly-Gly-Asp-Leu-Val-Gln-Pro-Gly | − | − |
| 30 | Gly-Gly-Gln-Leu-Val-Gln-Pro-Gly | − | − |
| 31 | Gly-Gly-His-Leu-Val-Gln-Pro-Gly | − | − |
| 32 | Gly-Gly-Met-Leu-Val-Gln-Pro-Gly | + | + |
| 33 | Gly-Gly-Ser-Leu-Val-Gln-Pro-Gly | − | − |
| 34 | Gly-Gly-Thr-Leu-Val-Gln-Pro-Gly | + | + |
| 35 | Gly-Gly-Pro-Leu-Val-Gln- | − | − |
| 36 | Gly-Gly-Val-Gly-Val-Gln-Pro-Gly | + | + |
| 37 | Gly-Gly-Val-Val-Val-Gln-Pro-Gly | − | − |

TABLE 20 -continued

Peptide permeability inhibitors

| SEQ ID NO: | Sequence | Prevented TEER Reduction | Reduced LY Permeability |
|---|---|---|---|
| 38 | Gly-Gly-Val-Ile-Val-Gln-Pro-Gly | - | - |
| 39 | Gly-Gly-Val-Phe-Val-Gln-Pro-Gly | - | - |
| 40 | Gly-Gly-Val-Arg-Val-Gln-Pro-Gly | - | - |
| 41 | Gly-Gly-Val-Asp-Val-Gln-Pro-Gly | - | - |
| 42 | Gly-Gly-Val-Gln-Val-Gln-Pro-Gly | - | - |
| 43 | Gly-Gly-Val-His-Val-Gln-Pro-Gly | - | - |
| 44 | Gly-Gly-Val-Met-Val-Gln-Pro-Gly | - | - |
| 45 | Gly-Gly-Val-Ser-Val-Gln-Pro-Gly | - | - |
| 46 | Gly-Gly-Val-Thr-Val-Gln-Pro-Gly | - | - |
| 47 | Gly-Gly-Val-Pro-Val-Gln-Pro-Gly | - | - |
| 48 | D-Ala-Gly-Val-Leu-Val-Gln-Pro-Gly | + | + |
| 49 | Asp-Gly-Val-Leu-Val-Gln-Pro-Gly | + | + |
| 50 | Glu-Gly-Val-Leu-Val-Gln-Pro-Gly | - | - |
| 51 | Gln-Gly-Val-Leu-Val-Gln-Pro-Gly | NT | NT |
| 52 | Phe-Gly-Val-Leu-Val-Gln-Pro-Gly | NT | NT |
| 53 | His-Gly-Val-Leu-Val-Gln-Pro-Gly | NT | NT |
| 54 | Arg-Gly-Val-Leu-Val-Gln-Pro-Gly | - | - |
| 55 | Lys-Gly-Val-Leu-Val-Gln-Pro-Gly | + | + |
| 56 | Ile-Gly-Val-Leu-Val-Gln-Pro-Gly | - | - |
| 57 | Trp-Gly-Val-Leu-Val-Gln-Pro-Gly | - | - |
| 58 | Pro-Gly-Val-Leu-Val-Gln-Pro-Gly | + | + |
| 59 | Val-Gly-Val-Leu-Val-Gln-Pro-Gly | - | - |
| 60 | Leu-Gly-Val-Leu-Val-Gln-Pro-Gly | - | - |
| 61 | Thr-Gly-Val-Leu-Val-Gln-Pro-Gly | NT | NT |
| 62 | Asn-Gly-Val-Leu-Val-Gln-Pro-Gly | NT | NT |
| 63 | D-Phe-Gly-Val-Leu-Val-Gln-Pro-Gly | - | - |
| 64 | Cha-Gly-Val-Leu-Lav-Gln-Pro-Gly | NT | NT |
| 65 | Met(O)2-Gly-Val-Leu-Val-Gln-Pro-Gly | NT | NT |
| 66 | Gly-Val-Leu-Val-Gln-Pro-Gly | - | - |
| 67 | Val-Leu-Val-Gln-Pro-Gly | + | + |
| 68 | Leu-Val-Gln-Pro-Gly | + | + |
| 69 | Val-Gln-Pro-Gly | + | + |
| 70 | Gln-Pro-Gly | + | + |
| 71 | Gly-Gly-Val-Leu-Val-Gln-Pro | - | + |
| 72 | Gly-Gly-Val-Leu-Val-Gln | + | + |
| 73 | Gly-Gly-Val-Leu-Val | + | + |
| 74 | Gly-Gly-Val-Leu | + | + |

TABLE 20 -continued

Peptide permeability inhibitors

| SEQ ID NO: | Sequence | Prevented TEER Reduction | Reduced LY Permeability |
|---|---|---|---|
| 75 | Gly-Gly-Val | + | + |
| 76 | Gly-Gly-D-Val-Leu-Val-Gln-Pro-Gly | + | + |
| 77 | Gly-Gly-Val-D-Leu-Val-Gln-Pro-Gly | + | + |
| 78 | Gly-Gly-Val-Leu-D-Val-Gln-Pro-Gly | - | - |
| 79 | Gly-Gly-Val-Leu-Val-D-Gln-Pro-Gly | + | + |
| 80 | Gly-Gly-Val-Leu-Val-Gln-D-Pro-Gly | + | + |
| 81 | Gly-D-Pro-D-Gln-D-Val-D-Leu-D-Val-Gly-Gly | + | + |
| 82 | Gly-D-Pro-D-Gln-D-Val-D-Leu-Val-Gly-Gly | + | + |
| 83 | Gly-D-Pro-D-Gln-D-Val-Leu-D-Val-Gly-Gly | + | + |
| 84 | Gly-D-Pro-D-Gln-Val-D-Leu-D-Val-Gly-Gly | + | + |
| 85 | Gly-D-Pro-Gln-D-Val-D-Leu-D-Val-Gly-Gly | + | + |
| 86 | Gly-Pro-D-Gln-D-Val-D-Leu-D-Val-Gly-Gly | - | - |
| 87 | Gly-Pro-Gln-Val-Leu-Val-Gly-Gly | + | + |
| 88 | Gly-D-Pro-Gln-Val-Leu-Val-Gly-Gly | + | + |
| 89 | Gly-Pro-D-Gln-Val-Leu-Val-Gly-Gly | - | - |
| 90 | Gly-Pro-Gln-D-Val-Leu-Val-Gly-Gly | - | - |
| 91 | Gly-Pro-Gln-Val-D-Leu-Val-Gly-Gly | + | + |
| 92 | Gly-Pro-Gln-Val-Leu-D-Val-Gly-Gly | + | + |
| 93 | Gly-Gly-D-Val-D-Leu-D-Val-D-Gln-D-Pro-Gly | | |
| 94 | Gly-Gly-D-Val-D-Leu-D-Val-D-Gln-Pro-Gly | + | - |
| 95 | Gly-Gly-D-Val-D-Leu-D-Val-Gln-D-Pro-Gly | - | - |
| 96 | Gly-Gly-D-Val-D-Leu-Val-D-Gln-D-Pro-Gly | - | - |
| 97 | Gly-Gly-D-Val-Leu-D-Val-D-Gln-D-Pro-Gly | - | - |
| 98 | Gly-Gly-Val-D-Leu-D-Val-D-Gln-D-Pro-Gly | + | + |
| 99 | Gly-D-Phe-Val-Leu-Val-Gln-Pro-Gly | + | + |
| 100 | Ala-Pro-Gly | + | + |
| 101 | Gln-Ala-Gly | + | + |
| 102 | Gln-Pro-Ala | + | + |
| 103 | (d)Gln-Pro-Gly | + | + |
| 104 | Gln-(d)Pro-Gly | + | + |
| 105 | (d)Gln-(d)Pro-Gly | - | - |

TABLE 20 -continued

Peptide permeability inhibitors

| SEQ ID NO: | Sequence | Prevented TEER Reduction | Reduced LY Permeability |
|---|---|---|---|
| 106 | Gly-Pro-Gln | + | + |
| 107 | Gly-(d)Pro-Gln | - | - |
| 108 | Gly-Pro-(d)Gln | - | - |
| 109 | Gly-(d)Pro-(d)Gln | - | - |
| 110 | Ala-Pro-Gly | + | + |
| 111 | His-Pro-Gly | + | + |
| 112 | Asp-Pro-Gly | - | - |
| 113 | Arg-Pro-Gly | + | + |
| 114 | Phe-Pro-Gly | + | + |
| 115 | Gly-Pro-Gly | + | + |
| 116 | Glu-Pro-Gly | + | + |
| 117 | Lys-Pro-Gly | + | + |
| 118 | Leu-Pro-Gly | + | + |
| 119 | Met-Pro-Gly | + | + |
| 120 | Asn-Pro-Gly | + | + |
| 121 | Ser-Pro-Gly | + | + |
| 122 | Tyr-Pro-Gly | + | + |
| 123 | Thr-Pro-Gly | - | + |
| 124 | Ile-Pro-Gly | + | + |
| 125 | Trp-Pro-Gly | + | + |
| 126 | Pro-Pro-Gly | - | - |
| 127 | Val-Pro-Gly | - | + |
| 128 | Glp-Pro-Gly | + | + |
| 129 | Glp-Val-Gly | - | - |
| 130 | Glp-Gln-Gly | - | - |
| 131 | Glp-Ser-Gly | - | - |
| 132 | Glp-Lys-Gly | - | - |
| 133 | Glp-Phe-Gly | - | - |
| 134 | Glp-Glu-Gly | - | - |
| 135 | Glp-Thr-Gly | - | - |
| 136 | Glp-Ile-Gly | - | - |
| 137 | Glp-Tyr-Gly | - | - |
| 138 | Glp-His-Gly | - | - |
| 139 | Glp-Asn-Gly | - | - |
| 140 | Glp-Arg-Gly | - | - |
| 141 | Glp-Gly-Gly | - | - |
| 142 | Glp-Trp-Gly | - | - |

TABLE 20 -continued

Peptide permeability inhibitors

| SEQ ID NO: | Sequence | Prevented TEER Reduction | Reduced LY Permeability |
|---|---|---|---|
| 143 | Glp-Asp-Gly | - | - |
| 144 | Glp-Met-Gly | - | - |
| 145 | Glp-Leu-Gly | - | - |
| 146 | Glp-Pro-Gln | - | - |
| 147 | Glp-Pro-Asn | + | - |
| 148 | Glp-Pro-Gln | - | - |
| 149 | Glp-Pro-Ser | - | - |
| 150 | Glp-Pro-Pro | + | - |
| 151 | Glp-Pro-Trp | - | - |
| 152 | Glp-Pro-Asp | - | - |
| 153 | Glp-Pro-His | - | - |
| 154 | Glp-Pro-Leu | - | - |
| 155 | Glp-Pro-Arg | - | - |
| 156 | Glp-Pro-Val | - | - |
| 157 | Glp-Pro-Lys | - | - |
| 158 | Glp-Pro-Glu | - | - |
| 159 | Glp-Pro-Phe | - | - |
| 160 | Glp-Pro-Ile | + | - |
| 161 | Glp-Pro-Met | + | - |
| 162 | Glp-Pro-Tyr | + | - |

Met(O)2 = Methioninedioxide,
Cha = cyclohexyl-Ala

---

What is claimed is:

1. A pharmaceutical composition comprising an effective amount of a peptide inhibitor of tight junction permeability of the sequence Gly-Gly-(d)Val-(d)Leu-(d)Val-(d)Gln-(d)Pro-Gly (SEQ ID NO:93), and one or more enteric agents that are stable in gastric fluid but dissolve in intestinal fluid.

2. The composition of claim 1, wherein the composition substantially releases the peptide in the duodenum or the jejunum.

3. The composition of claim 2, wherein the composition releases 30% or less of peptide in gastric fluid with a pH of 5 or less in approximately sixty minutes.

4. The composition of claim 2, wherein the composition releases 70% or more of peptide in intestinal fluid with a pH of 5 or greater in approximately sixty minutes.

5. A method for inhibiting increased intestinal epithelial barrier permeability in a patient, comprising administering to said epithelial barrier in the patient the composition of claim 1.

6. The method of claim 5, wherein the patient has celiac disease.

7. The method of claim 5, wherein the patient has Crohn's disease or ulcerative colitis (UC).

8. The method of claim 5, wherein the subject has an autoimmune or inflammation-associated disease selected from the group consisting of diabetes, autoimmune hepatitis, multiple sclerosis, autism, dermatitis herpetiformis, IgA nephropathy, primary biliary cirrhosis, rheumatoid arthritis, systemic lupus erythematosus, Grave's disease, Hashimoto's disease, and depression.

9. The method of claim 5, wherein the patient has necrotizing enterocolitis.

* * * * *

SEQUENCE LISTING

<160> NUMBER OF SEQ ID NOS: 183

<210> SEQ ID NO 1
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 1

Gly Gly Val Leu Val Gln Pro Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 2

Ala Gly Val Leu Val Gln Pro Gly

```
1               5

<210> SEQ ID NO 3
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 3

Gly Ala Val Leu Val Gln Pro Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 4

Gly Gly Ala Leu Val Gln Pro Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 5

Gly Gly Val Ala Val Gln Pro Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 6

Gly Gly Val Leu Ala Gln Pro Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 7

Gly Gly Val Leu Val Ala Pro Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 8

Gly Gly Val Leu Val Gln Ala Gly
1               5
```

<210> SEQ ID NO 9
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 9

Gly Gly Val Leu Val Gln Pro Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 10

Gly Asp Val Leu Val Gln Pro Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 11

Gly Glu Val Leu Val Gln Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 12

Gly Gln Val Leu Val Gln Pro Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 13

Gly Phe Val Leu Val Gln Pro Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 14

Gly His Val Leu Val Gln Pro Gly
1               5

```
<210> SEQ ID NO 15
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 15

Gly Arg Val Leu Val Gln Pro Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 16

Gly Lys Val Leu Val Gln Pro Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 17

Gly Ile Val Leu Val Gln Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 18

Gly Trp Val Leu Val Gln Pro Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 19

Gly Pro Val Leu Val Gln Pro Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 20

Gly Val Val Leu Val Gln Pro Gly
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 21

Gly Leu Val Leu Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 22

Gly Asn Val Leu Val Gln Pro Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 23

Gly Thr Val Leu Val Gln Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 24

Gly Gly Gly Leu Val Gln Pro Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 25

Gly Gly Leu Leu Val Gln Pro Gly
1               5

<210> SEQ ID NO 26
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 26

Gly Gly Ile Leu Val Gln Pro Gly
1               5

<210> SEQ ID NO 27
```

```
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 27

Gly Gly Phe Leu Val Gln Pro Gly
1               5

<210> SEQ ID NO 28
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 28

Gly Gly Arg Leu Val Gln Pro Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 29

Gly Gly Asp Leu Val Gln Pro Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 30

Gly Gly Gln Leu Val Gln Pro Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 31

Gly Gly His Leu Val Gln Pro Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 32

Gly Gly Met Leu Val Gln Pro Gly
1               5

<210> SEQ ID NO 33
<211> LENGTH: 8
```

```
<212> TYPE: PRT
<213> ORGANISM: Artificial Sequence
<220> FEATURE:
<223> OTHER INFORMATION: Peptide permeability inhibitor

<400> SEQUENCE: 33

Gly Gly Ser Leu Val Gln Pro Gly
1               5

<210> SEQ ID NO 34
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 34

Gly Gly Thr Leu Val Gln Pro Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 35

Gly Gly Pro Leu Val Gln Pro Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 36

Gly Gly Val Gly Val Gln Pro Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 37

Gly Gly Val Val Val Gln Pro Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 38

Gly Gly Val Ile Val Gln Pro Gly
1               5

<210> SEQ ID NO 39
<211> LENGTH: 8
<212> TYPE: PRT
```

```
<213> ORGANISM: Artificial Sequence
<220> FEATURE:
<223> OTHER INFORMATION: Peptide permeability inhibitor

<400> SEQUENCE: 39

Gly Gly Val Phe Val Gln Pro Gly
1               5

<210> SEQ ID NO 40
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 40

Gly Gly Val Arg Val Gln Pro Gly
1               5

<210> SEQ ID NO 41
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 41

Gly Gly Val Asp Val Gln Pro Gly
1               5

<210> SEQ ID NO 42
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 42

Gly Gly Val Gln Val Gln Pro Gly
1               5

<210> SEQ ID NO 43
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 43

Gly Gly Val His Val Gln Pro Gly
1               5

<210> SEQ ID NO 44
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 44

Gly Gly Val Met Val Gln Pro Gly
1               5

<210> SEQ ID NO 45
<211> LENGTH: 8
<212> TYPE: PRT
<213> ORGANISM: Artificial Sequence
```

```
<220> FEATURE:
<223> OTHER INFORMATION: Peptide permeability inhibitor

<400> SEQUENCE: 45

Gly Gly Val Ser Val Gln Pro Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 46

Gly Gly Val Thr Val Gln Pro Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 47

Gly Gly Val Pro Val Gln Pro Gly
1               5

<210> SEQ ID NO 48
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Ala may be D-Ala

<400> SEQUENCE: 48

Ala Gly Val Leu Val Gln Pro Gly
1               5

<210> SEQ ID NO 49
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 49

Asp Gly Val Leu Val Gln Pro Gly
1               5

<210> SEQ ID NO 50
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 50

Glu Gly Val Leu Val Gln Pro Gly
1               5

<210> SEQ ID NO 51
```

```
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 51

Gln Gly Val Leu Val Gln Pro Gly
1               5

<210> SEQ ID NO 52
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 52

Phe Gly Val Leu Val Gln Pro Gly
1               5

<210> SEQ ID NO 53
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 53

His Gly Val Leu Val Gln Pro Gly
1               5

<210> SEQ ID NO 54
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 54

Arg Gly Val Leu Val Gln Pro Gly
1               5

<210> SEQ ID NO 55
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 55

Lys Gly Val Leu Val Gln Pro Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 56

Ile Gly Val Leu Val Gln Pro Gly
1               5

<210> SEQ ID NO 57
<211> LENGTH: 8
```

```
<212> TYPE: PRT
<213> ORGANISM: Artificial Sequence
<220> FEATURE:
<223> OTHER INFORMATION: Peptide permeability inhibitor

<400> SEQUENCE: 57

Trp Gly Val Leu Val Gln Pro Gly
1               5

<210> SEQ ID NO 58
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 58

Pro Gly Val Leu Val Gln Pro Gly
1               5

<210> SEQ ID NO 59
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 59

Val Gly Val Leu Val Gln Pro Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 60

Leu Gly Val Leu Val Gln Pro Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 61

Thr Gly Val Leu Val Gln Pro Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 62

Asn Gly Val Leu Val Gln Pro Gly
1               5

<210> SEQ ID NO 63
<211> LENGTH: 8
<212> TYPE: PRT
```

```
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Phe may be D-Phe

<400> SEQUENCE: 63

Phe Gly Val Leu Val Gln Pro Gly
 1               5

<210> SEQ ID NO 64
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be cyclohexyl-Ala
<220> FEATURE:
<221> NAME/KEY: misc_feature
<222> LOCATION: (5)..(5)
<223> OTHER INFORMATION: Xaa may be Val or any other natural or
      non-natural amino acid

<400> SEQUENCE: 64

Xaa Gly Val Leu Xaa Gln Pro Gly
 1               5

<210> SEQ ID NO 65
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be Methioninedioxide

<400> SEQUENCE: 65

Xaa Gly Val Leu Val Gln Pro Gly
 1               5

<210> SEQ ID NO 66
<211> LENGTH: 7
<212> TYPE: PRT
<213> ORGANISM: Artificial Sequence
<220> FEATURE:
<223> OTHER INFORMATION: Peptide permeability inhibitor

<400> SEQUENCE: 66

Gly Val Leu Val Gln Pro Gly
 1               5

<210> SEQ ID NO 67
<211> LENGTH: 6
<212> TYPE: PRT
<213> ORGANISM: Artificial Sequence
<220> FEATURE:
<223> OTHER INFORMATION: Peptide permeability inhibitor

<400> SEQUENCE: 67

Val Leu Val Gln Pro Gly
 1               5
```

```
<210> SEQ ID NO 68
<211> LENGTH: 5
<212> TYPE: PRT
<213> ORGANISM: Artificial Sequence
<220> FEATURE:
<223> OTHER INFORMATION: Peptide permeability inhibitor

<400> SEQUENCE: 68

Leu Val Gln Pro Gly
1               5

<210> SEQ ID NO 69
<211> LENGTH: 4
<212> TYPE: PRT
<213> ORGANISM: Artificial Sequence
<220> FEATURE:
<223> OTHER INFORMATION: Peptide permeability inhibitor

<400> SEQUENCE: 69

Val Gln Pro Gly
1

<210> SEQ ID NO 70
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 70

Gln Pro Gly
1

<210> SEQ ID NO 71
<211> LENGTH: 7
<212> TYPE: PRT
<213> ORGANISM: Artificial Sequence
<220> FEATURE:
<223> OTHER INFORMATION: Peptide permeability inhibitor

<400> SEQUENCE: 71

Gly Gly Val Leu Val Gln Pro
1               5

<210> SEQ ID NO 72
<211> LENGTH: 6
<212> TYPE: PRT
<213> ORGANISM: Artificial Sequence
<220> FEATURE:
<223> OTHER INFORMATION: Peptide permeability inhibitor

<400> SEQUENCE: 72

Gly Gly Val Leu Val Gln
1               5

<210> SEQ ID NO 73
<211> LENGTH: 5
<212> TYPE: PRT
<213> ORGANISM: Artificial Sequence
<220> FEATURE:
<223> OTHER INFORMATION: Peptide permeability inhibitor

<400> SEQUENCE: 73

Gly Gly Val Leu Val
1               5

<210> SEQ ID NO 74
```

```
<211> LENGTH: 4
<212> TYPE: PRT
<213> ORGANISM: Artificial Sequence
<220> FEATURE:
<223> OTHER INFORMATION: Peptide permeability inhibitor

<400> SEQUENCE: 74

Gly Gly Val Leu
1

<210> SEQ ID NO 75
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 75

Gly Gly Val
1

<210> SEQ ID NO 76
<211> LENGTH: 9
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (4)..(4)
<223> OTHER INFORMATION: Val may be D-Val

<400> SEQUENCE: 76

Gly Gly Asp Val Leu Val Gln Pro Gly
1               5

<210> SEQ ID NO 77
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (4)..(4)
<223> OTHER INFORMATION: Leu may be D-Leu

<400> SEQUENCE: 77

Gly Gly Val Leu Val Gln Pro Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (5)..(5)
<223> OTHER INFORMATION: Val may be D-Val

<400> SEQUENCE: 78

Gly Gly Val Leu Val Gln Pro Gly
1               5

<210> SEQ ID NO 79
<211> LENGTH: 8
<212> TYPE: PRT
```

```
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (6)..(6)
<223> OTHER INFORMATION: Gln may be D-Gln

<400> SEQUENCE: 79

Gly Gly Val Leu Val Gln Pro Gly
1               5

<210> SEQ ID NO 80
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (7)..(7)
<223> OTHER INFORMATION: Pro may be D-Pro

<400> SEQUENCE: 80

Gly Gly Val Leu Val Gln Pro Gly
1               5

<210> SEQ ID NO 81
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (3)..(3)
<223> OTHER INFORMATION: Gln may be D-Gln
<220> FEATURE:
<221> NAME/KEY: misc_feature
<222> LOCATION: (4)..(4)
<223> OTHER INFORMATION: Val may be D-Val
<220> FEATURE:
<221> NAME/KEY: misc_feature
<222> LOCATION: (5)..(5)
<223> OTHER INFORMATION: Leu may be D-Leu
<220> FEATURE:
<221> NAME/KEY: misc_feature
<222> LOCATION: (6)..(6)
<223> OTHER INFORMATION: Val may be D-Val

<400> SEQUENCE: 81

Gly Pro Gln Val Leu Val Gly Gly
1               5

<210> SEQ ID NO 82
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (3)..(3)
<223> OTHER INFORMATION: Gln may be D-Gln
<220> FEATURE:
```

```
<221> NAME/KEY: misc_feature
<222> LOCATION: (4)..(4)
<223> OTHER INFORMATION: Val may be D-Val
<220> FEATURE:
<221> NAME/KEY: misc_feature
<222> LOCATION: (5)..(5)
<223> OTHER INFORMATION: Leu may be D-Leu

<400> SEQUENCE: 82

Gly Pro Gln Val Leu Val Gly Gly
1               5

<210> SEQ ID NO 83
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (3)..(3)
<223> OTHER INFORMATION: Gln may be D-Gln
<220> FEATURE:
<221> NAME/KEY: misc_feature
<222> LOCATION: (4)..(4)
<223> OTHER INFORMATION: Val may be D-Val
<220> FEATURE:
<221> NAME/KEY: misc_feature
<222> LOCATION: (6)..(6)
<223> OTHER INFORMATION: Val may be D-Val

<400> SEQUENCE: 83

Gly Pro Gln Val Leu Val Gly Gly
1               5

<210> SEQ ID NO 84
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (3)..(3)
<223> OTHER INFORMATION: Gln may be D-Gln
<220> FEATURE:
<221> NAME/KEY: misc_feature
<222> LOCATION: (5)..(5)
<223> OTHER INFORMATION: Leu may be D-Leu
<220> FEATURE:
<221> NAME/KEY: misc_feature
<222> LOCATION: (6)..(6)
<223> OTHER INFORMATION: Val may be D-Val

<400> SEQUENCE: 84

Gly Pro Gln Val Leu Val Gly Gly
1               5

<210> SEQ ID NO 85
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
```

```
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (4)..(4)
<223> OTHER INFORMATION: Val may be D-Val
<220> FEATURE:
<221> NAME/KEY: misc_feature
<222> LOCATION: (5)..(5)
<223> OTHER INFORMATION: Leu may be D-Leu
<220> FEATURE:
<221> NAME/KEY: misc_feature
<222> LOCATION: (6)..(6)
<223> OTHER INFORMATION: Val may be D-Val

<400> SEQUENCE: 85

Gly Pro Gln Val Leu Val Gly Gly
1               5

<210> SEQ ID NO 86
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
<223> OTHER INFORMATION: Gln may be D-Gln
<220> FEATURE:
<221> NAME/KEY: misc_feature
<222> LOCATION: (4)..(4)
<223> OTHER INFORMATION: Val may be D-Val
<220> FEATURE:
<221> NAME/KEY: misc_feature
<222> LOCATION: (5)..(5)
<223> OTHER INFORMATION: Leu may be D-Leu
<220> FEATURE:
<221> NAME/KEY: misc_feature
<222> LOCATION: (6)..(6)
<223> OTHER INFORMATION: Val may be D-Val

<400> SEQUENCE: 86

Gly Pro Gln Val Leu Val Gly Gly
1               5

<210> SEQ ID NO 87
<211> LENGTH: 8
<212> TYPE: PRT
<213> ORGANISM: Artificial Sequence
<220> FEATURE:
<223> OTHER INFORMATION: Peptide permeability inhibitor

<400> SEQUENCE: 87

Gly Pro Gln Val Leu Val Gly Gly
1               5

<210> SEQ ID NO 88
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro

<400> SEQUENCE: 88

Gly Pro Gln Val Leu Val Gly Gly
1               5
```

```
<210> SEQ ID NO 89
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
<223> OTHER INFORMATION: Gln may be D-Gln

<400> SEQUENCE: 89

Gly Pro Gln Val Leu Val Gly Gly
1               5

<210> SEQ ID NO 90
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (4)..(4)
<223> OTHER INFORMATION: Val may be D-Val

<400> SEQUENCE: 90

Gly Pro Gln Val Leu Val Gly Gly
1               5

<210> SEQ ID NO 91
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (5)..(5)
<223> OTHER INFORMATION: Leu may be D-Leu

<400> SEQUENCE: 91

Gly Pro Gln Val Leu Val Gly Gly
1               5

<210> SEQ ID NO 92
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (6)..(6)
<223> OTHER INFORMATION: Val may be D-Val

<400> SEQUENCE: 92

Gly Pro Gln Val Leu Val Gly Gly
1               5

<210> SEQ ID NO 93
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
```

```
<223> OTHER INFORMATION: Val may be D-Val
<220> FEATURE:
<221> NAME/KEY: misc_feature
<222> LOCATION: (4)..(4)
<223> OTHER INFORMATION: Leu may be D-Leu
<220> FEATURE:
<221> NAME/KEY: misc_feature
<222> LOCATION: (5)..(5)
<223> OTHER INFORMATION: Val may be D-Val
<220> FEATURE:
<221> NAME/KEY: misc_feature
<222> LOCATION: (6)..(6)
<223> OTHER INFORMATION: Gln may be D-Gln
<220> FEATURE:
<221> NAME/KEY: misc_feature
<222> LOCATION: (7)..(7)
<223> OTHER INFORMATION: Pro may be D-Pro

<400> SEQUENCE: 93

Gly Gly Val Leu Val Gln Pro Gly
1               5

<210> SEQ ID NO 94
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
<223> OTHER INFORMATION: Val may be D-Val
<220> FEATURE:
<221> NAME/KEY: misc_feature
<222> LOCATION: (4)..(4)
<223> OTHER INFORMATION: Leu may be D-Leu
<220> FEATURE:
<221> NAME/KEY: misc_feature
<222> LOCATION: (5)..(5)
<223> OTHER INFORMATION: Val may be D-Val
<220> FEATURE:
<221> NAME/KEY: misc_feature
<222> LOCATION: (6)..(6)
<223> OTHER INFORMATION: Gln may be D-Gln

<400> SEQUENCE: 94

Gly Gly Val Leu Val Gln Pro Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
<223> OTHER INFORMATION: Val may be D-Val
<220> FEATURE:
<221> NAME/KEY: misc_feature
<222> LOCATION: (4)..(4)
<223> OTHER INFORMATION: Leu may be D-Leu
<220> FEATURE:
<221> NAME/KEY: misc_feature
<222> LOCATION: (5)..(5)
<223> OTHER INFORMATION: Val may be D-Val
<220> FEATURE:
<221> NAME/KEY: misc_feature
<222> LOCATION: (7)..(7)
<223> OTHER INFORMATION: Pro may be D-Pro

<400> SEQUENCE: 95

Gly Gly Val Leu Val Gln Pro Gly
```

<210> SEQ ID NO 96
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
<223> OTHER INFORMATION: Val may be D-Val
<220> FEATURE:
<221> NAME/KEY: misc_feature
<222> LOCATION: (4)..(4)
<223> OTHER INFORMATION: Leu may be D-Leu
<220> FEATURE:
<221> NAME/KEY: misc_feature
<222> LOCATION: (6)..(6)
<223> OTHER INFORMATION: Gln may be D-Gln
<220> FEATURE:
<221> NAME/KEY: misc_feature
<222> LOCATION: (7)..(7)
<223> OTHER INFORMATION: Pro may be D-Pro

<400> SEQUENCE: 96

Gly Gly Val Leu Val Gln Pro Gly
1               5

<210> SEQ ID NO 97
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (3)..(3)
<223> OTHER INFORMATION: Val may be D-Val
<220> FEATURE:
<221> NAME/KEY: misc_feature
<222> LOCATION: (5)..(5)
<223> OTHER INFORMATION: Val may be D-Val
<220> FEATURE:
<221> NAME/KEY: misc_feature
<222> LOCATION: (6)..(6)
<223> OTHER INFORMATION: Gln may be D-Gln
<220> FEATURE:
<221> NAME/KEY: misc_feature
<222> LOCATION: (7)..(7)
<223> OTHER INFORMATION: Pro may be D-Pro

<400> SEQUENCE: 97

Gly Gly Val Leu Val Gln Pro Gly
1               5

<210> SEQ ID NO 98
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (4)..(4)
<223> OTHER INFORMATION: Leu may be D-Leu
<220> FEATURE:
<221> NAME/KEY: misc_feature
<222> LOCATION: (5)..(5)
<223> OTHER INFORMATION: Val may be D-Val
<220> FEATURE:
<221> NAME/KEY: misc_feature
<222> LOCATION: (6)..(6)
<223> OTHER INFORMATION: Gln may be D-Gln

```
<220> FEATURE:
<221> NAME/KEY: misc_feature
<222> LOCATION: (7)..(7)
<223> OTHER INFORMATION: Pro may be D-Pro

<400> SEQUENCE: 98

Gly Gly Val Leu Val Gln Pro Gly
1               5

<210> SEQ ID NO 99
<211> LENGTH: 8
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Phe may be D-Phe

<400> SEQUENCE: 99

Gly Phe Val Leu Val Gln Pro Gly
1               5

<210> SEQ ID NO 100
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 100

Ala Pro Gly
1

<210> SEQ ID NO 101
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 101

Gln Ala Gly
1

<210> SEQ ID NO 102
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 102

Gln Pro Ala
1

<210> SEQ ID NO 103
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Gln may be D-Gln

<400> SEQUENCE: 103
```

```
Gln Pro Gly
1

<210> SEQ ID NO 104
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro

<400> SEQUENCE: 104

Gln Pro Gly
1

<210> SEQ ID NO 105
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Gln may be D-Gln
<220> FEATURE:
<221> NAME/KEY: misc_feature
<222> LOCATION: (2)..(2)
<223> OTHER INFORMATION: Pro may be D-Pro

<400> SEQUENCE: 105

Gln Pro Gly
1

<210> SEQ ID NO 106
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 106

Gly Pro Gln
1

<210> SEQ ID NO 107
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro

<400> SEQUENCE: 107

Gly Pro Gln
1

<210> SEQ ID NO 108
<211> LENGTH: 3
<212> TYPE: PRT
<213> ORGANISM: Artificial Sequence
<220> FEATURE:
<223> OTHER INFORMATION: Peptide permeability inhibitor
```

```
<220> FEATURE:
<221> NAME/KEY: misc_feature
<222> LOCATION: (3)..(3)
<223> OTHER INFORMATION: Gln may be D-Gln

<400> SEQUENCE: 108

Gly Pro Gln
1

<210> SEQ ID NO 109
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (3)..(3)
<223> OTHER INFORMATION: Gln may be D-Gln

<400> SEQUENCE: 109

Gly Pro Gln
1

<210> SEQ ID NO 110
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 110

Ala Pro Gly
1

<210> SEQ ID NO 111
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 111

His Pro Gly
1

<210> SEQ ID NO 112
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 112

Asp Pro Gly
1

<210> SEQ ID NO 113
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 113
```

Arg Pro Gly
1

<210> SEQ ID NO 114
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 114

Phe Pro Gly
1

<210> SEQ ID NO 115
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 115

Gly Pro Gly
1

<210> SEQ ID NO 116
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 116

Glu Pro Gly
1

<210> SEQ ID NO 117
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 117

Lys Pro Gly
1

<210> SEQ ID NO 118
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 118

Leu Pro Gly
1

<210> SEQ ID NO 119
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 119

Met Pro Gly
1

<210> SEQ ID NO 120
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 120

Asn Pro Gly
1

<210> SEQ ID NO 121
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 121

Ser Pro Gly
1

<210> SEQ ID NO 122
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 122

Tyr Pro Gly
1

<210> SEQ ID NO 123
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 123

Thr Pro Gly
1

<210> SEQ ID NO 124
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 124

Ile Pro Gly
1

<210> SEQ ID NO 125
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 125

Trp Pro Gly

```
<210> SEQ ID NO 126
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 126

Pro Pro Gly
1

<210> SEQ ID NO 127
<211> LENGTH: 3
<212> TYPE: PRT
<213> ORGANISM: Artificial Sequence
<220> FEATURE:
<223> OTHER INFORMATION: Peptide permeability inhibitor

<400> SEQUENCE: 127

Val Pro Gly
1

<210> SEQ ID NO 128
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 128

Xaa Pro Gly
1

<210> SEQ ID NO 129
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 129

Xaa Val Gly
1

<210> SEQ ID NO 130
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 130

Xaa Gln Gly
1
```

```
<210> SEQ ID NO 131
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 131

Xaa Ser Gly
1

<210> SEQ ID NO 132
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 132

Xaa Lys Gly
1

<210> SEQ ID NO 133
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 133

Xaa Phe Gly
1

<210> SEQ ID NO 134
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 134

Xaa Glu Gly
1

<210> SEQ ID NO 135
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid
```

```
<400> SEQUENCE: 135

Xaa Thr Gly
 1

<210> SEQ ID NO 136
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 136

Xaa Ile Gly
 1

<210> SEQ ID NO 137
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 137

Xaa Tyr Gly
 1

<210> SEQ ID NO 138
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 138

Xaa His Gly
 1

<210> SEQ ID NO 139
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 139

Xaa Asn Gly
 1

<210> SEQ ID NO 140
<211> LENGTH: 3
<212> TYPE: PRT
<213> ORGANISM: Artificial Sequence
```

```
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 140

Xaa Arg Gly
1

<210> SEQ ID NO 141
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 141

Xaa Gly Gly
1

<210> SEQ ID NO 142
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 142

Xaa Trp Gly
1

<210> SEQ ID NO 143
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 143

Xaa Asp Gly
1

<210> SEQ ID NO 144
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 144

Xaa Met Gly
1
```

```
<210> SEQ ID NO 145
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 145

Xaa Leu Gly
1

<210> SEQ ID NO 146
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 146

Xaa Pro Gln
1

<210> SEQ ID NO 147
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 147

Xaa Pro Asn
1

<210> SEQ ID NO 148
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 148

Xaa Pro Gln
1

<210> SEQ ID NO 149
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
```

```
<223> OTHER INFORMATION: Xaa may be L-pyroglutamic acid

<400> SEQUENCE: 149

Xaa Pro Ser
1

<210> SEQ ID NO 150
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 150

Xaa Pro Pro
1

<210> SEQ ID NO 151
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 151

Xaa Pro Trp
1

<210> SEQ ID NO 152
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 152

Xaa Pro Asp
1

<210> SEQ ID NO 153
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 153

Xaa Pro His
1

<210> SEQ ID NO 154
<211> LENGTH: 3
<212> TYPE: PRT
```

<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 154

Xaa Pro Leu
1

<210> SEQ ID NO 155
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 155

Xaa Pro Arg
1

<210> SEQ ID NO 156
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 156

Xaa Pro Val
1

<210> SEQ ID NO 157
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 157

Xaa Pro Lys
1

<210> SEQ ID NO 158
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 158

Xaa Pro Glu

```
<210> SEQ ID NO 159
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 159

Xaa Pro Phe
1

<210> SEQ ID NO 160
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 160

Xaa Pro Ile
1

<210> SEQ ID NO 161
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 161

Xaa Pro Met
1

<210> SEQ ID NO 162
<211> LENGTH: 3
<212> TYPE: PRT
<213> ORGANISM: Artificial Sequence
<220> FEATURE:
<223> OTHER INFORMATION: Peptide permeability inhibitor
<220> FEATURE:
<221> NAME/KEY: misc_feature
<222> LOCATION: (1)..(1)
<223> OTHER INFORMATION: Xaa may be L-pyroglutamic acid

<400> SEQUENCE: 162

Xaa Pro Tyr
1

<210> SEQ ID NO 163
<211> LENGTH: 9
<212> TYPE: PRT
<213> ORGANISM: Triticum sp.

<400> SEQUENCE: 163

Pro Tyr Pro Gln Pro Gln Leu Pro Tyr
```

<210> SEQ ID NO 164
<211> LENGTH: 13
<212> TYPE: PRT
<213> ORGANISM: Triticum sp.

<400> SEQUENCE: 164

Leu Gly Gln Gln Gln Pro Phe Pro Pro Gln Gln Pro Tyr
1               5                   10

<210> SEQ ID NO 165
<211> LENGTH: 290
<212> TYPE: PRT
<213> ORGANISM: Triticum aestivum

<400> SEQUENCE: 165

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Phe Pro
            20                  25                  30

Gly Gln Gln Gln Pro Phe Pro Pro Gln Gln Pro Tyr Pro Gln Pro Gln
            35                  40                  45

Pro Phe Pro Ser Gln Gln Pro Tyr Leu Gln Leu Gln Pro Phe Pro Gln
    50                  55                  60

Pro Gln Leu Pro Tyr Pro Gln Pro Gln Leu Pro Tyr Pro Gln Pro Gln
65                  70                  75                  80

Leu Pro Tyr Pro Gln Pro Gln Pro Phe Arg Pro Gln Gln Pro Tyr Pro
                85                  90                  95

Gln Ser Gln Pro Gln Tyr Ser Gln Pro Gln Gln Pro Ile Ser Gln Gln
            100                 105                 110

Gln Gln Gln Gln Gln Gln Gln Gln Gln Lys Gln Gln Gln Gln Gln
        115                 120                 125

Gln Gln Gln Ile Leu Gln Gln Ile Leu Gln Gln Gln Leu Ile Pro Cys
        130                 135                 140

Arg Asp Val Val Leu Gln Gln His Ser Ile Ala Tyr Gly Ser Ser Gln
145                 150                 155                 160

Val Leu Gln Gln Ser Thr Tyr Gln Leu Val Gln Gln Leu Cys Cys Gln
                165                 170                 175

Gln Leu Trp Gln Ile Pro Glu Gln Ser Arg Cys Gln Ala Ile His Asn
            180                 185                 190

Val Val His Ala Ile Ile Leu His Gln Gln Gln Gln Gln Gln Gln Gln
        195                 200                 205

Gln Gln Gln Gln Pro Leu Ser Gln Val Ser Phe Gln Gln Pro Gln Gln
    210                 215                 220

Gln Tyr Pro Ser Gly Gln Gly Ser Phe Gln Pro Ser Gln Gln Asn Pro
225                 230                 235                 240

Gln Ala Gln Gly Ser Val Gln Pro Gln Gln Leu Pro Gln Phe Glu Glu
                245                 250                 255

Ile Arg Asn Leu Ala Leu Glu Thr Leu Pro Ala Met Cys Asn Val Tyr
            260                 265                 270

Ile Pro Pro Tyr Cys Thr Ile Ala Pro Val Gly Ile Phe Gly Thr Asn
        275                 280                 285

Tyr Arg
    290

-continued

```
<210> SEQ ID NO 166
<211> LENGTH: 286
<212> TYPE: PRT
<213> ORGANISM: Triticum turgidum subsp. durum

<400> SEQUENCE: 166
```

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Arg Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Gln Pro Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Arg Tyr Ser Gln Pro Gln Gln
            100                 105                 110

Pro Ile Ser Gln Gln Gln Gln Gln His Gln Gln His Gln Gln His
        115                 120                 125

His Gln Glu Gln Gln Ile Leu Gln Gln Ile Leu Gln Gln Gln Leu Ile
130                 135                 140

Pro Cys Met Asp Val Val Leu Gln Gln His Asn Ile Ala His Arg Arg
145                 150                 155                 160

Ser Gln Val Leu Gln Gln Ser Thr Tyr Gln Leu Leu Gln Glu Leu Cys
                165                 170                 175

Cys Gln His Leu Trp Gln Ile Pro Glu Gln Ser Gln Cys Gln Ala Ile
            180                 185                 190

His Asn Val Val His Ala Ile Ile Pro His Gln Gln Lys Gln Gln
        195                 200                 205

Gln Gln Pro Ser Ser Gln Phe Ser Phe Gln Gln Pro Leu Gln Gln Tyr
    210                 215                 220

Pro Leu Gly Gln Gly Ser Phe Arg Pro Ser Gln Gln Asn Pro Gln Ala
225                 230                 235                 240

Gln Gly Ser Val Gln Pro Gln Gln Leu Pro Gln Phe Glu Glu Ile Arg
                245                 250                 255

Asn Leu Ala Leu Gln Thr Leu Pro Ala Met Cys Asn Val Tyr Ile Pro
            260                 265                 270

Pro Tyr Cys Thr Ile Ala Pro Phe Gly Ile Phe Gly Thr Asn
        275                 280                 285

```
<210> SEQ ID NO 167
<211> LENGTH: 286
<212> TYPE: PRT
<213> ORGANISM: Triticum aestivum

<400> SEQUENCE: 167
```

Met Lys Thr Phe Leu Ile Leu Val Leu Leu Ala Ile Val Ala Thr Thr
1               5                   10                  15

Ala Thr Thr Ala Val Arg Phe Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Gln Pro Phe Pro Pro Gln Gln Pro Tyr Pro

```
                    50                  55                  60
Gln Pro Gln Pro Phe Pro Ser Gln Leu Pro Tyr Leu Gln Leu Gln Pro
 65                  70                  75                  80

Phe Pro Gln Pro Gln Leu Pro Tyr Ser Gln Pro Gln Pro Phe Arg Pro
                     85                  90                  95

Gln Gln Pro Tyr Pro Gln Pro Gln Pro Gln Tyr Ser Gln Pro Gln Gln
                100                 105                 110

Pro Ile Ser Gln Gln Gln Gln Gln Gln Gln Gln Gln Gln Gln Gln Gln
                115                 120                 125

Gln Gln Gln Gln Gln Ile Leu Gln Gln Ile Leu Gln Gln Gln Leu Ile
            130                 135                 140

Pro Cys Met Asp Val Val Leu Gln Gln His Asn Ile Ala His Gly Arg
145                 150                 155                 160

Ser Gln Val Leu Gln Gln Ser Thr Tyr Gln Leu Leu Gln Glu Leu Cys
                165                 170                 175

Cys Gln His Leu Trp Gln Ile Pro Glu Gln Ser Gln Cys Gln Ala Ile
                180                 185                 190

His Asn Val Val His Ala Ile Ile Leu His Gln Gln Gln Lys Gln Gln
                195                 200                 205

Gln Gln Pro Ser Ser Gln Val Ser Phe Gln Gln Pro Leu Gln Gln Tyr
            210                 215                 220

Pro Leu Gly Gln Gly Ser Phe Arg Pro Ser Gln Gln Asn Pro Gln Ala
225                 230                 235                 240

Gln Gly Ser Val Gln Pro Gln Gln Leu Pro Gln Phe Glu Glu Ile Arg
                245                 250                 255

Asn Leu Ala Leu Gln Thr Leu Pro Ala Met Cys Asn Val Tyr Ile Pro
                260                 265                 270

Pro Tyr Cys Thr Ile Ala Pro Phe Gly Ile Phe Gly Thr Asn
                275                 280                 285

<210> SEQ ID NO 168
<211> LENGTH: 302
<212> TYPE: PRT
<213> ORGANISM: Triticum aestivum

<400> SEQUENCE: 168

Met Lys Thr Leu Leu Ile Leu Thr Ile Leu Ala Met Ala Thr Thr Ile
 1                   5                  10                  15

Ala Thr Ala Asn Met Gln Val Asp Pro Ser Gly Gln Val Gln Trp Pro
                 20                  25                  30

Gln Gln Gln Pro Phe Pro Gln Pro Gln Gln Pro Phe Cys Gln Gln Pro
                 35                  40                  45

Gln Arg Thr Ile Pro Gln Pro His Gln Thr Phe His His Gln Pro Gln
             50                  55                  60

Gln Thr Phe Pro Gln Pro Gln Gln Thr Tyr Pro His Gln Pro Gln Gln
 65                  70                  75                  80

Gln Phe Pro Gln Thr Gln Gln Pro Gln Gln Phe Pro Gln Pro Pro Gln
                 85                  90                  95

Gln Thr Phe Pro Gln Gln Pro Gln Leu Pro Phe Pro Gln Gln Pro Gln
                100                 105                 110

Gln Pro Phe Pro Gln Pro Gln Gln Pro Gln Gln Pro Phe Pro Gln Ser
            115                 120                 125

Gln Gln Pro Gln Gln Pro Phe Pro Gln Pro Gln Gln Gln Phe Pro Gln
            130                 135                 140
```

```
Pro Gln Gln Pro Gln Gln Ser Phe Pro Gln Gln Gln Pro Ala Ile
145                 150                 155                 160

Gln Ser Phe Leu Gln Gln Met Asn Pro Cys Lys Asn Phe Leu Leu
            165                 170                 175

Gln Gln Cys Asn His Val Ser Leu Val Ser Ser Leu Val Ser Ile Ile
        180                 185                 190

Leu Pro Arg Ser Asp Cys Gln Val Met Gln Gln Cys Cys Gln Gln
        195                 200                 205

Leu Ala Gln Ile Pro Gln Gln Leu Gln Cys Ala Ala Ile His Ser Val
    210                 215                 220

Ala His Ser Ile Ile Met Gln Gln Glu Gln Gln Gln Gly Val Pro Ile
225                 230                 235                 240

Leu Arg Pro Leu Phe Gln Leu Ala Gln Gly Leu Gly Ile Ile Gln Pro
            245                 250                 255

Gln Gln Pro Ala Gln Leu Glu Gly Ile Arg Ser Leu Val Leu Lys Thr
            260                 265                 270

Leu Pro Thr Met Cys Asn Val Tyr Val Pro Pro Asp Cys Ser Thr Ile
            275                 280                 285

Asn Val Pro Tyr Ala Asn Ile Asp Ala Gly Ile Gly Gly Gln
            290                 295                 300

<210> SEQ ID NO 169
<211> LENGTH: 291
<212> TYPE: PRT
<213> ORGANISM: Triticum aestivum

<400> SEQUENCE: 169

Met Lys Thr Leu Leu Ile Leu Thr Ile Leu Ala Met Ala Ile Thr Ile
1               5                   10                  15

Ala Thr Ala Asn Met Gln Ala Asp Pro Ser Gly Gln Val Gln Trp Pro
            20                  25                  30

Gln Gln Gln Pro Phe Leu Gln Pro His Gln Pro Phe Ser Gln Gln Pro
        35                  40                  45

Gln Gln Ile Phe Pro Gln Pro Gln Gln Thr Phe Pro His Gln Pro Gln
    50                  55                  60

Gln Gln Phe Pro Gln Pro Gln Gln Pro Gln Gln Gln Phe Leu Gln Pro
65                  70                  75                  80

Arg Gln Pro Phe Pro Gln Gln Pro Gln Gln Pro Tyr Pro Gln Gln Pro
            85                  90                  95

Gln Gln Pro Phe Pro Gln Thr Gln Gln Pro Gln Gln Pro Phe Pro Gln
        100                 105                 110

Ser Lys Gln Pro Gln Gln Pro Phe Pro Gln Pro Gln Gln Pro Gln Gln
    115                 120                 125

Ser Phe Pro Gln Gln Pro Ser Leu Ile Gln Gln Ser Leu Gln Gln
130                 135                 140

Gln Leu Asn Pro Cys Lys Asn Phe Leu Leu Gln Gln Cys Lys Pro Val
145                 150                 155                 160

Ser Leu Val Ser Ser Leu Trp Ser Ile Ile Leu Pro Pro Ser Asp Cys
            165                 170                 175

Gln Val Met Arg Gln Gln Cys Cys Gln Gln Leu Ala Gln Ile Pro Gln
            180                 185                 190

Gln Leu Gln Cys Ala Ala Ile His Ser Val Val His Ser Ile Ile Met
        195                 200                 205

Gln Gln Glu Gln Gln Glu Gln Leu Gln Gly Val Gln Ile Leu Val Pro
    210                 215                 220
```

```
Leu Ser Gln Gln Gln Val Gly Gln Gly Ile Leu Val Gly Gln
225                 230                 235                 240

Gly Ile Ile Gln Pro Gln Pro Ala Gln Leu Glu Val Ile Arg Ser
            245                 250                 255

Leu Val Leu Gln Thr Leu Pro Thr Met Cys Asn Val Tyr Val Pro Pro
                260                 265                 270

Tyr Cys Ser Thr Ile Arg Ala Pro Phe Ala Ser Ile Val Ala Ser Ile
            275                 280                 285

Gly Gly Gln
    290

<210> SEQ ID NO 170
<211> LENGTH: 244
<212> TYPE: PRT
<213> ORGANISM: Triticum aestivum

<400> SEQUENCE: 170

Pro Gln Gln Pro Phe Pro Leu Gln Pro Gln Gln Ser Phe Leu Trp Gln
1               5                   10                  15

Ser Gln Gln Pro Phe Leu Gln Pro Gln Gln Pro Ser Pro Gln Pro
            20                  25                  30

Gln Gln Val Val Gln Ile Ile Ser Pro Ala Thr Pro Thr Thr Ile Pro
        35                  40                  45

Ser Ala Gly Lys Pro Thr Ser Ala Pro Phe Pro Gln Gln Gln Gln
50                  55                  60

His Gln Gln Leu Ala Gln Gln Ile Pro Val Val Gln Pro Ser Ile
65              70                  75                  80

Leu Gln Gln Leu Asn Pro Cys Lys Val Phe Leu Gln Gln Cys Ser
                85                  90                  95

Pro Val Ala Met Pro Gln Arg Leu Ala Arg Ser Gln Met Leu Gln Gln
                100                 105                 110

Ser Ser Cys His Val Met Gln Gln Cys Cys Gln Gln Leu Pro Gln
            115                 120                 125

Ile Pro Gln Gln Ser Arg Tyr Gln Ala Ile Arg Ala Ile Ile Tyr Ser
130                 135                 140

Ile Ile Leu Gln Glu Gln Gln Val Gln Gly Ser Ile Gln Ser Gln
145             150                 155                 160

Gln Gln Gln Pro Gln Gln Leu Gly Gln Cys Val Ser Gln Pro Gln Gln
                165                 170                 175

Gln Ser Gln Gln Gln Leu Gly Gln Pro Gln Gln Gln Leu Ala
            180                 185                 190

Gln Gly Thr Phe Leu Gln Pro His Gln Ile Ala Gln Leu Glu Val Met
            195                 200                 205

Thr Ser Ile Ala Leu Arg Ile Leu Pro Thr Met Cys Ser Val Asn Val
210                 215                 220

Pro Leu Tyr Arg Thr Thr Thr Ser Val Pro Phe Gly Val Gly Thr Gly
225                 230                 235                 240

Val Gly Ala Tyr

<210> SEQ ID NO 171
<211> LENGTH: 327
<212> TYPE: PRT
<213> ORGANISM: Triticum aestivum

<400> SEQUENCE: 171
```

-continued

Met Lys Thr Leu Leu Ile Leu Thr Ile Leu Ala Met Ala Ile Thr Ile
1               5                   10                  15

Gly Thr Ala Asn Ile Gln Val Asp Pro Ser Gly Gln Val Gln Trp Leu
                20                  25                  30

Gln Gln Gln Leu Val Pro Gln Leu Gln Gln Pro Leu Ser Gln Gln Pro
            35                  40                  45

Gln Gln Thr Phe Pro Gln Pro Gln Thr Phe Pro His Gln Pro Gln
    50                  55                  60

Gln Gln Val Pro Gln Pro Gln Gln Pro Gln Gln Pro Phe Leu Gln Pro
65                  70                  75                  80

Gln Gln Pro Phe Pro Gln Gln Pro Gln Gln Pro Phe Pro Gln Thr Gln
                85                  90                  95

Gln Pro Gln Gln Pro Phe Pro Gln Gln Pro Gln Gln Pro Phe Pro Gln
                100                 105                 110

Thr Gln Gln Pro Gln Gln Pro Phe Pro Gln Gln Pro Gln Gln Pro Phe
            115                 120                 125

Pro Gln Thr Gln Gln Pro Gln Gln Pro Phe Pro Gln Leu Gln Gln Pro
            130                 135                 140

Gln Gln Pro Phe Pro Gln Pro Gln Gln Leu Pro Gln Pro Gln Gln
145                 150                 155                 160

Pro Gln Gln Ser Phe Pro Gln Gln Arg Pro Phe Ile Gln Pro Ser
                165                 170                 175

Leu Gln Gln Gln Leu Asn Pro Cys Lys Asn Ile Leu Leu Gln Gln Ser
                180                 185                 190

Lys Pro Ala Ser Leu Val Ser Ser Leu Trp Ser Ile Ile Trp Pro Gln
                195                 200                 205

Ser Asp Cys Gln Val Met Arg Gln Gln Cys Cys Gln Gln Leu Ala Gln
    210                 215                 220

Ile Pro Gln Gln Leu Gln Cys Ala Ala Ile His Ser Val Val His Ser
225                 230                 235                 240

Ile Ile Met Gln Gln Gln Gln Gln Gln Gln Gln Gly Ile Asp
                245                 250                 255

Ile Phe Leu Pro Leu Ser Gln His Glu Gln Val Gly Gln Gly Ser Leu
                260                 265                 270

Val Gln Gly Gln Gly Ile Ile Gln Pro Gln Gln Pro Ala Gln Leu Glu
            275                 280                 285

Ala Ile Arg Ser Leu Val Leu Gln Thr Leu Pro Ser Met Cys Asn Val
            290                 295                 300

Tyr Val Pro Pro Glu Cys Ser Ile Met Arg Ala Pro Phe Ala Ser Ile
305                 310                 315                 320

Val Ala Gly Ile Gly Gly Gln
                325

<210> SEQ ID NO 172
<211> LENGTH: 304
<212> TYPE: PRT
<213> ORGANISM: Triticum aestivum

<400> SEQUENCE: 172

Met Lys Thr Phe Leu Val Phe Ala Leu Ile Ala Val Ala Thr Ser
1               5                   10                  15

Ala Ile Ala Gln Met Glu Thr Ser Cys Ile Ser Gly Leu Glu Arg Pro
                20                  25                  30

Trp Gln Gln Pro Leu Pro Pro Gln Gln Ser Phe Ser Gln Gln Pro
            35                  40                  45

```
Pro Phe Ser Gln Gln Gln Gln Pro Leu Pro Gln Pro Ser Phe
        50                  55                  60

Ser Gln Gln Gln Pro Pro Phe Ser Gln Gln Gln Pro Ile Leu Ser Gln
 65              70                  75                  80

Gln Pro Pro Phe Ser Gln Gln Gln Pro Val Leu Pro Gln Gln Ser
                85                  90                  95

Pro Phe Ser Gln Gln Gln Leu Val Leu Pro Gln Gln Gln
                100                 105                 110

Gln Gln Leu Val Gln Gln Ile Pro Ile Val Gln Pro Ser Val Leu
        115                 120                 125

Gln Gln Leu Asn Pro Cys Lys Val Phe Leu Gln Gln Cys Ser Pro
        130                 135                 140

Val Ala Met Pro Gln Arg Leu Ala Arg Ser Gln Met Trp Gln Gln Ser
145                 150                 155                 160

Ser Cys His Val Met Gln Gln Cys Cys Gln Gln Leu Gln Gln Ile
                165                 170                 175

Pro Glu Gln Ser Arg Tyr Glu Ala Ile Arg Ala Ile Ile Tyr Ser Ile
                180                 185                 190

Ile Leu Gln Glu Gln Gln Gly Phe Val Pro Gln Gln Gln Gln
        195                 200                 205

Pro Gln Gln Ser Gly Gln Gly Val Ser Gln Ser Gln Gln Ser Gln
        210                 215                 220

Gln Gln Leu Gly Gln Cys Ser Phe Gln Gln Pro Gln Gln Leu Gly
225                 230                 235                 240

Gln Gln Pro Gln Gln Gln Gln Gln Val Leu Gln Gly Thr Phe
                245                 250                 255

Leu Gln Pro His Gln Ile Ala His Leu Glu Ala Val Thr Ser Ile Ala
                260                 265                 270

Leu Arg Thr Leu Pro Thr Met Cys Ser Val Asn Val Pro Leu Tyr Ser
        275                 280                 285

Ala Thr Thr Ser Val Pro Phe Gly Val Gly Thr Gly Val Gly Ala Tyr
        290                 295                 300

<210> SEQ ID NO 173
<211> LENGTH: 251
<212> TYPE: PRT
<213> ORGANISM: Triticum aestivum

<400> SEQUENCE: 173

Met Lys Thr Leu Leu Ile Leu Thr Ile Leu Ala Met Ala Ile Thr Ile
 1               5                  10                  15

Gly Thr Ala Asn Met Gln Val Asp Pro Ser Ser Gln Val Gln Trp Pro
        20                  25                  30

Gln Gln Gln Pro Val Pro Gln Pro His Gln Pro Phe Ser Gln Gln Pro
        35                  40                  45

Gln Gln Thr Phe Pro Gln Pro Gln Gln Thr Phe Pro His Gln Pro Gln
        50                  55                  60

Gln Gln Phe Pro Gln Pro Gln Gln Pro Gln Gln Phe Leu Gln Pro
 65              70                  75                  80

Gln Gln Pro Phe Pro Gln Gln Pro Gln Pro Tyr Pro Gln Gln Pro
                85                  90                  95

Gln Gln Pro Phe Pro Gln Thr Gln Gln Pro Gln Gln Leu Phe Pro Gln
                100                 105                 110

Ser Gln Gln Pro Gln Gln Gln Phe Ser Gln Pro Gln Gln Gln Phe Pro
```

```
              115                 120                 125
Gln Pro Gln Gln Pro Gln Gln Ser Phe Pro Gln Gln Pro Pro Phe
        130                 135                 140
Ile Gln Pro Ser Leu Gln Gln Val Asn Pro Cys Lys Asn Phe Leu
145                 150                 155                 160
Leu Gln Gln Cys Lys Pro Val Ser Leu Val Ser Ser Leu Trp Ser Met
                165                 170                 175
Ile Trp Pro Gln Ser Asp Cys Gln Val Met Arg Gln Gln Cys Cys Gln
            180                 185                 190
Gln Leu Ala Gln Ile Pro Gln Gln Leu Gln Cys Ala Ala Ile His Thr
        195                 200                 205
Ile Ile His Ser Ile Ile Met Gln Gln Glu Gln Gln Glu Gln Gln Gln
        210                 215                 220
Gly Met His Ile Leu Leu Pro Leu Tyr Gln Gln Gln Gln Val Gly Gln
225                 230                 235                 240
Gly Thr Leu Val Gln Gly Gln Gly Ile Ile Gln
                    245                 250

<210> SEQ ID NO 174
<211> LENGTH: 307
<212> TYPE: PRT
<213> ORGANISM: Triticum aestivum

<400> SEQUENCE: 174

Met Lys Thr Phe Leu Ile Leu Ala Leu Leu Ala Ile Val Ala Thr Thr
1               5                   10                  15
Ala Arg Ile Ala Val Arg Val Pro Val Pro Gln Leu Gln Pro Gln Asn
            20                  25                  30
Pro Ser Gln Gln Gln Pro Gln Glu Gln Val Pro Leu Val Gln Gln Gln
        35                  40                  45
Gln Phe Pro Gly Gln Gln Gln Pro Phe Pro Pro Gln Gln Pro Tyr Pro
    50                  55                  60
Gln Pro Gln Pro Phe Pro Ser Gln Gln Pro Tyr Leu Gln Leu Gln Pro
65                  70                  75                  80
Phe Pro Gln Pro Gln Leu Pro Tyr Pro Gln Pro Gln Leu Pro Tyr Pro
                85                  90                  95
Gln Pro Gln Leu Pro Tyr Pro Gln Pro Gln Pro Phe Arg Pro Gln Gln
            100                 105                 110
Pro Tyr Pro Gln Ser Gln Pro Gln Tyr Ser Gln Pro Gln Gln Pro Ile
        115                 120                 125
Ser Gln Gln Gln Gln Gln Gln Gln Gln Gln Gln Gln Lys Gln Gln
130                 135                 140
Gln Gln Gln Gln Gln Ile Leu Gln Gln Ile Leu Gln Gln Gln Leu
145                 150                 155                 160
Ile Pro Cys Arg Asp Val Val Leu Gln Gln His Ser Ile Ala Tyr Gly
                165                 170                 175
Ser Ser Gln Val Leu Gln Gln Ser Thr Tyr Gln Leu Val Gln Gln Leu
            180                 185                 190
Cys Cys Gln Gln Leu Trp Gln Ile Pro Glu Gln Ser Arg Cys Gln Ala
        195                 200                 205
Ile His Asn Val Val His Ala Ile Ile Leu His Gln Gln Gln Gln
        210                 215                 220
Gln Gln Gln Gln Gln Gln Gln Pro Leu Ser Gln Val Ser Phe Gln Gln
225                 230                 235                 240
```

```
Pro Gln Gln Gln Tyr Pro Ser Gly Gln Gly Ser Phe Gln Pro Ser Gln
                245                 250                 255

Gln Asn Pro Gln Ala Gln Gly Ser Val Gln Pro Gln Leu Pro Gln
        260                 265                 270

Phe Glu Glu Ile Arg Asn Leu Ala Leu Glu Thr Leu Pro Ala Met Cys
            275                 280                 285

Asn Val Tyr Ile Pro Pro Tyr Cys Thr Ile Ala Pro Val Gly Ile Phe
        290                 295                 300

Gly Thr Asn
305

<210> SEQ ID NO 175
<211> LENGTH: 186
<212> TYPE: PRT
<213> ORGANISM: Triticum aestivum

<400> SEQUENCE: 175

Pro Gln Pro Gln Pro Gln Tyr Ser Gln Pro Gln Gln Pro Ile Ser Gln
1               5                   10                  15

Gln Gln Gln Gln Gln Gln Gln Gln Gln Gln Gln Gln Gln Gln Glu Gln
            20                  25                  30

Gln Ile Leu Gln Gln Ile Leu Gln Gln Gln Leu Ile Pro Cys Met Asp
        35                  40                  45

Val Val Leu Gln Gln His Asn Ile Ala His Gly Arg Ser Gln Val Leu
    50                  55                  60

Gln Gln Ser Thr Tyr Gln Leu Leu Gln Glu Leu Cys Cys Gln His Leu
65                  70                  75                  80

Trp Gln Ile Pro Glu Gln Ser Gln Cys Gln Ala Ile His Asn Val Val
                85                  90                  95

His Ala Ile Ile Leu His Gln Gln Gln Lys Gln Gln Gln Gln Gln Pro
            100                 105                 110

Ser Ser Gln Phe Ser Phe Gln Gln Pro Leu Gln Gln Tyr Pro Leu Gly
        115                 120                 125

Gln Gly Ser Phe Arg Pro Ser Gln Gln Asn Pro Gln Ala Gln Gly Ser
    130                 135                 140

Val Gln Pro Gln Gln Leu Pro Gln Phe Glu Ile Arg Asn Leu Ala Leu
145                 150                 155                 160

Gln Thr Leu Pro Ala Met Cys Asn Val Tyr Ile Pro Pro Tyr Cys Thr
                165                 170                 175

Ile Ala Pro Phe Gly Ile Phe Gly Thr Asn
            180                 185

<210> SEQ ID NO 176
<211> LENGTH: 313
<212> TYPE: PRT
<213> ORGANISM: Triticum aestivum

<400> SEQUENCE: 176

Met Lys Thr Phe Leu Ile Leu Ala Leu Val Ala Thr Thr Ala Thr Thr
1               5                   10                  15

Ala Val Arg Val Pro Val Pro Gln Leu Gln Pro Lys Asn Pro Ser Gln
            20                  25                  30

Gln Gln Pro Gln Glu Gln Val Pro Leu Val Gln Gln Gln Gln Phe Pro
        35                  40                  45

Gly Gln Gln Gln Gln Phe Pro Pro Gln Gln Pro Tyr Pro Gln Pro Gln
    50                  55                  60
```

```
Pro Phe Pro Ser Gln Gln Pro Tyr Leu Gln Leu Gln Pro Phe Pro Gln
 65                  70                  75                  80

Pro Gln Pro Phe Leu Pro Gln Leu Pro Tyr Pro Gln Pro Gln Ser Phe
                 85                  90                  95

Pro Pro Gln Gln Pro Tyr Pro Gln Gln Arg Pro Lys Tyr Leu Gln Pro
            100                 105                 110

Gln Gln Pro Ile Ser Gln Gln Ala Gln Gln Gln Gln Gln Gln Gln Gln
        115                 120                 125

Gln Gln Gln Gln Gln Gln Gln Gln Gln Ile Leu Gln Gln Ile Leu
130                 135                 140

Gln Gln Gln Leu Ile Pro Cys Arg Asp Val Val Leu Gln Gln His Asn
145                 150                 155                 160

Ile Ala His Ala Ser Ser Gln Val Leu Gln Gln Ser Thr Tyr Gln Leu
                165                 170                 175

Leu Gln Gln Leu Cys Cys Gln Gln Leu Leu Gln Ile Pro Glu Gln Ser
                180                 185                 190

Arg Cys Gln Ala Ile His Asn Val Val His Ala Ile Ile Met His Gln
            195                 200                 205

Gln Glu Gln Gln Gln Gln Leu Gln Gln Gln Gln Gln Gln Gln Leu Gln
    210                 215                 220

Gln Gln Gln Gln Gln Gln Gln Gln Gln Pro Ser Ser Gln Val
225                 230                 235                 240

Ser Phe Gln Gln Pro Gln Gln Tyr Pro Ser Ser Gln Gly Ser Phe
                245                 250                 255

Gln Pro Ser Gln Gln Asn Pro Gln Ala Gln Gly Ser Val Gln Pro Gln
            260                 265                 270

Gln Leu Pro Gln Phe Ala Glu Ile Arg Asn Leu Ala Leu Gln Thr Leu
    275                 280                 285

Pro Ala Met Cys Asn Val Tyr Ile Pro Pro His Cys Ser Thr Thr Ile
290                 295                 300

Ala Pro Phe Gly Ile Phe Gly Thr Asn
305                 310

<210> SEQ ID NO 177
<211> LENGTH: 296
<212> TYPE: PRT
<213> ORGANISM: Triticum aestivum

<400> SEQUENCE: 177

Met Lys Thr Phe Leu Ile Leu Ala Leu Leu Ala Ile Val Ala Thr Thr
 1               5                  10                  15

Ala Thr Thr Ala Val Arg Val Pro Val Pro Gln Pro Gln Pro Gln Asn
                20                  25                  30

Pro Ser Gln Pro Gln Pro Gln Gly Gln Val Pro Leu Val Gln Gln Gln
            35                  40                  45

Gln Phe Pro Gly Gln Gln Gln Gln Phe Pro Pro Gln Gln Pro Tyr Pro
        50                  55                  60

Gln Pro Gln Pro Phe Pro Ser Gln Gln Pro Tyr Leu Gln Leu Gln Pro
 65                  70                  75                  80

Phe Pro Gln Pro Gln Pro Phe Pro Gln Leu Pro Tyr Pro Gln Pro Pro
                85                  90                  95

Pro Pro Phe Ser Pro Gln Gln Pro Tyr Pro Gln Pro Gln Pro Gln Tyr
            100                 105                 110

Pro Gln Pro Gln Gln Pro Ile Ser Gln Gln Ala Gln Gln Gln Gln Gln
        115                 120                 125
```

```
Gln Gln Gln Gln Gln Gln Gln Gln Gln Gln Gln Gln Ile Leu
130                 135                 140

Gln Gln Ile Leu Gln Gln Leu Ile Pro Cys Arg Asp Val Val Leu
145                 150                 155                 160

Gln Gln His Asn Ile Ala His Ala Arg Ser Gln Val Leu Gln Ser
                165                 170                 175

Thr Tyr Gln Pro Leu Gln Gln Leu Cys Cys Gln Gln Leu Trp Gln Ile
                180                 185                 190

Pro Glu Gln Ser Arg Cys Gln Ala Ile His Asn Val Val His Ala Ile
                195                 200                 205

Ile Leu His Gln Gln Arg Gln Gln Pro Ser Ser Gln Val Ser
210                 215                 220

Leu Gln Gln Pro Gln Gln Tyr Pro Ser Gly Gln Gly Phe Phe Gln
225                 230                 235                 240

Pro Ser Gln Gln Asn Pro Gln Ala Gln Gly Ser Val Gln Pro Gln Gln
                245                 250                 255

Leu Pro Gln Phe Glu Glu Ile Arg Asn Leu Ala Leu Gln Thr Leu Pro
                260                 265                 270

Arg Met Cys Asn Val Tyr Ile Pro Pro Tyr Cys Ser Thr Thr Ile Ala
                275                 280                 285

Pro Phe Gly Ile Phe Gly Thr Asn
290                 295

<210> SEQ ID NO 178
<211> LENGTH: 297
<212> TYPE: PRT
<213> ORGANISM: Triticum aestivum

<400> SEQUENCE: 178

Met Lys Thr Phe Leu Ile Leu Ala Leu Arg Ala Ile Val Ala Thr Thr
1               5                   10                  15

Ala Thr Ile Ala Val Arg Val Pro Val Pro Gln Leu Gln Pro Gln Asn
                20                  25                  30

Pro Ser Gln Gln Gln Pro Gln Lys Gln Val Pro Leu Val Gln Gln Gln
                35                  40                  45

Gln Phe Pro Gly Gln Gln Gln Pro Phe Pro Gln Gln Pro Tyr Pro
50                  55                  60

Gln Gln Gln Pro Phe Pro Ser Gln Gln Pro Tyr Met Gln Leu Gln Pro
65                  70                  75                  80

Phe Pro Gln Pro Gln Leu Pro Tyr Pro Gln Pro Gln Leu Pro Tyr Pro
                85                  90                  95

Gln Pro Gln Pro Phe Arg Pro Gln Gln Ser Tyr Pro Gln Pro Gln Pro
                100                 105                 110

Gln Tyr Ser Gln Pro Gln Gln Pro Ile Ser Gln Gln Gln Gln Gln
                115                 120                 125

Gln Gln Gln Gln Gln Gln Gln Gln Ile Leu Gln Gln Ile Leu Gln
130                 135                 140

Gln Gln Leu Ile Pro Cys Arg Asp Val Val Leu Gln Gln His Ser Ile
145                 150                 155                 160

Ala His Gly Ser Ser Gln Val Leu Gln Gln Ser Thr Tyr Gln Leu Val
                165                 170                 175

Gln Gln Phe Cys Cys Gln Gln Leu Trp Gln Ile Pro Glu Gln Ser Arg
                180                 185                 190

Cys Gln Ala Ile His Asn Val Val His Ala Ile Ile Leu His Gln Gln
```

```
              195                 200                 205
Gln Gln Gln Gln Gln Gln Gln Gln Gln Gln Gln Pro Leu Ser
        210                 215                 220

Gln Val Cys Phe Gln Gln Ser Gln Gln Tyr Pro Ser Gly Gln Gly
225                 230                 235                 240

Ser Phe Gln Pro Ser Gln Gln Asn Pro Gln Ala Gln Gly Ser Val Gln
                245                 250                 255

Pro Gln Gln Leu Pro Gln Phe Glu Glu Ile Arg Asn Leu Ala Leu Glu
            260                 265                 270

Thr Leu Pro Ala Met Cys Asn Val Tyr Ile Pro Pro Tyr Cys Thr Ile
            275                 280                 285

Ala Pro Val Gly Ile Phe Gly Thr Asn
            290                 295

<210> SEQ ID NO 179
<211> LENGTH: 282
<212> TYPE: PRT
<213> ORGANISM: Triticum aestivum

<400> SEQUENCE: 179

Met Lys Thr Phe Leu Ile Leu Ala Leu Leu Ala Ile Val Ala Thr Thr
1               5                  10                  15

Ala Thr Ser Ala Val Arg Val Pro Val Pro Gln Leu Gln Pro Gln Asn
            20                  25                  30

Pro Ser Gln Gln Gln Pro Gln Glu Gln Val Pro Leu Met Gln Gln Gln
        35                  40                  45

Gln Gln Phe Pro Gly Gln Gln Glu Gln Phe Pro Pro Gln Gln Pro Tyr
    50                  55                  60

Pro His Gln Gln Pro Phe Pro Ser Gln Gln Pro Tyr Pro Gln Pro Gln
65                  70                  75                  80

Pro Phe Pro Pro Gln Leu Pro Tyr Pro Gln Thr Gln Pro Phe Pro Pro
                85                  90                  95

Gln Gln Pro Tyr Pro Gln Pro Gln Pro Gln Tyr Pro Gln Pro Gln Gln
            100                 105                 110

Pro Ile Ser Gln Gln Gln Ala Gln Gln Gln Gln Gln Gln Gln Gln Thr
        115                 120                 125

Leu Gln Gln Ile Leu Gln Gln Gln Leu Ile Pro Cys Arg Asp Val Val
    130                 135                 140

Leu Gln Gln His Asn Ile Ala His Ala Ser Ser Gln Val Leu Gln Gln
145                 150                 155                 160

Ser Ser Tyr Gln Gln Leu Gln Gln Leu Cys Cys Gln Gln Leu Phe Gln
                165                 170                 175

Ile Pro Glu Gln Ser Arg Cys Gln Ala Ile His Asn Val Val His Ala
            180                 185                 190

Ile Ile Leu His His Gln Gln Gln Gln Gln Gln Gln Pro Ser Ser Gln
        195                 200                 205

Val Ser Tyr Gln Gln Pro Gln Glu Gln Tyr Pro Ser Gly Gln Val Ser
    210                 215                 220

Phe Gln Ser Ser Gln Gln Asn Pro Gln Ala Gln Gly Ser Val Gln Pro
225                 230                 235                 240

Gln Gln Leu Pro Gln Phe Gln Glu Ile Arg Asn Leu Ala Leu Gln Thr
                245                 250                 255

Leu Pro Ala Met Cys Asn Val Tyr Ile Pro Pro Tyr Cys Ser Thr Thr
            260                 265                 270
```

-continued

Ile Ala Pro Phe Gly Ile Phe Gly Thr Asn
        275                 280

<210> SEQ ID NO 180
<211> LENGTH: 291
<212> TYPE: PRT
<213> ORGANISM: Triticum aestivum

<400> SEQUENCE: 180

Met Lys Thr Phe Pro Ile Leu Ala Leu Leu Ala Ile Val Ala Thr Thr
1               5                   10                  15

Ala Thr Thr Ala Val Arg Val Pro Val Pro Gln Leu Gln Leu Gln Asn
            20                  25                  30

Pro Ser Gln Gln Gln Pro Gln Glu Gln Val Pro Leu Val Gln Glu Gln
        35                  40                  45

Gln Phe Gln Gly Gln Gln Gln Pro Phe Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Pro Gln Pro Gln Pro Phe Arg Pro
                85                  90                  95

Gln Gln Pro Tyr Pro Gln Pro Gln Pro Tyr Ser Gln Pro Gln Gln
            100                 105                 110

Pro Ile Ser Gln Gln Gln Gln Gln Gln Gln Gln Gln Gln Gln Gln
        115                 120                 125

Gln Gln Ile Leu Gln Gln Ile Leu Gln Gln Gln Leu Ile Pro Cys Arg
    130                 135                 140

Asp Val Val Leu Gln Gln His Asn Ile Ala His Gly Ser Ser Gln Val
145                 150                 155                 160

Leu Gln Glu Ser Thr Tyr Gln Leu Val Gln Gln Leu Cys Cys Gln Gln
                165                 170                 175

Leu Trp Gln Ile Pro Glu Gln Ser Arg Cys Gln Ala Ile His Asn Val
            180                 185                 190

Val His Ala Ile Ile Leu His Gln Gln His His Gln Gln Gln
        195                 200                 205

Gln Gln Gln Gln Gln Gln Pro Leu Ser Gln Val Ser Phe Gln Gln
    210                 215                 220

Pro Gln Gln Gln Tyr Pro Ser Gly Gln Gly Phe Phe Gln Pro Ser Gln
225                 230                 235                 240

Gln Asn Pro Gln Ala Gln Gly Ser Phe Gln Pro Gln Gln Leu Pro Gln
                245                 250                 255

Phe Glu Glu Ile Arg Asn Leu Ala Leu Gln Thr Leu Pro Ala Met Cys
            260                 265                 270

Asn Val Tyr Ile Pro Pro Tyr Cys Thr Ile Ala Pro Phe Gly Ile Phe
        275                 280                 285

Gly Thr Asn
    290

<210> SEQ ID NO 181
<211> LENGTH: 262
<212> TYPE: PRT
<213> ORGANISM: Triticum aestivum

<400> SEQUENCE: 181

Met Lys Thr Phe Leu Ile Leu Ala Leu Leu Ala Ile Val Ala Thr Thr
1               5                   10                  15

```
Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Gln Pro Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Leu Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Gln Ile Ile Gln Gln Ile Leu Gln Gln Gln Leu
    130                 135                 140

Ile Pro Cys Met Asp Val Val Leu Gln Gln His Asn Ile Val His Gly
145                 150                 155                 160

Lys Ser Gln Val Leu Gln Gln Ser Thr Tyr Gln Leu Leu Gln Glu Leu
                165                 170                 175

Cys Cys Gln His Leu Trp Gln Ile Pro Glu Gln Ser Gln Cys Gln Ala
            180                 185                 190

Ile His Asn Val Val His Ala Ile Ile Leu His Gln Gln Gln Lys Gln
        195                 200                 205

Gln Gln Gln Pro Ser Ser Gln Val Ser Phe Gln Pro Leu Gln Gln
    210                 215                 220

Tyr Pro Leu Gly Gln Gly Ser Phe Arg Pro Ser Gln Gln Asn Pro Gln
225                 230                 235                 240

Ala Gln Gly Ser Val Gln Pro Gln Gln Leu Pro Gln Phe Glu Glu Ile
                245                 250                 255

Arg Asn Leu Ala Arg Lys
            260

<210> SEQ ID NO 182
<211> LENGTH: 282
<212> TYPE: PRT
<213> ORGANISM: Triticum aestivum

<400> SEQUENCE: 182

Met Asn Ile Gln Val Asp Pro Ser Ser Gln Val Pro Trp Pro Gln Gln
1               5                   10                  15

Gln Pro Phe Pro Gln Pro His Gln Pro Phe Ser Gln Gln Pro Gln Gln
            20                  25                  30

Thr Phe Pro Gln Pro Gln Gln Thr Phe Pro His Gln Pro Gln Gln Gln
        35                  40                  45

Phe Ser Gln Pro Gln Pro Gln Gln Gln Phe Ile Gln Pro Gln Gln
    50                  55                  60

Pro Phe Pro Gln Gln Pro Gln Gln Thr Tyr Pro Gln Arg Pro Gln Gln
65                  70                  75                  80

Pro Phe Pro Gln Thr Gln Gln Pro Gln Gln Pro Phe Pro Gln Ser Gln
                85                  90                  95

Gln Pro Gln Gln Pro Phe Pro Gln Pro Gln Gln Phe Pro Gln Pro
            100                 105                 110

Gln Gln Pro Gln Gln Ser Phe Pro Gln Gln Pro Ser Leu Ile Gln
    115                 120                 125
```

```
Gln Ser Leu Gln Gln Gln Leu Asn Pro Cys Lys Asn Phe Leu Leu Gln
        130                 135                 140

Gln Cys Lys Pro Val Ser Leu Val Ser Ser Leu Trp Ser Met Ile Leu
145                 150                 155                 160

Pro Arg Ser Asp Cys Gln Val Met Arg Gln Gln Cys Cys Gln Gln Leu
                165                 170                 175

Ala Gln Ile Pro Gln Gln Leu Gln Cys Ala Ala Ile His Ser Ile Val
                180                 185                 190

His Ser Ile Ile Met Gln Gln Glu Gln Gln Glu Gln Arg Gln Gly Val
        195                 200                 205

Gln Ile Leu Val Pro Leu Ser Gln Gln Gln Gln Val Gly Gln Gly Thr
        210                 215                 220

Leu Val Gln Gly Gln Gly Ile Ile Gln Pro Gln Gln Pro Ala Gln Leu
225                 230                 235                 240

Glu Val Ile Arg Ser Leu Val Leu Gln Thr Leu Ala Thr Met Cys Asn
                245                 250                 255

Val Tyr Val Pro Pro Tyr Cys Ser Thr Ile Arg Ala Pro Phe Ala Ser
                260                 265                 270

Ile Val Ala Gly Ile Gly Gly Gln Tyr Arg
        275                 280

<210> SEQ ID NO 183
<211> LENGTH: 28
<212> TYPE: PRT
<213> ORGANISM: Triticum monococcum

<400> SEQUENCE: 183

Ala Arg Gln Leu Asn Pro Ser Asp Gln Glu Leu Gln Ser Pro Gln Gln
1               5                   10                  15

Leu Tyr Pro Gln Gln Pro Tyr Pro Gln Gln Pro Tyr
                20                  25
```